United States Patent
Adams et al.

(10) Patent No.: US 10,405,571 B2
(45) Date of Patent: Sep. 10, 2019

(54) COMPOSITIONS AND METHODS FOR PRODUCING TOBACCO PLANTS AND PRODUCTS HAVING ALTERED ALKALOID LEVELS

(71) Applicant: Altria Client Services LLC, Richmond, VA (US)

(72) Inventors: Andrew Carl Adams, Midlothian, VA (US); Marcos Fernando de Godoy Lusso, Chesterfield, VA (US); Sreepriya Pramod, Glen Allen, VA (US); Dongmei Xu, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 15/192,480

(22) Filed: Jun. 24, 2016

(65) Prior Publication Data

US 2016/0374387 A1    Dec. 29, 2016

Related U.S. Application Data

(60) Provisional application No. 62/335,772, filed on May 13, 2016, provisional application No. 62/271,780, filed on Dec. 28, 2015, provisional application No. 62/186,854, filed on Jun. 30, 2015, provisional application No. 62/185,268, filed on Jun. 26, 2015.

(51) Int. Cl.
| | |
|---|---|
| *A24B 15/10* | (2006.01) |
| *A24D 1/04* | (2006.01) |
| *A24D 3/04* | (2006.01) |
| *A01H 5/12* | (2018.01) |
| *C12N 15/82* | (2006.01) |
| *A24B 3/12* | (2006.01) |
| *A24B 13/02* | (2006.01) |
| *A24B 13/00* | (2006.01) |

(52) U.S. Cl.
CPC ............... *A24B 15/10* (2013.01); *A01H 5/12* (2013.01); *A24B 3/12* (2013.01); *A24B 13/00* (2013.01); *A24B 13/02* (2013.01); *A24D 1/045* (2013.01); *A24D 3/043* (2013.01); *C12N 15/8243* (2013.01)

(58) Field of Classification Search
None
See application file for complete search history.

(56) References Cited

U.S. PATENT DOCUMENTS

| | | |
|---|---|---|
| 1,055,360 A | 3/1913 | Sartig |
| 1,304,539 A | 5/1919 | Brinkhaus |
| 1,577,768 A | 3/1926 | Smith |
| 1,620,298 A | 3/1927 | Smith |
| 1,671,259 A | 5/1928 | Schloesing |
| 1,927,180 A | 9/1933 | McConnell |
| 1,962,145 A | 6/1934 | Gross et al. |
| 2,105,446 A | 1/1938 | Wilson |
| 2,136,485 A | 11/1938 | Berka et al. |
| 2,429,567 A | 10/1947 | Sows |
| 2,760,495 A | 8/1956 | Samfield et al. |
| 3,046,997 A | 7/1962 | Hind |
| 3,139,435 A | 6/1964 | Staley et al. |
| 3,258,015 A | 6/1966 | Ellis et al. |
| 3,280,823 A | 10/1966 | Bayley et al. |
| 3,356,094 A | 12/1967 | Ellis et al. |
| 3,396,735 A | 8/1968 | von Bethmann et al. |
| 3,584,630 A | 6/1971 | Innskeep |
| 3,612,066 A | 10/1971 | Jones et al. |
| 3,861,400 A | 1/1975 | Perkins et al. |
| 4,037,609 A | 7/1977 | Newton et al. |
| 4,038,993 A | 8/1977 | Geiss et al. |
| 4,068,671 A | 1/1978 | Casey |
| 4,150,677 A | 4/1979 | Osborne, Jr. et al. |
| 4,153,063 A | 5/1979 | Roselius et al. |
| 4,155,909 A | 5/1979 | Sanders et al. |
| 4,215,706 A | 8/1980 | Larson et al. |
| 4,220,781 A | 9/1980 | Sanders et al. |
| 4,236,532 A | 12/1980 | Schweizer et al. |
| 4,321,387 A | 3/1982 | Chavdarian et al. |
| 4,332,945 A | 6/1982 | Edwards, III |

(Continued)

FOREIGN PATENT DOCUMENTS

| | | |
|---|---|---|
| AU | 2015100914 A4 | 8/2015 |
| CA | 2330782 A1 | 7/2002 |

(Continued)

OTHER PUBLICATIONS

Hibi et al., 1994, The Plant Cell 6: 723-735.*
Chaplin and Weeks, 1976, Crop Science, 16: 416-418.*
Shoji et al., 2010, The Plant Cell 22: 3390-3409.*
Notice of Observation by a Third Party in the corresponding European Application No. 16738293.6, dated Sep. 24, 2018.*
Bowman et al., "Revised North Carolina grade index for flue-cured tobacco," *Tobacco Science*, 32:39-40 (1988).
Chaplin et al., "Association Between Percent Total Alkaloids and Other Traits in Flue-cured Tobacco," *Crop Science*, 16:416-418 (1976).

(Continued)

*Primary Examiner* — Bratislav Stankovic
(74) *Attorney, Agent, or Firm* — David R. Marsh; Arnold & Porter Kaye Scholer LLP

(57) ABSTRACT

The present disclosure provides the identification of tobacco Nic1 locus. Also provided are tobacco plants with altered total alkaloid and nicotine levels and commercially acceptable leaf grade, their development via breeding or transgenic approaches, and production of tobacco products from these tobacco plants. Also provided are compositions and methods for producing tobacco plants having novel Nic1 mutations or alleles to reduce nicotine levels. Further provided are sequence polymorphisms and molecular markers for breeding tobacco with reduced nicotine or nicotine free while maintaining tobacco leaf grade and tobacco product quality.

20 Claims, 7 Drawing Sheets

Specification includes a Sequence Listing.

(56) References Cited

U.S. PATENT DOCUMENTS

| | | |
|---|---|---|
| 4,340,072 A | 7/1982 | Bolt et al. |
| 4,442,292 A | 4/1984 | Edwards, III |
| 4,452,984 A | 6/1984 | Edwards, III |
| 4,516,590 A | 5/1985 | Teng |
| 4,528,993 A | 7/1985 | Sensabaugh et al. |
| 4,557,280 A | 12/1985 | Gravely et al. |
| 4,590,278 A | 5/1986 | Edwards, III |
| 4,595,024 A | 6/1986 | Greene et al. |
| 4,660,577 A | 4/1987 | Sensabaugh et al. |
| 4,676,259 A | 6/1987 | Ellis et al. |
| 4,732,856 A | 3/1988 | Federoff |
| 4,762,785 A | 8/1988 | Comai |
| 4,821,749 A | 4/1989 | Toft et al. |
| 4,830,028 A | 5/1989 | Lawson et al. |
| 4,848,373 A | 7/1989 | Lenkey |
| 4,898,188 A | 2/1990 | Niven, Jr. et al. |
| 4,945,050 A | 7/1990 | Sanford et al. |
| 4,967,771 A | 11/1990 | Fagg et al. |
| 4,987,907 A | 1/1991 | Townend |
| 5,004,863 A | 4/1991 | Umbeck |
| 5,013,658 A | 5/1991 | Dooner et al. |
| 5,015,741 A | 5/1991 | Osdene et al. |
| 5,018,540 A | 5/1991 | Grubbs et al. |
| 5,025,812 A | 6/1991 | Fagg et al. |
| 5,031,646 A | 7/1991 | Lippiello et al. |
| 5,050,621 A | 9/1991 | Creighton et al. |
| 5,065,775 A | 11/1991 | Fagg |
| 5,104,310 A | 4/1992 | Saltin |
| 5,119,835 A | 6/1992 | Heemann et al. |
| 5,138,062 A | 8/1992 | Osdene et al. |
| 5,141,131 A | 8/1992 | Miller, Jr. et al. |
| 5,149,645 A | 9/1992 | Hoekema et al. |
| 5,159,135 A | 10/1992 | Umbeck |
| 5,177,010 A | 1/1993 | Goldman et al. |
| 5,231,019 A | 7/1993 | Paszkowski et al. |
| 5,260,205 A | 11/1993 | Nalcatani et al. |
| 5,285,798 A | 2/1994 | Banerjee et al. |
| 5,369,023 A | 11/1994 | Nakatani et al. |
| 5,372,149 A | 12/1994 | Roth et al. |
| 5,463,174 A | 10/1995 | Moloney et al. |
| 5,464,763 A | 11/1995 | Schilperoort et al. |
| 5,479,948 A | 1/1996 | Counts et al. |
| 5,491,081 A | 2/1996 | Webb |
| 5,497,792 A | 3/1996 | Prasad et al. |
| 5,563,055 A | 10/1996 | Townsend et al. |
| 5,589,367 A | 12/1996 | Donson et al. |
| 5,659,026 A | 8/1997 | Baszczynski et al. |
| 5,665,262 A | 9/1997 | Hajaligol et al. |
| 5,666,976 A | 9/1997 | Adams et al. |
| 5,666,977 A | 9/1997 | Higgins et al. |
| 5,666,987 A | 9/1997 | Combs |
| 5,668,295 A | 9/1997 | Wahab et al. |
| 5,684,241 A | 11/1997 | Nalcatani et al. |
| 5,689,035 A | 11/1997 | Webb |
| 5,713,376 A | 2/1998 | Berger |
| 5,814,618 A | 9/1998 | Bujard et al. |
| 5,866,785 A | 2/1999 | Donson et al. |
| 5,879,918 A | 3/1999 | Tomes et al. |
| 5,880,164 A | 3/1999 | Keenan |
| 5,889,190 A | 3/1999 | Donson et al. |
| 5,889,191 A | 3/1999 | Turpen |
| 5,932,782 A | 8/1999 | Bidney |
| 5,981,840 A | 11/1999 | Zhao et al. |
| 6,072,050 A | 6/2000 | Bowen et al. |
| 6,153,119 A | 11/2000 | Sung |
| 6,423,520 B1 | 7/2002 | Conkling et al. |
| 6,586,661 B1 | 7/2003 | Conkling et al. |
| 6,694,985 B1 | 2/2004 | Kim |
| 6,761,176 B2 | 8/2004 | Sun |
| 6,772,769 B2 | 8/2004 | Sun |
| 6,907,887 B2 * | 6/2005 | Conkling .............. A24B 15/10 131/270 |
| 6,911,541 B2 | 6/2005 | Conkling et al. |
| 6,959,712 B2 | 11/2005 | Bereman et al. |
| 7,025,067 B2 | 4/2006 | Chatterjee |
| 7,192,771 B2 | 3/2007 | Conkling et al. |
| 7,238,861 B2 | 7/2007 | Kasulcabe et al. |
| 7,293,564 B2 | 11/2007 | Perfetti et al. |
| 7,304,220 B2 | 12/2007 | Conkling et al. |
| 7,408,098 B2 | 8/2008 | Conkling et al. |
| 7,425,670 B2 | 9/2008 | Conkling et al. |
| 7,446,242 B2 | 11/2008 | Kasukabe et al. |
| 7,538,071 B2 | 5/2009 | Berger |
| 7,605,308 B2 | 10/2009 | Conkling et al. |
| 7,645,925 B2 | 1/2010 | Conkling et al. |
| 7,665,470 B2 | 2/2010 | Mallmann et al. |
| 7,665,471 B2 | 2/2010 | Mallmann et al. |
| 7,665,472 B2 | 2/2010 | Mallmann et al. |
| 7,667,104 B2 | 2/2010 | Mallmann et al. |
| 7,667,105 B2 | 2/2010 | Mallmann et al. |
| 7,667,106 B2 | 2/2010 | Mallmann et al. |
| 7,700,834 B2 | 4/2010 | Xu et al. |
| 7,795,503 B2 | 9/2010 | Apuya et al. |
| 7,795,509 B2 | 9/2010 | Colliding et al. |
| 7,847,163 B2 | 12/2010 | Mallmann et al. |
| 7,847,164 B2 | 12/2010 | Mallmann et al. |
| 7,847,165 B2 | 12/2010 | Mallmann et al. |
| 7,888,554 B2 | 2/2011 | Kasukabe et al. |
| 8,410,341 B2 | 4/2013 | Page et al. |
| 8,624,083 B2 | 1/2014 | Page et al. |
| 8,759,101 B2 | 6/2014 | Timko et al. |
| 8,791,329 B2 | 7/2014 | Hashimoto et al. |
| 8,822,757 B2 | 9/2014 | Page et al. |
| 8,871,999 B2 | 10/2014 | Howe et al. |
| 8,887,737 B2 | 11/2014 | Howell et al. |
| 8,895,472 B2 | 11/2014 | Yang et al. |
| 8,980,633 B2 | 3/2015 | Timko et al. |
| 8,987,555 B2 | 3/2015 | Hashimoto et al. |
| 9,004,073 B2 | 4/2015 | Tucker et al. |
| 9,004,074 B2 | 4/2015 | Nauryzbaev et al. |
| 9,022,040 B2 | 5/2015 | Murphy |
| 9,029,656 B2 | 5/2015 | Hashimoto et al. |
| 9,102,948 B2 | 8/2015 | Hashimoto et al. |
| 9,121,030 B2 | 9/2015 | Page et al. |
| 9,133,468 B2 | 9/2015 | Page et al. |
| 9,139,841 B2 | 9/2015 | Fernández et al. |
| 9,150,872 B2 | 10/2015 | Page et al. |
| 9,157,089 B2 | 10/2015 | Page et al. |
| 9,157,090 B2 | 10/2015 | Page et al. |
| 9,175,052 B2 | 11/2015 | Gemrdi et al. |
| 9,175,302 B2 | 11/2015 | Page et al. |
| 9,234,205 B2 | 1/2016 | Hatzfeld |
| 9,422,346 B2 | 8/2016 | Noguchi et al. |
| 9,422,532 B2 | 8/2016 | Page et al. |
| 9,422,533 B2 | 8/2016 | Page et al. |
| 9,439,452 B2 | 9/2016 | Albino et al. |
| 9,462,754 B2 | 10/2016 | Scott et al. |
| 9,551,003 B2 | 1/2017 | Hashimoto et al. |
| 9,554,595 B2 | 1/2017 | Buchberger |
| 9,580,722 B2 | 2/2017 | Qu et al. |
| 9,677,083 B2 | 6/2017 | Timko et al. |
| 9,701,978 B2 | 7/2017 | Timko et al. |
| 9,719,103 B2 | 8/2017 | Hashimoto et al. |
| 9,732,350 B2 | 8/2017 | Page et al. |
| 9,752,156 B2 | 9/2017 | Page et al. |
| 9,796,984 B2 | 10/2017 | Howe et al. |
| 9,814,258 B2 | 11/2017 | Pandolfino |
| 9,834,780 B2 | 12/2017 | Hashimoto et al. |
| 9,856,487 B2 | 1/2018 | Hashimoto et al. |
| 9,879,272 B2 | 1/2018 | Page et al. |
| 2002/0108151 A1 | 8/2002 | Conkling et al. |
| 2003/0018997 A1 | 1/2003 | Conkling et al. |
| 2003/0131857 A1 | 7/2003 | Kim et al. |
| 2003/0140366 A1 | 7/2003 | Conkling et al. |
| 2003/0200975 A1 | 10/2003 | Rosen et al. |
| 2004/0094170 A1 | 5/2004 | Zho et al. |
| 2004/0103454 A1 | 5/2004 | Conkling et al. |
| 2004/0118422 A1 | 6/2004 | Lundin et al. |
| 2004/0144397 A1 | 7/2004 | Conkling |
| 2004/0168211 A1 | 8/2004 | Conkling et al. |
| 2005/0000531 A1 | 1/2005 | Shi |
| 2005/0072047 A1 | 4/2005 | Conkling et al. |
| 2005/0161056 A1 | 7/2005 | Conkling |
| 2005/0178398 A1 | 8/2005 | Breslin et al. |

(56) References Cited

U.S. PATENT DOCUMENTS

| | | |
|---|---|---|
| 2005/0263165 A1 | 12/2005 | Oh et al. |
| 2005/0263166 A1 | 12/2005 | Oh et al. |
| 2006/0057723 A1 | 3/2006 | Conkling et al. |
| 2006/0060211 A1 | 3/2006 | Conkling |
| 2006/0191035 A1 | 8/2006 | Conkling et al. |
| 2006/0191036 A1 | 8/2006 | Conkling et al. |
| 2006/0191039 A1 | 8/2006 | Conkling et al. |
| 2006/0191547 A1 | 8/2006 | Conkling |
| 2006/0191548 A1 | 8/2006 | Strickland et al. |
| 2006/0191549 A1 | 8/2006 | Conkling |
| 2006/0195936 A1 | 8/2006 | Conkling et al. |
| 2006/0200872 A1 | 9/2006 | Conkling et al. |
| 2006/0225154 A1 | 10/2006 | Kasulcabe et al. |
| 2006/0236434 A1 | 10/2006 | Conkling et al. |
| 2006/0242730 A1 | 10/2006 | Conkling et al. |
| 2006/0243290 A1 | 11/2006 | Reich et al. |
| 2007/0011774 A1 | 1/2007 | Conkling et al. |
| 2007/0016975 A1 | 1/2007 | Conkling et al. |
| 2007/0034220 A1 | 2/2007 | Pandolfino |
| 2007/0240728 A1 | 10/2007 | Hashimoto et al. |
| 2008/0120737 A1 | 5/2008 | Hashimoto et al. |
| 2008/0292735 A1 | 11/2008 | Hashimoto et al. |
| 2009/0031457 A1 | 1/2009 | Howe et al. |
| 2009/0055964 A1 | 2/2009 | Gelesko et al. |
| 2009/0114235 A1 | 5/2009 | Mallmann et al. |
| 2009/0117212 A1 | 5/2009 | Mallmann et al. |
| 2009/0119788 A1 | 5/2009 | Mallmann et al. |
| 2009/0119789 A1 | 5/2009 | Mallmann et al. |
| 2009/0119790 A1 | 5/2009 | Mallmann et al. |
| 2009/0119791 A1 | 5/2009 | Mallmann et al. |
| 2009/0119806 A1 | 5/2009 | Mallmann et al. |
| 2009/0210958 A1 | 8/2009 | Page et al. |
| 2010/0132063 A1 | 5/2010 | Mallmann et al. |
| 2010/0132064 A1 | 5/2010 | Mallmann et al. |
| 2010/0138949 A1 | 6/2010 | Mallmann et al. |
| 2011/0126322 A1 | 5/2011 | Fernandez et al. |
| 2013/0048001 A1 | 2/2013 | Williams |
| 2013/0309749 A1 | 11/2013 | Page et al. |
| 2013/0318661 A1 | 11/2013 | Page et al. |
| 2014/0271733 A1 | 9/2014 | Kobal et al. |
| 2014/0298535 A1 | 10/2014 | Page et al. |
| 2015/0082484 A1 | 3/2015 | Howe et al. |
| 2015/0173319 A1 | 6/2015 | Frederick et al. |
| 2015/0203859 A1 | 7/2015 | Page et al. |
| 2015/0218575 A1 | 8/2015 | Hashimoto et al. |
| 2015/0322451 A1 | 11/2015 | Kidithipudi et al. |
| 2016/0002649 A1 | 1/2016 | Kidithipudi et al. |
| 2016/0017359 A1 | 1/2016 | Hatzfeld |
| 2016/0032299 A1 | 2/2016 | Hashimoto et al. |
| 2016/0050968 A1 | 2/2016 | Williams |
| 2016/0060645 A1 | 3/2016 | Page et al. |
| 2016/0060646 A1 | 3/2016 | Page et al. |
| 2016/0073675 A1 | 3/2016 | Page et al. |
| 2016/0032298 A1 | 4/2016 | Hashimoto et al. |
| 2016/0130601 A1 | 5/2016 | Page et al. |
| 2016/0270435 A1 | 9/2016 | Benjak et al. |
| 2016/0362702 A1 | 12/2016 | de Bont et al. |
| 2016/0374387 A1 | 12/2016 | Adams et al. |
| 2017/0009249 A1 | 1/2017 | Goossens et al. |
| 2017/0044564 A1 | 2/2017 | Page et al. |
| 2017/0055566 A1 | 3/2017 | Albino et al. |
| 2017/0079322 A1 | 3/2017 | Li et al. |
| 2017/0137835 A1 | 5/2017 | Qu et al. |
| 2017/0145432 A1 | 5/2017 | Hashimoto et al. |
| 2017/0166913 A1 | 6/2017 | Hashimoto et al. |
| 2017/0231267 A1 | 8/2017 | Shi et al. |
| 2017/0306341 A1 | 10/2017 | Timko et al. |
| 2017/0321223 A1 | 11/2017 | Page et al. |
| 2018/0049477 A1 | 2/2018 | Suzuki et al. |

FOREIGN PATENT DOCUMENTS

| | | |
|---|---|---|
| CN | 1088763 A | 7/1994 |
| CN | 1147354 A | 4/1997 |
| CN | 1214890 A | 4/1999 |
| CN | 1271550 A | 11/2000 |
| CN | 1374045 A | 10/2002 |
| CN | 1457709 | 11/2003 |
| CN | 1465300 A | 1/2004 |
| CN | 1511550 A | 7/2004 |
| CN | 1545950 A | 11/2004 |
| CN | 1676502 | 10/2005 |
| CN | 1923063 A | 3/2007 |
| CN | 101088425 A | 12/2007 |
| CN | 101116534 A | 2/2008 |
| CN | 101177669 B | 5/2008 |
| CN | 101263926 A | 9/2008 |
| CN | 101288504 A | 10/2008 |
| CN | 101422277 B | 5/2009 |
| CN | 101434926 B | 5/2009 |
| CN | 101579147 B | 11/2009 |
| CN | 101824391 B | 9/2010 |
| CN | 102266118 B | 12/2011 |
| CN | 102423132 B | 4/2012 |
| CN | 102715636 B | 10/2012 |
| CN | 102845476 B | 1/2013 |
| CN | 102986439 A | 3/2013 |
| CN | 102993286 B | 3/2013 |
| CN | 102993287 B | 3/2013 |
| CN | 103004770 A | 4/2013 |
| CN | 103012571 B | 4/2013 |
| CN | 103012572 B | 4/2013 |
| CN | 103012573 B | 4/2013 |
| CN | 103014029 A | 4/2013 |
| CN | 103357382 B | 10/2013 |
| CN | 103584279 A | 2/2014 |
| CN | 104146347 B | 11/2014 |
| CN | 104172464 A | 12/2014 |
| CN | 104770859 A | 7/2015 |
| CN | 104783321 A | 7/2015 |
| CN | 104921286 A | 9/2015 |
| CN | 105230476 A | 1/2016 |
| CN | 105595404 A | 5/2016 |
| CN | 105602961 A | 5/2016 |
| CN | 105985912 A | 10/2016 |
| CN | 106350467 A | 1/2017 |
| CN | 106490673 A | 3/2017 |
| CN | 106577771 A | 4/2017 |
| CN | 106723347 A | 5/2017 |
| CN | 206197007 U | 5/2017 |
| CN | 106867665 A | 6/2017 |
| CN | 107149161 A | 9/2017 |
| CN | 107212458 A | 9/2017 |
| CN | 107228914 A | 10/2017 |
| CN | 107287171 A | 10/2017 |
| CN | 107384816 A | 11/2017 |
| CN | 107411161 A | 12/2017 |
| CN | 107478745 A | 12/2017 |
| CN | 107485673 A | 12/2017 |
| CN | 107488223 A | 12/2017 |
| CN | 107495463 A | 12/2017 |
| CN | 107505411 A | 12/2017 |
| CN | 206808656 U | 12/2017 |
| CN | 107557437 A | 1/2018 |
| CN | 107568785 A | 1/2018 |
| CN | 107640760 A | 1/2018 |
| CN | 106551421 B | 2/2018 |
| CN | 107692302 A | 2/2018 |
| CN | 206994425 U | 2/2018 |
| CN | 107760618 A | 3/2018 |
| CN | 107812005 A | 3/2018 |
| DE | 2506100 | 8/1975 |
| DE | 19826554 A1 | 12/1999 |
| DO | P2001000244 A | 12/2002 |
| EP | 280817 | 9/1988 |
| EP | 1180335 | 2/2002 |
| EP | 1238594 B1 | 9/2002 |
| EP | 1723860 A1 | 11/2006 |
| IN | 411CHE2013 | 9/2013 |
| IN | 04740MU2015 | 12/2015 |
| JP | H11137232 A | 5/1999 |
| JP | 3061889 U | 6/1999 |
| JP | H11225734 A | 8/1999 |
| JP | 2000093149 A | 4/2000 |

(56) References Cited

FOREIGN PATENT DOCUMENTS

| | | |
|---|---|---|
| JP | 2004113148 A | 4/2004 |
| JP | 2008048715 A | 3/2008 |
| JP | 2015077071 A | 4/2015 |
| KR | 100296868 B1 | 12/1998 |
| KR | 100217828 B1 | 9/1999 |
| KR | 20000021254 U | 12/2000 |
| KR | 20030076816 A | 9/2003 |
| KR | 20030091821 A | 12/2003 |
| KR | 20040072407 A | 8/2004 |
| KR | 100700977 B1 | 2/2005 |
| KR | 100727575 | 3/2005 |
| KR | 1020080082124 | 9/2008 |
| RU | 2289991 C1 | 12/2006 |
| RU | 2289996 C1 | 12/2006 |
| RU | 2289997 C1 | 12/2006 |
| RU | 2290044 C1 | 12/2006 |
| RU | 2290046 C1 | 12/2006 |
| RU | 2326554 C1 | 6/2008 |
| RU | 2326557 C1 | 6/2008 |
| RU | 2326564 C1 | 6/2008 |
| RU | 2326565 C1 | 6/2008 |
| RU | 2326566 C1 | 6/2008 |
| RU | 2326573 C1 | 6/2008 |
| RU | 153016 U1 | 6/2015 |
| RU | 2595986 C1 | 8/2016 |
| WO | WO1994028142 | 12/1994 |
| WO | WO1998056923 | 12/1998 |
| WO | WO2000067558 | 11/2000 |
| WO | WO2002018607 | 3/2002 |
| WO | WO2002100199 | 12/2002 |
| WO | WO2003078629 | 9/2003 |
| WO | WO2003079829 | 10/2003 |
| WO | WO 2004/041006 A1 | 5/2004 |
| WO | WO2005004646 | 1/2005 |
| WO | WO2006004480 | 1/2006 |
| WO | WO2006050313 | 5/2006 |
| WO | WO2007075027 A1 | 7/2007 |
| WO | WO2008008844 | 1/2008 |
| WO | WO2008020333 | 2/2008 |
| WO | WO2009061421 | 5/2009 |
| WO | WO2009061422 | 5/2009 |
| WO | WO2009061437 | 5/2009 |
| WO | WO2009063312 | 5/2009 |
| WO | WO2010004070 | 1/2010 |
| WO | WO 2011/027315 A1 | 3/2011 |
| WO | WO 2011/088180 A1 | 7/2011 |
| WO | WO2011102394 A1 | 8/2011 |
| WO | WO2014134354 | 9/2014 |
| WO | WO2014150926 | 9/2014 |
| WO | WO2015085299 | 6/2015 |
| WO | WO2015124620 | 8/2015 |
| WO | WO2015124799 A1 | 8/2015 |
| WO | WO2015157359 A1 | 10/2015 |
| WO | WO2016004193 | 1/2016 |
| WO | WO2016179356 A1 | 11/2016 |
| WO | WO2016210303 A1 | 12/2016 |
| WO | WO2017096254 A1 | 6/2017 |
| WO | WO2017097840 A1 | 6/2017 |
| WO | WO2018045140 A1 | 3/2018 |
| WO | WO 2018/237107 A1 | 12/2018 |

OTHER PUBLICATIONS

Christensen et al., "Maize polyubiquitin genes: structure, thermal perturbation of expression and transcript splicing, and promoter activity following transfer to protoplasts by electroporation," *Plant Mal Biol.*, 18:675-689 (1992).
Christensen et al., "Sequence analysis and transcriptional regulation by heat shock of polyubiquitin transcripts from maize," *Plant Mol Biol.*, 12(6):619-632 (1989).
Christou et al., "Stable Transformation of Soybean Callus by DNA-Coated Gold Particles," *Plant Physiol.*, 87:671-674 (1988).
Collins et al., "Determination of nicotine alkaloids in tobacco using the Autoanalyzer," *Tobacco Science*, 13:79-81 (1969).

Crossway et al., "Micromanipulation techniques in plant biotechnology," BioTechniques, 4:320-334 (1986).
D'Halluin et al., "Transgenic Maize Plants by Tissue Electroporation," *The Plant Cell*, 4:1495-1505 (1992).
Davis et al., "A combined automated procedure for the determination of reducing sugars and nicotine alkaloids in tobacco products using a new reducing sugar method," *Tobacco Science*, 20:139-144 (1976).
Davis et al., "4B Seedling Production," *Tobacco: Production, Chemistry and Technology*, pp. 70-103(1999).
De Wet et al., "Exogenous gene transfer in maize (*Zea mays*) using DNA-treated pollen," *Experimental Manipulation of Ovule Tissues*, pp. 197-209 (1985).
Estruch et al., "Transgenic plants: An emerging approach to pest control," *Nature Biotechnology* 15:137-141 (1997).
Fedoroff et al., "Cloning of the bronze locus in maize by a simple and generalizable procedure using the transposable controlling element Activator (Ac)," 81:3825-3829 (1984).
Finer et al., "Transformation of soybean via particle bombardment of embryogenic suspension culture tissue, " *In Vitro Cell Dev. Biol.* 27(4):175-182 (1991).
Gaj et al., "ZFN, TALEN and CRISPR/Cas-based methods for genome Engineering," *Trends Biotechnol.*, 31(7):397-405 (2013).
Gatz et al., "Regulation of a modified CaM V35S promoter by the Tn10-encoded Tet repressor in transgenic tobacco," *Mol Gen. Genet.* 227:229-237 (1991).
Hibi et al., "Gene Expression in Tobacco Low-Nicotine Mutants," *The Plant Cell*, 6:723-735 (1994).
Hibi et al., "Putrescine N-Methyltransferase in Cultured Roots of Hyoscyamus albus1: n-Butylamine as a Potent Inhibitor of the Transferase both in Vitro and in Vivo," *Plant Physiology* 100: 826-35 (1992).
Hildering et al., "Chimeric structure of the tomato plant after seed treatment with Ems and X-rays," *Radiation Botany*, pp. 317-320 (1965).
Hoekema et al., "A binary plant vector strategy based on separation of vir- and T-region of the *Agrobacterium turnefaciens* Ti-plasmid," *Nature*, 303:171-180 (1983).
Kaeppler et al., "Silicon carbide fiber-mediated DNA delivery into plant cells," *Plant Cell Reports*, 9:415-418(1990).
Kaeppler et al., "Silicon carbide fiber-mediated stable transformation of plant cells," *Theoretical and Applied Genetics*, 84(5):560-566 (1992).
Kidd et al., "The A and B loci in tobacco regulate a network of stress response genes, few of which are associated with nicotine biosynthesis," *Plant Mol Biol.*, 60(5):699-716 (2006).
Kosambi, "The estimation of map distance from recombinant values," *Annals of Eugenics*, 12:172-175 (1944).
Last et al., "An improved promoter for gene expression in cereal cells," *Theor. Appl. Genet.*, 81:581-588 (1991).
Legg et al., "Inheritance of percent total alkaloids in *Nicotiana tabacum* L.; populations derived from crosses of low alkaloid lines with burley and flue-cured varieties," *J Hered*, 60:213-217 (1969).
Legg et al., "Registration of La Burley 21 Tobacco Germplasm1," Crop Science, 10:212 (1970).
McCabe et al., "Stable transformation of soybean (Glycine max) by particle acceleration," *Biotechnology*, 6:923-926 (1988).
McCallum et al., "Targeted screening for induced mutations," *Nat. Biotechnol.*, 18:455-457 (2000).
McNellis et al., "Glucocorticoid-inducible expression of a bacterial avirulence gene in transgenic *Arabidopsis* induces hypersensitive cell death," *Plant J.* 14(2):247-257 (1998).
Miller et al., "A grade index for type 22 and 23 fire-cured tobacco." Tobacco International 192(22):55-57 (1990). Abstract retrieved from https://www.cabdirect.org/cabdirect/abstract/19910747272.
Morita et al., "Vacuolar transport of nicotine is mediated by a multidrug and toxic compound extrusion (MATE) transporter in Nicotiana tabacum," *Proc Natl Acad Sci*, 106:2447-2452 (2009).
Odell et al., "Identification of DNA sequences required for activity of the cauliflower mosaic virus 35S promoter," *Nature*, 313:810-812 (1985).
Paszkowski et al., "Direct gene transfer to plants," *EMBO J.*, 3(12):2717-2722 (1984).

(56) References Cited

OTHER PUBLICATIONS

Porta et al., "Use of viral replicons for the expression of genes in plants," *Molecular Biotechnology*, 5:209-221 (1996).
Reed et al., "The A and B of *Nicotiana tabacum* have non-equivalent effects on the mRNA levels of four alkaloid biosynthethic genes," *Plant Science*, 167:1123-1130 (2004).
Riggs et al., "Stable transformation of tobacco by electroporation: Evidence for plasmid concatenation," *Proc. Natl. Acad. Sci.*, 83:5602-5606 (1986).
Sanford et al., "Optimizing the biolistic process for different biological applications," *Methods Enzymol.*, 217:483-509 (1993).
Saunders el al., "Nicotine Biosynthetic Enzyme Activities in *Nicotiana tabacum* L. Genotypes withDifferent Alkaloid Levels," *Plant Physiol.*, 64:236-240 (1979).
Schena et al., "A steroid-inducible gene expression system for plant cells," *Proc. Natl. Acad. Sci.*, 88:10421-10425 ( 1991).
Sears et al., "NtERF32: a non-NIC2 locus AP2/ERF transcription factor required in jasmonate-inducible nicotine biosyntehsis in tobacco," *Plant Mol Biol*, 84:49-66 (2014).
Shillito et al., "Direct gene transfer to protoplasts of dicotyledonous and monocotyledonous plants by a number of methods, including electroporation," *Methods in Enzymology*, 153:313-336 (1987).
Shoji et al., "Clustered Transcription Factor Genes Regulate Nicotine Biosynthesis in Tobacco," *The Plant Cell*, 22:3390-3409 (2010).
Singh et al., "Cytological characterization of transgenic soybean," *Theor Appl Genet.* 96:319-324 (1998).
Todd et al., "A functional genomics screen identifies diverse transcription factors that regulate alkaloid biosynthesis in *Nicotiana benthamiana*," *The Plant J.* 62:589-600(2010).
Tomes et al., "Direct DNA Transfer into Intact Plant Cells Via Microprojectile Bombardment," *Plant Cell Tissue and Organ Culture*, pp. 197-213 (1995).
Velten et al., "Isolation of a dual plant promoter fragment from the Ti plasmid of *Agrobacterium tumefaciens*," *EMBO J*, 3:2723-2730 (1984).
Verkerk, "Chimerism of the tomato plant after seed irradiation with fast neutrons," *Neth. J. Agric. Sci.*, 19:197-203 (1971).
Welting et al., "Foreign Genes in Plants: Transfer, Structure, Expression, and Applications," *Ann. Rev. Genet.*, 22:421-477 (1988).
Wernsman et al., "Tobacco," *Crop Species*, 2:669-698 (1987).
Shoji et al. "Smoking Out the Masters: Transcriptional Regulators for Nicotine Biosynthesis in Tobacco" *Plant Biotech*, 30:217-224 (2013).
U.S. Appl. No. 62/616,959, filed Jan. 12, 2018, Adams et al.
U.S. Appl. No. 62/625,878, filed Feb. 2, 2018, Adams et al.
Albrecht et al., "Activation of olfactory and trigeminal cortical areas following stimulation of the nasal mucosa with low concentrations of S(−)-nicotine vapor-an fMRI study on chemosensory perception," *Human Brain Mapping* 30(3):699-710 (2009).
"Alkaloid Reduced Tobacco (ART) Program," Philip Morris USA (1994).
Cai et al., "(R)-nicotine biosynthesis, metabolism and translocation in tobacco as determined by nicotine demethylase mutants," *Phytochemistry* 95:188-96 (2013).
Chakrabarti et al., "CYP82E4-mediated nicotine to nornicotine conversion in tobacco is regulated by a senescence-specific signaling pathway," *Plant Molecular Biology* 66(4):415-27 (2008).
Drenan et al., "In Vivo Activation of Midbrain Dopamine Neurons via Sensitized, High-Affinity α6* Nicotinic Acetylcholine Receptors," *Neuron* 60(1):123-36 (2008).
Hashimoto et al., "Tropane Alkaloid Production in Hyoscyamus Root Cultures," *Journal of Plant Physiology* 124(1-2):61-75 (1986).
Hibi et al., "Gene Expression in Tobacco Low-Nicotine Mutants," *The Plant Cell* 6(5):723-735 (1994).
Hu et al., "Characterization of Pseudooxynicotine Amine Oxidase of Pseudomonas putida S16 that Is Crucial for Nicotine Degradation," *Scientific Reports* 5:17770 (2015).
Kajikawa et al., "A model for evolution and regulation of nicotine biosynthesis regulation in tobacco," *Plant Signaling & Behavior* 12(6):e1338225 (2017).

Kajikawa et al., "Genomic Insights into the Evolution of the Nicotine Biosynthesis Pathway in Tobacco," *Plant Physiology* 174(2):999-1011 (2017).
Kajikawa et al., "Vacuole-Localized Berberine Bridge Enzyme-Like Proteins are Required for a Late Step of Nicotine Biosynthesis in Tobacco," *Plant Physiology* 155(4):2010-22 (2011).
Kato et al., "Tobacco Nicotine Uptake Permease Regulates the Expression of a Key Transcription Factor Gene in the Nicotine Biosynthesis Pathway," *Plant Physiology* 166(4):2195-204 (2014).
Kidd et al., "The A and B loci in tobacco regulate a network of stress response genes, few of which are associated with nicotine biosynthesis," *Plant Molecular Biology* 60:699-716 (2006).
Legg et al., "Inheritance of Percent Total Alkaloids in *Nicotiana tabactem* L.," *The Journal of Heredity* 213-217 (1969).
Lewis et al., "Transgenic and Mutation-Based Suppression of a Berberine Bridge Enzyme-Like (BBL) Gene Family Reduces Alkaloid Content in Field-Grown Tobacco," *PloS One* 10(2):e0117273 (2015).
Liu et al., "Physiological and Biochemical Characterization of a Novel Nicotine-Degrading Bacterium Pseudomonas geniculata N1," *PloS One* 9(1):e84399 (2014).
Ma et al., "Alternative splicing of basic chitinase gene PR3b in the low-nicotine mutants of Nicotiana tabacum L. cv. Burley 21," *Journal of Experimental Botany* 67(19):5799-809 (2016).
McKinney et al., "Cigarettes with different nicotine levels affect sensory perception and levels of biomarkers of exposure in adult smokers," *Nicotine & Tobacco Research* 16(7):948-60 (2014).
Šarčević et al., "Long-term Genetic Improvement and Genetic Diversity of Croatian Flue-cured Tobacco (*Nicotiana tabacum* L.) Cultivars," *Crop Science* 53(1):112-20 (2013).
Sato et al., "Metabolic engineering of plant alkaloid biosynthesis," *Proceedings of the National Academy of Sciences* 98(1):367-72 (2001).
Saunders et al., "Nicotine Biosynthetic Enzyme Activities in *Nicotiana tabacum* L. Genotypes with Different Alkaloid Levels," *Plant Physiol* 64:236-240 (1979).
Shoji et al., "Clustered Transcription Factor Genes Regulate Nicotine Biosynthesis in Tobacco," *The Plant Cell* 22(10):3390-409 (2010).
Shoji et al., "Smoking out the masters: transcriptional regulators for nicotine biosynthesis in tobacco," *Plant Biotechnology* 30(3):217-24 (2013).
Shulleeta et al., U.S. Appl. Entitled: "Differentially Expressed Tobacco cDNAs and Their Use in Affecting Tobacco Alkaloid Levels in Tobacco," https://www.industrydocumentslibrary.ucsf.edu/tobacco/docs/#id=xfwc0076 (1992).
Sun et al., "Comparative Analysis on Chemical Components and Sensory Quality of Aging Flue-Cured Tobacco from Four Main Tobacco Areas of China," *Agricultural Sciences in China* 10(8):1222-31 (2011).
Takizawa et al., "A virus-induced gene silencing approach for the suppression of nicotine content in Nicotiana benthamiana," *Plant Biotechnology* 24(3):295-300 (2007).
Tang et al., "Systematic Unraveling of the Unsolved Pathway of Nicotine Degradation in Pseudomonas," *PLoS Genetics* 9(10):e1003923 (2013).
Teper et al., "Nicotine-Induced Dystonic Arousal Complex in a Mouse Line Harboring a Human Autosomal-Dominant Nocturnal Frontal Lobe Epilepsy Mutation," *Journal of Neuroscience* (38):10128-42 (2007).
Todd et al., "A functional genomics screen identifies diverse transcription factors that regulate alkaloid biosynthesis in *Nicotiana benthamiana*," the *Plant Jouranl* 62:589-600 (2010).
Wang, "Factors in Nicotine Biosynthesis in Tobacco," *Dissertation* (2011).
Wang et al., "Current status and prospects for the study of *Nicotiana* genomics, genetics, and nicotine biosynthesis genes," *Mol Genet Genomics* 290:11-21 (2015).
Yang et al., "Transcriptome Profiling Identified Multiple Jasmonate ZIM-Domain Proteins Involved in the Regulation of Alkaloid Biosynthesis in Tobacco BY-2 Cells," *Plant Molecular Biology Reporter* 33(1):153-66 (2015).

(56) References Cited

OTHER PUBLICATIONS

Notice of Observations filed by a Third Party dated Sep. 24, 2018 in corresponding European Application No. 16738293.6.
Chintanakorn, "An Antisense Approach to StudV the Role of Arginine Decarboxylase and Putrescine N-Methyltransferase in Alkaloid Metabolism in *Nicotiana tabacum* L.," School of Biological Sciences, Melbourne, Australia, (2002).

* cited by examiner

COMPOSITIONS AND METHODS FOR PRODUCING TOBACCO PLANTS AND PRODUCTS HAVING ALTERED ALKALOID LEVELS

The present application claims the benefit of U.S. provisional application No. 62/185,268 filed Jun. 26, 2015 (pending), U.S. provisional application No. 62/186,854, filed Jun. 30, 2015 (pending), U.S. provisional application No. 62/271,780, filed Dec. 28, 2015, and U.S. provisional application No. 62/335,772, filed May 13, 2016 (pending), all of which are hereby incorporated by reference in their entireties.

INCORPORATION OF SEQUENCE LISTING

A sequence listing contained in the file named "P34319US04.txt" which is 3,579,889 bytes (measured in MS-Windows®) and created on Jun. 24, 2016, comprising 127 nucleotide sequences and 37 amino acid sequences, is filed electronically herewith and incorporated by reference in its entirety.

FIELD

The present disclosure provides the identification of tobacco Nic1 locus. Also provided are tobacco plants with altered total alkaloid and nicotine levels and commercially acceptable leaf grade, their development via breeding or transgenic approaches, and production of tobacco products from these tobacco plants.

BACKGROUND

Four major alkaloids are found in tobacco: nicotine, nornicotine, anabasine, and anatabine. Nicotine is the predominant alkaloid, usually accounting for more than 90% of the total alkaloids in commercial tobacco cultivars. Nicotine biosynthesis occurs predominantly in tobacco roots. Tobacco plants then transport nicotine through the vascular bundle to leaves where nicotine is then stored in the vacuoles.

A variety of factors affect tobacco alkaloid levels including genotype, environment, fertilization, and agronomic practices (for example, nicotine production is stimulated by topping, wounding, and herbivore damage). Low-alkaloid traits initially found in strains of Cuban cigar tobacco varieties were introduced into cigarette varieties through a series of backcrosses. Low-alkaloid tobacco germplasm was subsequently registered in the genetic background of cultivar Burley 21 (Legg et al., *Crop Science*, 10:212 (1970)). Genetic studies using the low alkaloid Burley 21 (LA BU21) lines indicated that two unlinked loci contribute to nicotine levels in the tobacco leaf. These two loci are referred to as Nic1 and Nic2. The nic1 and nic2 mutations in LA BU21 are semidominant. They show dose-dependent effects on nicotine levels, with the effects of nic1 about 2.4 times stronger than those of nic2. Molecular characterization of Nic2 locus has been reported. The nic2 mutation was shown to contain a deletion of a cluster of transcription factor genes from the ethylene responsive factor (ERF) family.

Reducing total alkaloid content in tobacco can have many benefits. It can increase the value of tobacco as a biomass resource. Increases in nicotinic alkaloid in tobacco plants may play an important role in protecting plants against insects and herbivores.

Consistent with alkaloids' role in insect defense, LA BU21 was reported to be extremely susceptible to insect damage (Legg et al., *Crop Science*, 10:212 (1970)). A further study comparing isogenic lines of flue-cured tobacco with low total alkaloids percentage (approximately 0.20%) with their "normal" recurring parents (total alkaloids 1.85 to 2.70%) reported that yield, grade index, total N, and reducing sugar content in the low alkaloid lines were lower than in the normal flue-cured cultivars (Chaplin and Weeks, *Crop Science*, 16(3):416-18 (1976)).

There is a need to identify novel genes that regulate tobacco nicotine levels, and to develop tobacco plants and products that contain altered nicotine levels (e.g., reduced nicotine) while maintaining (if not making superior) tobacco leaf quality.

SUMMARY

In some aspects, the present disclosure provides tobacco plants, or part thereof, comprising a mutation in Nic1 locus, a mutation in Nic2 locus, or both, wherein the tobacco plant is capable of producing leaves having a USDA grade index value of 50 or more.

In other aspects, the present disclosure provides tobacco plants, or part thereof, comprising a mutation in Nic1 locus, a mutation in Nic2 locus, or both, wherein the tobacco plant is capable of producing leaves having a USDA grade index value comparable to that of a control plant when grown in similar growth conditions, wherein the control plant shares an essentially identical genetic background with the tobacco plant except the mutation.

In some aspects, the present disclosure further provides non-transgenic tobacco plants, or part thereof, comprising a nicotine level selected from the group consisting of less than 2.0%, wherein the tobacco plants are capable of producing leaves having a USDA grade index value of 50 or more.

In other aspects, the present disclosure also provides a tobacco plant, or part thereof, comprising a non-transgenic mutation, wherein the non-transgenic mutation reduces the nicotine level of the tobacco plant to about 20% or less of the nicotine level of a control plant when grown in similar growth conditions, wherein the tobacco plant is capable of producing leaves having a USDA grade index value comparable to the USDA grade index value of the control plant, and wherein the control plant shares an essentially identical genetic background with the tobacco plant except the non-transgenic mutation.

In some aspects, the present disclosure provides tobacco plants, or part thereof, comprising a mutation in Nic1 locus, a mutation in Nic2 locus, or both, wherein the tobacco plant comprise a similar level of one or more tobacco aroma compounds selected from the group consisting of 3-methylvaleric acid, valeric acid, isovaleric acid, a labdenoid, a cembrenoid, a sugar ester, and a reducing sugar, compared to a control tobacco plant when grown in similar growth conditions.

In other aspects, the present disclosure provides tobacco plants, or part thereof, comprising a mutation in Nic1 locus, wherein the mutation is absent from LA Burley 21. In some aspects, tobacco plants provided herein comprise a shorter chromosome deletion at Nic1 locus compared to LA Burley 21. In other aspects, tobacco plants provided herein comprise no deletion of a complete gene or a complete genic coding sequence in Nic1 locus.

In some aspects, the present disclosure provides tobacco plants, or part thereof, comprising one or more mutations within one or more genes comprising a sequence having at least 80% identity to a sequence selected from the group consisting of SEQ ID NOs: 9 to 28, 75 to 82, 86 to 100, 145, and fragments thereof. In some aspects, tobacco plants provided herein comprise one or more non-naturally existing mutant alleles at Nic1 locus which reduce or eliminate one or more gene activity from Nic1 or Nic2 locus. In some aspects, these mutant alleles result in lower nicotine levels.

In other aspects, the present disclosure provides tobacco plants, or part thereof, comprising one or more mutations within one or more genes comprising a coding sequence having at least 80% identity to a sequence selected from the group consisting of SEQ ID NOs: 29 to 48, 83, 101 to 115, 146, and fragments thereof.

In some aspects, the present disclosure provides tobacco plants, or part thereof, comprising one or more mutations within one or more genes encoding a polypeptide having at least 80% identity to a sequence selected from the group consisting of SEQ ID NOs: 49 to 68, 84, 116 to 130, 147, and fragments thereof.

In other aspects, the present disclosure provides tobacco plants, or part thereof, comprising a heterologous expression cassette comprising a Nic1 inhibitory sequence of a gene comprising a sequence having at least 80% identity to a sequence selected from the group consisting of SEQ ID NOs: 9 to 28, 75 to 82, 86 to 100, 145, and fragments thereof, wherein the inhibitory sequence is operably linked to a promoter that is functional in a plant cell, and wherein the inhibitory sequence has at least 90% sequence identity to a fragment of at least 21 nucleotides of the sequence having at least 80% identity to a sequence selected from the group consisting of SEQ ID NOs: 9 to 28, 75 to 82, 86 to 100, 145, and fragments thereof.

In other aspects, the present disclosure provides recombinant DNA constructs comprising a promoter that is functional in a tobacco cell and operably linked to a polynucleotide that encodes an RNA molecule capable of binding to an RNA encoding a polypeptide having an amino acid sequence at least 80% identical to an amino acid sequence selected from the group consisting of SEQ ID NOs: 49 to 68, 84, 116 to 130, 147, and fragments thereof, and wherein the RNA molecule suppresses the expression of the polypeptide.

In some aspects, the present disclosure provides recombinant DNA constructs comprising a promoter that is functional in a tobacco cell and operably linked to a polynucleotide that encodes a polypeptide having an amino acid sequence at least 80% identical to an amino acid sequence selected from the group consisting of SEQ ID NOs: 49 to 68, 84, 116 to 130, 147, and fragments thereof.

The present disclosure further provides cured tobacco, tobacco blends, tobacco products comprising plant material from tobacco plants, lines, varieties or hybrids disclosed herein.

The present disclosure also provides methods for breeding tobacco lines, cultivars, or varieties comprising a desirable level of total alkaloid or nicotine, e.g., low nicotine or nicotine free. In some aspects, the present disclosure provides a method of introgressing a low nicotine trait into a tobacco variety, the method comprising: (a) crossing a first tobacco variety comprising a low nicotine trait with a second tobacco variety without the low nicotine trait to produce one or more progeny tobacco plants; (b) genotyping the one or more progeny tobacco plants for a polymorphic marker linked to the low nicotine trait, wherein the polymorphic marker is in a chromosomal interval flanked by any two of polymorphic loci listed in Table 3 or flanked by any two of polymorphic loci listed in Table 4; and (c) selecting a progeny tobacco plant comprising the low nicotine trait.

In some aspects, the present disclosure provides a method of introgressing a low nicotine trait into a tobacco variety, the method comprising: (a) crossing a first tobacco variety comprising a low nicotine trait with a second tobacco variety without the low nicotine trait to produce one or more progeny tobacco plants; (b) genotyping the one or more progeny tobacco plants for a polymorphic marker linked to the low nicotine trait, wherein the polymorphic marker is within 20 cM of any one of polymorphic loci listed in Tables 3, 4, 16, and 17; and (c) selecting a progeny tobacco plant comprising the low nicotine trait. In one aspect, a polymorphic marker is a SNP marker selected from the group consisting of SEQ ID Nos. 131 to 144.

In other aspects, the present disclosure provides a method of selecting a tobacco plant having a low nicotine trait, the method comprising: (a) isolating nucleic acids from a collection of tobacco germplasm; (b) assaying the nucleic acids for one or more markers closely linked to Nic1 locus; and (c) selecting a tobacco plant having a low nicotine trait based on the marker assay.

BRIEF DESCRIPTION OF THE SEQUENCES

Figure 1:
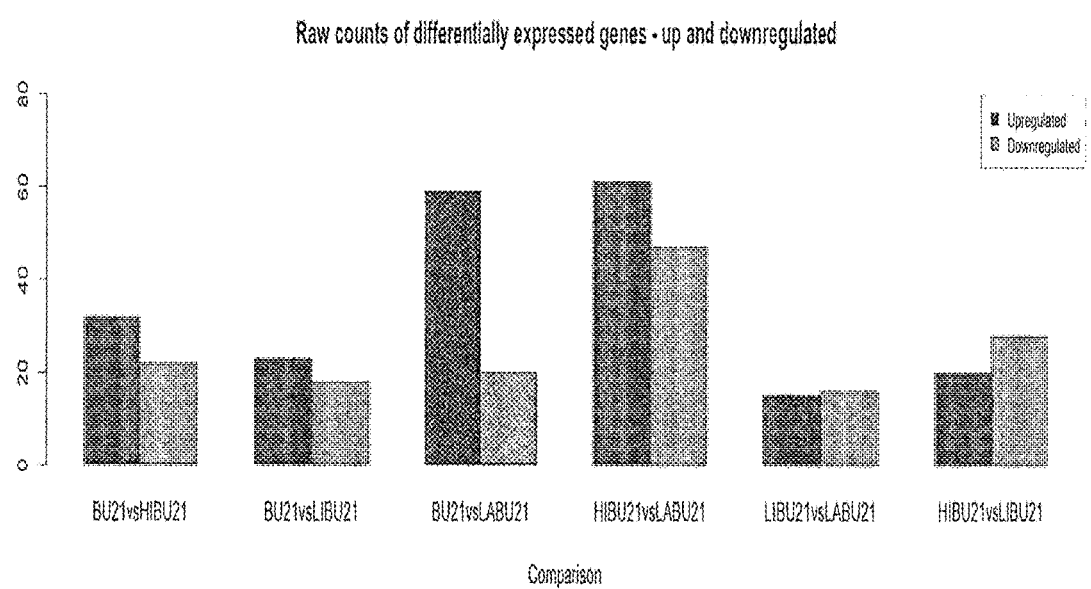
FIG. 1 shows the number of differentially regulated genes for each pairwise comparison within the group of BU21, HI BU21, LI BU21 and LA BU2.

SEQ ID No: 1 sets forth the sequence of a Nic1 associated deletion, Scaffold0002504, identified from LA BU21.

SEQ ID No: 2 sets forth the sequence of a Nic2 associated deletion, Scaffold0000549, identified from LA BU21.

SEQ ID Nos: 3 to 8 set forth primer sequences used for PCR confirmation of identified Nic1 and Nic2 deletions.

SEQ ID Nos: 9 to 28 set forth genomic sequences of 20 annotated genes in Nic1 associated deletion Scaffold0002504.

SEQ ID Nos: 29 to 48 set forth cDNA sequences of 20 annotated genes in Nic1 associated deletion Scaffold0002504.

SEQ ID Nos: 49 to 68 set forth amino acid sequences encoded by 20 annotated genes in Nic1 associated deletion Scaffold0002504.

SEQ ID Nos: 69 and 70 set forth exemplary transformation cassette sequences for suppressing g100614_Scaffold0002504 and g100631_Scaffold0002504 via RNA interference (RNAi).

SEQ ID Nos: 71 and 72 set forth reference TN90 alleles of sequence polymorphisms.

SEQ ID No: 73 sets forth the sequence of a tobacco genomic sequence assembly NT2.0-Scaffold4274 which comprises a re-sequenced segment of NT1.0-Scaffold0002504. Specifically, nucleotides 148796 to 282345 of NT2.0-Scaffold4274 correspond to and replace NT1.0-Scaffold0002504 between nucleotides 384701 to 542313 in the minus orientation.

SEQ ID No: 74 sets forth the sequence of a tobacco genomic sequence assembly NT2.0-Scaffold14415 which comprises a re-sequenced segment of NT1.0-Scaffold0002504. Specifically, nucleotides 1 to 59671 of NT2.0-Scaffold14415 correspond to and replace NT1.0-Scaffold0002504 between nucleotides 288601 to 363040 in the minus orientation.

SEQ ID Nos: 75 and 82 set forth re-sequenced and re-fined genomic sequences of eight annotated genes in Nic1 associated deletion.

SEQ ID Nos: 83 and 84 set forth further annotated cDNA and amino acid sequences of the gene in g100623_Scaffold0002504 based on re-sequencing.

SEQ ID No: 85 sets forth the genomic sequence of the complete Nic1 deletion region in LA BU21.

SEQ ID Nos: 86 to 100 set forth genomic sequences of 15 annotated genes in SEQ ID No: 85.

SEQ ID Nos: 101 to 115 set forth cDNA sequences of 15 annotated genes in SEQ ID No: 85.

SEQ ID Nos: 116 to 130 set forth protein sequences of 15 annotated genes in SEQ ID No: 85.

SEQ ID Nos: 131 to 142 set forth 12 SNP marker sequences flanking nic1 or nic2 deletion.

SEQ ID Nos: 143 and 144 set forth two SNP marker sequences associated with an ERF-39 like gene.

SEQ ID Nos: 145 to 147 set forth genomic, cDNA, and protein sequences of an ERF-39 like gene.

SEQ ID Nos: 148 to 164 set forth sequences of inverted repeat-containing RNAi cassettes targeting NDG1 to NDG15.

Various sequences disclosed herein include "N" in nucleotide sequences or "X" in amino acid sequences. "N" can be any nucleotide, e.g., A, T, G, C, or a deletion or insertion of one or more nucleotides. In some instant, a string of "N" are shown. The number of "N" does not necessarily correlate with the actual number of undetermined nucleotides at that position. The actual nucleotide sequences can be longer or shorter than the shown segment of "N". Similarly, "X" can be any amino acid residue or a deletion or insertion of one or more amino acids. Again, the number of "X" does not necessarily correlate with the actual number of undetermined amino acids at that position. The actual amino acid sequences can be longer or shorter than the shown segment of "X".

DETAILED DESCRIPTION

Unless defined otherwise, technical and scientific terms used herein have the same meaning as commonly understood by one of ordinary skill in the art. One skilled in the art will recognize many methods can be used in the practice of the present disclosure. Indeed, the present disclosure is in no way limited to the methods and materials described. For purposes of the present disclosure, the following terms are defined below.

Any references cited herein, including, e.g., all patents and publications are incorporated by reference in their entirety.

As used herein, the singular form "a," "an," and "the" include plural references unless the context clearly dictates otherwise. For example, the term "a compound" or "at least one compound" may include a plurality of compounds, including mixtures thereof.

The term "about" is used herein to mean approximately, roughly, around, or in the region of. When the term "about" is used in conjunction with a numerical range, it modifies that range by extending the boundaries above and below the numerical values set forth.

As used herein, a tobacco plant can be from any plant from the *Nicotiana* genus including, but not limited to *Nicotiana tabacum, Nicotiana amplexicaulis* PI 271989; *Nicotiana benthamiana* PI 555478; *Nicotiana bigelovii* PI 555485; *Nicotiana debneyi; Nicotiana excelsior* PI 224063; *Nicotiana glutinosa* PI 555507; *Nicotiana goodspeedii* PI 241012; *Nicotiana gossei* PI 230953; *Nicotiana hesperis* PI 271991; *Nicotiana knightiana* PI 555527; *Nicotiana maritima* PI 555535; *Nicotiana megalosiphon* PI 555536; *Nicotiana nudicaulis* PI 555540; *Nicotiana paniculata* PI 555545; *Nicotiana plumbaginifolia* PI 555548; *Nicotiana repanda* PI 555552; *Nicotiana rustica; Nicotiana suaveolens* PI 230960; *Nicotiana sylvestris* PI 555569; *Nicotiana tomentosa* PI 266379; *Nicotiana tomentosiformis*; and *Nicotiana trigonophylla* PI 555572.

In some aspects, the present disclosure provides tobacco plants, or part thereof, comprising a mutation in Nic1 locus, a mutation in Nic2 locus, or both, wherein the tobacco plant is capable of producing leaves having a USDA grade index value of 50 or more. In some aspects, tobacco plants disclosed herein are capable of producing leaves having a USDA grade index value selected from the group consisting of 55 or more, 60 or more, 65 or more, 70 or more, 75 or more, 80 or more, 85 or more, 90 or more, and 95 or more. In other aspects, tobacco plants disclosed herein are capable of producing leaves having a USDA grade index value comparable to that of a control plant when grown in similar growth conditions, wherein the control plant shares an essentially identical genetic background with the tobacco plant except the mutation. In further aspects, tobacco plants disclosed herein are capable of producing leaves having a USDA grade index value of at least about 65%, at least about 70%, at least about 75%, at least about 80%, at least about 85%, at least about 90%, at least about 95%, or at least about 98% of the USDA grade index value of a control plant when grown in similar growth conditions, wherein the control plant shares an essentially identical genetic background with the tobacco plant except the mutation. In further aspects, tobacco plants disclosed herein are capable of producing leaves having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of the control plant. In further aspects, tobacco plants disclosed herein are capable of producing leaves having a USDA grade index value of between 70% and 125%, between 75% and 120%, between 80% and 115%, between 85% and 110%, or between 90% and 100% of the USDA grade index value of the control plant. In some aspects, tobacco plants disclosed herein comprise nicotine at a level below 1%, below 2%, below 5%, below 8%, below 10%, below 12%, below 15%, below 20%, below 25%, below 30%, below 40%, below 50%, below 60%, below 70%, or below 80% of the nicotine level of a control plant when grown in similar growth conditions, wherein the control plant shares an essentially identical genetic background with the tobacco plant except the mutation. In other aspects, tobacco plants disclosed herein comprise a nicotine level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, and less than 0.05%. In further aspects, tobacco plants disclosed herein further comprises a transgene or mutation directly suppressing the expression or activity of one or more genes encoding a product selected from the group consisting of PMT, MPO, QPT, BBL, A622, and MATE transporter.

In some aspects, the present disclosure provides tobacco plants, or part thereof, comprising a mutation in Nic1 locus, a mutation in Nic2 locus, or both, wherein the tobacco plant is capable of producing leaves having a USDA grade index value comparable to that of a control plant when grown in similar growth conditions, wherein the control plant shares an essentially identical genetic background with the tobacco plant except the mutation. In other aspects, tobacco plants disclosed herein are capable of producing leaves having a USDA grade index value selected from the group consisting of 55 or more, 60 or more, 65 or more, 70 or more, 75 or more, 80 or more, 85 or more, 90 or more, and 95 or more. In other aspects, tobacco plants disclosed herein are capable of producing leaves having a USDA grade index value selected from the group consisting of between 50 and 95, between 55 and 95, between 60 and 95, between 65 and 95, between 70 and 95, between 75 and 95, between 80 and 95, between 85 and 95, between 90 and 95, between 55 and 90, between 60 and 85, between 65 and 80, between 70 and 75, between 50 and 55, between 55 and 60, between 60 and 65, between 65 and 70, between 70 and 75, between 75 and 80, between 80 and 85, between 85 and 90, and between 90 and 95. In further aspects, tobacco plants disclosed herein are capable of producing leaves having a USDA grade index value of at least about 65%, at least about 70%, at least about 75%, at least about 80%, at least about 85%, at least about 90%, at least about 95%, or at least about 98% of the USDA grade index value of the control plant. In further aspects, tobacco plants disclosed herein are capable of producing leaves having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of the control plant. In further aspects, tobacco plants disclosed herein are capable of producing leaves having a USDA grade index value of between 70% and 125%, between 75% and 120%, between 80% and 115%, between 85% and 110%, or between 90% and 100% of the USDA grade index value of the control plant. In other aspects, tobacco plants disclosed herein comprise nicotine at a level below 1%, below 2%, below 5%, below 8%, below 10%, below 12%, below 15%, below 20%, below 25%, below 30%, below 40%, below 50%, below 60%, below 70%, or below 80% of the nicotine level of the control plant when grown in similar growth conditions. In other aspects, tobacco plants disclosed herein further comprises a transgene or mutation directly suppressing the expression or activity of one or more genes encoding a product selected from the group consisting of PMT, MPO, QPT, BBL, A622, and MATE transporter.

In some aspects, the present disclosure also provides a tobacco variety, cultivar, or line comprising a mutation selected from the group consisting of a nic1 mutation, a nic2 mutation, and a combination thereof, wherein the tobacco variety, cultivar, or line has a leaf grade comparable to the leaf grade of a control tobacco variety, cultivar, or line when grown in similar growth conditions, wherein the control tobacco variety shares an essentially identical genetic background with the tobacco variety, cultivar, or line except the mutation.

In some aspects, the present disclosure further provides non-transgenic tobacco plants, or part thereof, comprising a nicotine level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, and less than 0.05%, wherein the tobacco plants are capable of producing leaves having a USDA grade index value of 50 or more 55 or more, 60 or more, 65 or more, 70 or more, 75 or more, 80 or more, 85 or more, 90 or more, and 95 or more. In other aspects, such non-transgenic tobacco plants comprise a nicotine level of less than 2.0% and are capable of producing leaves having a USDA grade index value of 70 or more. In furthers aspects, such non-transgenic tobacco plants comprise a nicotine level of less than 1.0% and are capable of producing leaves having a USDA grade index value of 70 or more.

In some aspects, the present disclosure also provides a tobacco plant, or part thereof, comprising a non-transgenic mutation, wherein the non-transgenic mutation reduces the nicotine level of the tobacco plant to below 1%, below 2%, below 5%, below 8%, below 10%, below 12%, below 15%, below 20%, below 25%, below 30%, below 40%, below 50%, below 60%, below 70%, or below 80% of the nicotine level of a control plant when grown in similar growth conditions, wherein the tobacco plant is capable of producing leaves having a USDA grade index value comparable to the USDA grade index value of the control plant, and wherein the control plant shares an essentially identical genetic background with the tobacco plant except the non-transgenic mutation.

In some aspects, the present disclosure provides tobacco plants, or part thereof, comprising a mutation in Nic1 locus, wherein the mutation is absent from LA Burley 21. In some aspects, tobacco plants provided herein comprise a shorter chromosome deletion at Nic1 locus compared to LA Burley 21. In other aspects, tobacco plants provided herein comprise no deletion of a complete gene or a complete genic coding sequence in Nic1 locus. In some aspects, tobacco plants provided herein are homozygous at Nic1 locus. In other aspects, tobacco plants provided herein are heterozygous at Nic1 locus. In some aspects, tobacco plants provided herein comprise a Nic1 mutation selected from the group consisting of a point mutation, a deletion, an insertion, a duplication, and an inversion. In some aspects, Nic1 mutations in the tobacco plants provided herein are introduced by an approach selected from the group consisting of random mutagenesis and targeted mutagenesis. In other aspects, Nic1 mutations in the tobacco plants provided herein are introduced by a targeted mutagenesis approach selected from the group consisting of meganuclease, zinc finger nuclease, TALEN, and CRISPR.

In some aspects, tobacco plants provided herein comprise one or more mutations within one or more genes comprising a sequence having at least 80%, at least 85%, at least 90%, at least 95%, at least 97%, at least 98%, at least 99%, or 100% identity to a sequence selected from the group consisting of SEQ ID NOs: 9 to 28, 75 to 82, 86 to 100, 145, and fragments thereof. In some aspects, one or more mutations reduce the expression or activity of one or more genes comprising a sequence having at least 80%, at least 85%, at least 90%, at least 95%, at least 97%, at least 98%, at least 99%, or 100% identity to a sequence selected from the group consisting of SEQ ID NOs: 9 to 28, 75 to 82, 86 to 100, 145, and fragments thereof.

In some aspects, tobacco plants provided herein comprise one or more mutations within one or more genes comprising a coding sequence having at least 80%, at least 85%, at least 90%, at least 95%, at least 97%, at least 98%, at least 99%, or 100% identity to a sequence selected from the group consisting of SEQ ID NOs: 29 to 48, 83, 101 to 115, 146, and fragments thereof. In some aspects, one or more mutations reduce the expression or activity of one or more genes comprising a coding sequence having at least 80%, at least 85%, at least 90%, at least 95%, at least 97%, at least 98%, at least 99%, or 100% identity to a sequence selected from the group consisting of SEQ ID NOs: 29 to 48, 83, 101 to 115, 146, and fragments thereof.

In some aspects, tobacco plants provided herein comprise one or more mutations within one or more genes encoding a polypeptide having at least 80%, at least 85%, at least 90%, at least 95%, at least 97%, at least 98%, at least 99%, or 100% identity to a sequence selected from the group consisting of SEQ ID NOs: 49 to 68, 84, 116 to 130, 147 and fragments thereof. In some aspects, one or more mutations reduce the expression or activity of one or more genes encoding a polypeptide having at least 80%, at least 85%, at least 90%, at least 95%, at least 97%, at least 98%, at least 99%, or 100% identity to a sequence selected from the group consisting of SEQ ID NOs: 49 to 68, 84, 116 to 130, 147 and fragments thereof.

In some aspects, tobacco plants provided herein comprise one or more mutations within one or more genes comprising a sequence having at least 80%, at least 85%, at least 90%, at least 95%, at least 97%, at least 98%, at least 99%, or 100% identity to a sequence selected from the group consisting of SEQ ID NOs: 13, 28, 33, 48, 82, 86, 87, 101, 102, 145, and 146, and fragments thereof. In some aspects, one or more mutations reduce the expression or activity of one or more genes comprising a sequence having at least 80%, at least 85%, at least 90%, at least 95%, at least 97%, at least 98%, at least 99%, or 100% identity to a sequence selected from the group consisting of SEQ ID NOs: 13, 28, 33, 48, 82, 86, 87, 101, 102, 145, and 146, and fragments thereof.

In some aspects, tobacco plants provided herein comprise one or more mutations within one or more genes comprising a coding sequence having at least 80%, at least 85%, at least 90%, at least 95%, at least 97%, at least 98%, at least 99%, or 100% identity to a sequence selected from the group consisting of SEQ ID NOs: 33, 48, 101, 102, and 146, and fragments thereof. In some aspects, one or more mutations reduce the expression or activity of one or more genes comprising a coding sequence having at least 80%, at least 85%, at least 90%, at least 95%, at least 97%, at least 98%, at least 99%, or 100% identity to a sequence selected from the group consisting of SEQ ID NOs: 33, 48, 101, 102, and 146, and fragments thereof.

In some aspects, tobacco plants provided herein comprise one or more mutations within one or more genes encoding a polypeptide having at least 80%, at least 85%, at least 90%, at least 95%, at least 97%, at least 98%, at least 99%, or 100% identity to a sequence selected from the group consisting of SEQ ID NOs: 53, 68, 116, 117, and 147, and fragments thereof. In some aspects, one or more mutations reduce the expression or activity of one or more genes encoding a polypeptide having at least 80%, at least 85%, at least 90%, at least 95%, at least 97%, at least 98%, at least 99%, or 100% identity to a sequence selected from the group consisting of SEQ ID NOs: 53, 68, 116, 117, and 147, and fragments thereof.

LA Burley 21 is a low total alkaloid tobacco line produced by incorporation of a low alkaloid gene(s) from a Cuban cigar variety into Burley 21 through several backcrosses (Legg et al. 1970). It has approximately 0.2% total alkaloids (dry weight) compared to the about 3.5% (dry weight) of its parent, Burley 21. LA BU21 has a leaf grade well below commercially acceptable standards.

Unless specified otherwise, measurements of alkaloid or nicotine levels or leaf grade index values mentioned herein for a tobacco plant, variety, cultivar, or line refer to average measurements, including, for example, an average of multiple leaves of a single plant or an average measurement from a population of tobacco plants from a single variety, cultivar, or line. A population of tobacco plants or a collection of tobacco leaves for determining an average measurement (e.g., alkaloid or nicotine level or leaf grading) can be of any size, for example, 5, 10, 15, 20, 25, 30, 35, 40, or 50. Industry-accepted standard protocols are followed for determining average measurements or grad index values.

As used herein, "similar growth conditions" refer to similar environmental conditions and/or agronomic practices for growing and making meaningful comparisons between two or more plant genotypes so that neither environmental conditions nor agronomic practices would contribute to or explain any difference observed between the two or more plant genotypes. Environmental conditions include, for example, light, temperature, water (humidity), and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp 70-103.

"Alkaloids" are complex, nitrogen-containing compounds that naturally occur in plants, and have pharmacological effects in humans and animals. "Nicotine" is the primary natural alkaloid in commercialized cigarette tobacco and accounts for about 90 percent of the alkaloid content in *Nicotiana tabacum*. Other major alkaloids in tobacco include cotinine, nornicotine, myosmine, nicotyrine, anabasine and anatabine. Minor tobacco alkaloids include nicotine-n-oxide, N-methyl anatabine, N-methyl anabasine, pseudooxynicotine, 2,3 dipyridyl and others.

In some aspects, tobacco plants provided herein comprise a lower level of total alkaloid or an individual alkaloid compared to a control tobacco plant without a Nic1 mutation when grown in similar growth conditions. In other aspects, tobacco plants provided herein comprise a lower level of one or more alkaloids selected from the group consisting of cotinine, nornicotine, myosmine, nicotyrine, anabasine and anatabine, compared to a control tobacco plant when grown in similar growth conditions. In some aspects, a lower alkaloid level refers to an alkaloid level of below 1%, below 2%, below 5%, below 8%, below 10%, below 12%, below 15%, below 20%, below 25%, below 30%, below 40%, below 50%, below 60%, below 70%, or below 80% of the alkaloid level of a control tobacco plant. In other aspects, a lower alkaloid level refers to an alkaloid level of about between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, between 19% and 20%, between 21% and 22%, between 22% and 23%, between 23% and 24%, between 24% and 25%, between 25% and 26%, between 26% and 27%, between 27% and 28%, between 28% and 29%, or between 29% and 30% of the alkaloid level of a control tobacco plant. In further aspects, a lower alkaloid level refers to an alkaloid level of about between 0.5% and 5%, between 5% and 10%, between 10% and 20%, between 20% and 30% of the alkaloid level of a control tobacco plant.

Alkaloid levels can be assayed by methods known in the art, for example by quantification based on gas-liquid chromatography, high performance liquid chromatography, radio-immunoassays, and enzyme-linked immunosorbent assays. For example, nicotinic alkaloid levels can be measured by a GC-FID method based on CORESTA Recommended Method No. 7, 1987 and ISO Standards (ISO TC 126N 394 E. See also Hibi et al., *Plant Physiology* 100: 826-35 (1992) for a method using gas-liquid chromatography equipped with a capillary column and an FID detector.

Alternatively, tobacco total alkaloids can be measured using a segmented-flow colorimetric method developed for analysis of tobacco samples as adapted by Skalar Instrument Co (West Chester, Pa.) and described by Collins et al., *Tobacco Science* 13:79-81 (1969). In short, samples of tobacco are dried, ground, and extracted prior to analysis of total alkaloids and reducing sugars. The method then employs an acetic acid/methanol/water extraction and charcoal for decolorization. Determination of total alkaloids was based on the reaction of cyanogen chloride with nicotine alkaloids in the presence of an aromatic amine to form a colored complex which is measured at 460 nm. Unless specified otherwise, total alkaloid levels or nicotine levels shown herein are on a dry weight basis (e.g., percent total alkaloid or percent nicotine).

In some aspects, tobacco plants provided herein comprise a lower level of nicotine compared to a control tobacco plant without a Nic1 mutation when grown in similar growth conditions. In some aspects, a lower nicotine level refers to an average nicotine level of below 1%, below 2%, below 5%, below 8%, below 10%, below 12%, below 15%, below 20%, below 25%, below 30%, below 40%, below 50%, below 60%, below 70%, or below 80% of the average nicotine level of a control tobacco plant. In other aspects, a lower nicotine level refers to an average nicotine level of about between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, between 19% and 20%, between 21% and 22%, between 22% and 23%, between 23% and 24%, between 24% and 25%, between 25% and 26%, between 26% and 27%, between 27% and 28%, between 28% and 29%, or between 29% and 30% of the average nicotine level of a control tobacco plant. In further aspects, a lower nicotine level refers to an average nicotine level of about between 0.5% and 5%, between 5% and 10%, between 10% and 20%, between 20% and 30% of the average nicotine level of a control tobacco plant.

In some aspects, tobacco plants provided herein comprise an average nicotine level selected from the group consisting of about 0.01%, 0.02%, 0.05%, 0.75%, 0.1%, 0.15%, 0.2%, 0.3%, 0.35%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, and 9% on a dry weight basis. In other aspects, tobacco plants provided herein comprise an average nicotine level selected from the group consisting of about between 0.01% and 0.02%, between 0.02% and 0.05%, between 0.05% and 0.75%, between 0.75% and 0.1%, between 0.1% and 0.15%, between 0.15% and 0.2%, between 0.2% and 0.3%, between 0.3% and 0.35%, between 0.35% and 0.4%, between 0.4% and 0.5%, between 0.5% and 0.6%, between 0.6% and 0.7%, between 0.7% and 0.8%, between 0.8% and 0.9%, between 0.9% and 1%, between 1% and 1.1%, between 1.1% and 1.2%, between 1.2% and 1.3%, between 1.3% and 1.4%, between 1.4% and 1.5%, between 1.5% and 1.6%, between 1.6% and 1.7%, between 1.7% and 1.8%, between 1.8% and 1.9%, between 1.9% and 2%, between 2% and 2.1%, between 2.1% and 2.2%, between 2.2% and 2.3%, between 2.3% and 2.4%, between 2.4% and 2.5%, between 2.5% and 2.6%, between 2.6% and 2.7%, between 2.7% and 2.8%, between 2.8% and 2.9%, between 2.9% and 3%, between 3% and 3.1%, between 3.1% and 3.2%, between 3.2% and 3.3%, between 3.3% and 3.4%, between 3.4% and 3.5%, and between 3.5% and 3.6% on a dry weight basis. In further aspects, tobacco plants provided herein comprise an average nicotine level selected from the group consisting of about between 0.01% and 0.1%, between 0.02% and 0.2%, between 0.03% and 0.3%, between 0.04% and 0.4%, between 0.05% and 0.5%, between 0.75% and 1%, between 0.1% and 1.5%, between 0.15% and 2%, between 0.2% and 3%, and between 0.3% and 3.5% on a dry weight basis.

The present disclosure also provides tobacco plants having altered nicotine levels without negative impacts over other tobacco traits, e.g., leaf grade index value. In one aspect, a low-nicotine or nicotine-free tobacco variety disclosed herein provides cured tobacco of commercially acceptable grade. Tobacco grades are evaluated based on factors including, but not limited to, the leaf stalk position, leaf size, leaf color, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast. Leaf grade can be determined, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida Shade-Grown Cigar-Wrapper Tobacco (U.S. Type 62), Effective April 1971. A USDA grade index value can be determined according to an industry accepted grade index. See, e.g., Bowman et al, *Tobacco Science,* 32:39-40(1988); Legacy Tobacco Document Library (Bates Document #523267826-523267833, Jul. 1, 1988, Memorandum on the Proposed Burley Tobacco Grade Index); and Miller et al., 1990, *Tobacco Intern.,* 192:55-57 (all foregoing references are incorporated by inference in their entirety). In one aspect, a USDA grade index is a 0-100 numerical representation of federal grade received and is a weighted average of all stalk positions. A higher grade index indicates higher quality. Alternatively, leaf grade can be determined via hyper-spectral imaging. See e.g., WO 2011/027315 (published on Mar. 10, 2011, and incorporated by inference in its entirety).

In some aspects, tobacco plants provided herein comprise a similar level of one or more tobacco aroma compounds selected from the group consisting of 3-methylvaleric acid, valeric acid, isovaleric acid, a labdenoid, a cembrenoid, a sugar ester, and a reducing sugar, compared to control tobacco plants when grown in similar growth conditions. In other aspects, tobacco plants provided herein comprise a Nic1 mutation, a Nic2 mutation, or a combination thereof having no impact over the level of one or more tobacco aroma compounds selected from the group consisting of 3-methylvaleric acid, valeric acid, isovaleric acid, a labdenoid, a cembrenoid, a sugar ester, and a reducing sugar.

As used herein, tobacco aroma compounds are compounds associated with the flavor and aroma of tobacco smoke. These compounds include, but are not limited to, 3-methylvaleric acid, valeric acid, isovaleric acid, cembrenoid and labdenoid diterpenes, and sugar esters. Concentrations of tobacco aroma compounds can be measured by any known metabolite profiling methods in the art including, without limitation, gas chromatography mass spectrometry (GC-MS), Nuclear Magnetic Resonance Spectroscopy, liquid chromatography-linked mass spectrometry. See The Handbook of Plant Metabolomics, edited by Weckwerth and Kahl, (Wiley-Blackwell) (May 28, 2013).

As used herein, "reducing sugar(s)" are any sugar (monosaccharide or polysaccharide) that has a free or potentially free aldehyde or ketone group. Glucose and fructose act as nicotine buffers in cigarette smoke by reducing smoke pH and effectively reducing the amount of "free" unprotonated nicotine. Reducing sugars balances smoke flavor, for example, by modifying the sensory impact of nicotine and other tobacco alkaloids. An inverse relationship between sugar content and alkaloid content has been reported across tobacco varieties, within the same variety, and within the same plant line caused by planting conditions. Reducing sugar levels can be measured using a segmented-flow colorimetric method developed for analysis of tobacco samples as adapted by Skalar Instrument Co (West Chester, Pa.) and described by Davis, *Tobacco Science* 20:139-144 (1976). For example, a sample is dialyzed against a sodium carbonate solution. Copper neocuproin is added to the sample and the solution is heated. The copper neocuproin chelate is reduced in the presence of sugars resulting in a colored complex which is measured at 460 nm.

In some aspects, tobacco plants provided herein comprise one or more non-naturally existing mutant alleles at Nic1 or Nic2 locus which reduce or eliminate one or more gene activity from Nic1 or Nic2 locus. In some aspects, these mutant alleles result in lower nicotine levels. Mutant Nic1 or Nic2 alleles can be introduced by any method known in the art including random or targeted mutagenesis approaches.

Such mutagenesis methods include, without limitation, treatment of seeds with ethyl methylsulfate (EMS) (Hildering and Verkerk, In, The use of induced mutations in plant breeding. Pergamon press, pp 317-320, 1965) or UV-irradiation, X-rays, and fast neutron irradiation (see, for example, Verkerk, *Neth. J. Agric. Sci.* 19:197-203, 1971; and Poehlman, Breeding Field Crops, Van Nostrand Reinhold, New York (3.sup.rd ed), 1987), transposon tagging (Fedoroff et al., 1984; U.S. Pat. Nos. 4,732,856 and 5,013,658), as well as T-DNA insertion methodologies (Hoekema et al., 1983; U.S. Pat. No. 5,149,645). EMS-induced mutagenesis consists of chemically inducing random point mutations over the length of the genome. Fast neutron mutagenesis consists of exposing seeds to neutron bombardment which causes large deletions through double stranded DNA breakage. Transposon tagging comprises inserting a transposon within an endogenous gene to reduce or eliminate expression of the gene. The types of mutations that may be present in a tobacco gene include, for example, point mutations, deletions, insertions, duplications, and inversions. Such mutations desirably are present in the coding region of a tobacco gene; however mutations in the promoter region, and intron, or an untranslated region of a tobacco gene may also be desirable.

In addition, a fast and automatable method for screening for chemically induced mutations, TILLING (Targeting Induced Local Lesions In Genomes), using denaturing HPLC or selective endonuclease digestion of selected PCR products is also applicable to the present disclosure. See, McCallum et al. (2000) *Nat. Biotechnol.* 18:455-457. Mutations that impact gene expression or that interfere with the function of genes disclosed herein can be determined using methods that are well known in the art. Insertional mutations in gene exons usually result in null-mutants. Mutations in conserved residues can be particularly effective in inhibiting the function of a protein. In some aspects, tobacco plants disclosed herein comprise a nonsense (e.g., stop codon) mutation is one or more Nic1 genes described herein.

Is some aspects, the present disclosure also provides tobacco lines with altered nicotine levels while maintaining commercially acceptable leaf quality. These lines can be produced by introducing mutations into one or more genes at Nic1 or Nic2 locus via precise genome engineering technologies, for example, Transcription activator-like effector nucleases (TALENs), meganuclease, zinc finger nuclease, and CRISPR-cas9 system. See, e.g., Gaj et al., *Trends in Biotechnology,* 31(7):397-405 (2013).

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

The present disclosure also provides compositions and methods for inhibiting the expression or function of one or more polypeptides from Nic1 locus in a plant, particularly plants of the *Nicotiana* genus, including tobacco plants of the various commercial varieties.

In some aspects, the present disclosure provides tobacco plants, or part thereof, comprising a heterologous expression cassette comprising a Nic1 inhibitory sequence of a gene comprising a sequence having at least 80%, at least 85%, at least 90%, at least 95%, at least 97%, at least 98%, at least 99%, or 100% identity to a sequence selected from the group consisting of SEQ ID NOs: 9 to 28, 75 to 82, 86 to 100, 145, and fragments thereof, wherein the inhibitory sequence is operably linked to a promoter that is functional in a plant cell, and wherein the inhibitory sequence has at least 90% sequence identity to a fragment of at least 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides of the sequence having at least 80%, at least 85%, at least 90%, at least 95%, at least 97%, at least 98%, at least 99%, or 100% identity to a sequence selected from the group consisting of SEQ ID NOs: 9 to 28, 75 to 82, 86 to 100, 145, and fragments thereof. In other aspects, the present disclosure provides tobacco plants, or part thereof, comprising a heterologous expression cassette comprising a Nic1 inhibitory sequence of a gene comprising a sequence having at least 80%, at least 85%, at least 90%, at least 95%, at least 97%, at least 98%, at least 99%, or 100% identity to a sequence selected from the group consisting of SEQ ID NOs: 13, 28, 33, 48, 82, 86, 87, 101, 102, 145, and 146, and fragments thereof, wherein the inhibitory sequence is operably linked to a promoter that is functional in a plant cell, and wherein the inhibitory sequence has at least 90% sequence identity to a fragment of at least 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides of the sequence having at least 80%, at least 85%, at least 90%, at least 95%, at least 97%, at least 98%, at least 99%, or 100% identity to a sequence selected from the group consisting of SEQ ID NOs: 13, 28, 33, 48, 82, 86, 87, 101, 102, 145, and 146, and fragments thereof. In some aspects, a Nic1 inhibitory sequence is capable of being transcribed as an inhibitory polynucleotide selected from the group consisting of a single-stranded RNA polynucleotide, a double-stranded RNA polynucleotide, and a combination thereof.

As used herein, the terms "inhibit," "inhibition," and "inhibiting" are defined as any method known in the art or described herein that decreases the expression or function of a gene product of interest (e.g., a target gene product). "Inhibition" can be in the context of a comparison between two plants, for example, a genetically altered plant versus a wild-type plant. Alternatively, inhibition of expression or function of a target gene product can be in the context of a comparison between plant cells, organelles, organs, tissues, or plant parts within the same plant or between different plants, and includes comparisons between developmental or temporal stages within the same plant or plant part or between plants or plant parts. "Inhibition" includes any relative decrement of function or production of a gene product of interest, up to and including complete elimination of function or production of that gene product. The term "inhibition" encompasses any method or composition that down-regulates translation and/or transcription of the target gene product or functional activity of the target gene product. In some aspects, the mRNA or protein level of one or more genes from Nic1 locus in a modified plant disclosed herein is less than 95%, less than 90%, less than 80%, less than 70%, less than 60%, less than 50%, less than 40%, less than 30%, less than 20%, less than 10%, less than 5%, less than 4%, less than 3%, less than 2%, or less than 1% of the protein level of the same gene in a plant that is not a mutant or that has not been genetically modified to inhibit the expression of that gene.

The term "inhibitory sequence" encompasses any polynucleotide or polypeptide sequence capable of inhibiting the expression or function of a gene involved in nicotine biosynthesis regulation from Nic1 locus in a plant, such as full-length polynucleotide or polypeptide sequences, truncated polynucleotide or polypeptide sequences, fragments of polynucleotide or polypeptide sequences, variants of polynucleotide or polypeptide sequences, sense-oriented nucleotide sequences, antisense-oriented nucleotide sequences, the complement of a sense- or antisense-oriented nucleotide sequence, inverted regions of nucleotide sequences, hairpins of nucleotide sequences, double-stranded nucleotide sequences, single-stranded nucleotide sequences, combinations thereof, and the like. The term "polynucleotide sequence" includes sequences of RNA, DNA, chemically modified nucleic acids, nucleic acid analogs, combinations thereof, and the like.

Inhibitory sequences are designated herein by the name of the target gene product. Thus, a "Nic1 inhibitory sequence" refers to an inhibitory sequence that is capable of inhibiting the expression of a gene involved in nicotine biosynthesis regulation from Nic1 locus in a plant, for example, at the level of transcription and/or translation, or which is capable of inhibiting the function of a gene product. When the phrase "capable of inhibiting" is used in the context of a polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (e.g., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (e.g., inhibits expression or function of the target gene product).

A Nic1 inhibitory sequence disclosed herein can be a sequence triggering gene silencing via any silencing pathway or mechanism known in the art, including, but not limited to, sense suppression/cosuppression, antisense suppression, double-stranded RNA (dsRNA) interference, hairpin RNA interference and intron-containing hairpin RNA interference, amplicon-mediated interference, ribozymes, small interfering RNA, artificial or synthetic microRNA, and artificial trans-acting siRNA. A Nic1 inhibitory sequence may range from at least about 20 nucleotides, about 50 nucleotides, about 70 nucleotides, about 100 nucleotides, about 150 nucleotides, about 200 nucleotides, about 250 nucleotides, about 300 nucleotides, about 350 nucleotides, about 400 nucleotides, and up to the full-length polynucleotide encoding the proteins of the present disclosure, depending upon the desired outcome. In one aspect, a Nic1 inhibitory sequence can be a fragment of between about 50 and about 400 nucleotides, between about 70 and about 350 nucleotides, between about 90 and about 325 nucleotides, between about 90 and about 300 nucleotides, between about 90 and about 275 nucleotides, between about 100 and about 400 nucleotides, between about 100 and about 350 nucleotides, between about 100 and about 325 nucleotides, between about 100 and about 300 nucleotides, between about 125 and about 300 nucleotides, or between about 125 and about 275 nucleotides in length. In some embodiments, a fragment of a cytochrome P450 polynucleotide is about 50, about 60, about 70, about 80, about 90, about 100, about 125, about 150, about 175, about 200, about 225, about 250, about 275, about 300, about 325, about 350, about 400 nucleotides in length, and other such values between about 70 and about 400 nucleotides.

The use of the term "polynucleotide" is not intended to limit the present disclosure to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

In some aspects, the present disclosure provides recombinant DNA constructs comprising a promoter that is functional in a tobacco cell and operably linked to a polynucleotide that encodes an RNA molecule capable of binding to an RNA encoding a polypeptide having an amino acid sequence at least 80%, at least 85%, at least 90%, at least 95%, at least 97%, at least 98%, at least 99% identical to an amino acid sequence selected from the group consisting of SEQ ID NOs: 49 to 68, 84, 116 to 130, 147, and fragments thereof, and wherein the RNA molecule suppresses the expression of the polypeptide. In some aspects, the RNA molecule is selected from the group consisting of a microRNA, an siRNA, and a trans-acting siRNA. In other aspects, the recombinant DNA construct encodes a double stranded RNA. Also provided are transgenic tobacco plants or part thereof, cured tobacco material, or tobacco products comprising these recombinant DNA constructs. In some aspects, these transgenic plants, cured tobacco material, or tobacco products comprise a lower level of nicotine compared to a control tobacco plant without the recombinant DNA construct. Further provided are methods of reducing the nicotine level of a tobacco plant, the method comprising transforming a tobacco plant with any of these recombinant DNA constructs.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous.

As used herein and when used in reference to a sequence, "heterologous" refers to a sequence that originates from a foreign species, or, if from the same species, is substantially modified from its native form in composition and/or genomic locus by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a foreign species, or, if from the same species, is substantially modified from its native form in composition and/or genomic locus by deliberate human intervention.

Heterologous nucleic acid constructs include, but are not limited to, recombinant nucleotide constructs that have been introduced into a plant or plant part thereof, for example, via transformation methods or subsequent breeding of a transgenic plant with another plant of interest.

As used herein, "gene expression" refers to the biosynthesis or production of a gene product, including the transcription and/or translation of the gene product.

Also provided herein are compositions and methods for overexpressing one or more polypeptides from Nic1 locus in a plant, particularly plants of the *Nicotiana* genus, including tobacco plants of the various commercial varieties.

In some aspects, the present disclosure provides recombinant DNA constructs comprising a promoter that is functional in a tobacco cell and operably linked to a polynucleotide that encodes a polypeptide having an amino acid sequence at least 80%, at least 85%, at least 90%, at least 95%, at least 97%, at least 98%, at least 99%, or 100% identical to an amino acid sequence selected from the group consisting of SEQ ID NOs: 49 to 68, 84, 116 to 130, 147, and fragments thereof. Also provided are transgenic tobacco plants or part thereof, cured tobacco material, or tobacco products comprising these recombinant DNA constructs. In some aspects, these transgenic plants, cured tobacco material, or tobacco products comprise an increased level of nicotine compared to a control tobacco plant without the recombinant DNA construct. Further provided are methods of increasing the nicotine level of a tobacco plant, the method comprising transforming a tobacco plant with any of these recombinant DNA constructs.

In some aspects, recombinant DNA constructs or expression cassettes disclosed herein can also comprise a selectable marker gene for the selection of transgenic cells. Selectable marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP).

In some aspects, recombinant DNA constructs or expression cassettes disclosed herein comprise a promoter selected from the group consisting of a constitutive promoter, an inducible promoter, and a tissue-preferred promoter (for example, a leaf-specific or root-specific promoter). Exemplary constitutive promoters include the core promoter of the Rsyn7 promoter and other constitutive promoters disclosed in U.S. Pat. No. 6,072,050; the core CaMV 35S promoter (Odell et al. (1985) Nature 313:810-812); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J 3:2723-2730); ALS promoter (U.S. Pat. No. 5,659,026), and the like. Exemplary chemical-inducible promoters include the tobacco PR-1a promoter, which is activated by salicylic acid. Other chemical-inducible promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2): 247-257) and tetracycline-inducible promoters (see, for example, Gatz et al. (1991) Mol. Gen. Genet. 227:229-237, and U.S. Pat. Nos. 5,814,618 and 5,789,156). Additional exemplary promoters that can be used herein are those responsible for heat-regulated gene expression, light-regulated gene expression (for example, the pea rbcS-3A; the maize rbcS promoter; the chlorophyll alb-binding protein gene found in pea; or the Arabssu promoter), hormone-regulated gene expression (for example, the abscisic acid (ABA) responsive sequences from the Em gene of wheat; the ABA-inducible HVA1 and HVA22, and rd29A promoters of barley and *Arabidopsis*; and wound-induced gene expression (for example, of wunl), organ specific gene expression (for example, of the tuber-specific storage protein gene; the 23-kDa zein gene from maize described by; or the French bean (β-phaseolin gene), or pathogen-inducible promoters (for example, the PR-1, prp-1, or (β-1,3 glucanase promoters, the fungal-inducible wirla promoter of wheat, and the nematode-inducible promoters, TobRB7-5A and Hmg-1, of tobacco arid parsley, respectively).

In some aspects, tobacco plants provided herein further comprise increased or reduced expression of activity of genes involved in nicotine biosynthesis or transport. Genes involved in nicotine biosynthesis include, but are not limited to, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), and S-adenosyl-methionine synthetase (SAMS). Nicotine Synthase, which catalyzes the condensation step between a nicotinic acid derivative and methylpyrrolinium cation, has not been elucidated although two candidate genes (A622 and NBB1) have been proposed. See US 2007/0240728 A1 and US 2008/0120737A1. A622 encodes an isoflavone reductase-like protein. In addition, several transporters may be involved in the translocation of nicotine. A transporter gene, named MATE, has been cloned and characterized (Morita et al., *PNAS* 106:2447-52 (2009)).

In some aspects, tobacco plants provided herein further comprise an increased or reduced level of mRNA, protein, or both of one or more genes encoding a product selected from the group consisting of PMT, MPO, QPT, ADC, ODC, PRAI, SAMS, BBL, MATE, A622, and NBB1, compared to a control tobacco plant. In other aspects, tobacco plants provided herein further comprise a transgene directly suppressing the expression of one or more genes encoding a product selected from the group consisting of PMT, MPO, QPT, ADC, ODC, PRAI, SAMS, BBL, MATE, A622, and NBB1. In other aspects, tobacco plants provided herein further comprise a transgene or mutation suppressing the expression or activity of one or more genes encoding a product selected from the group consisting of PMT, MPO, QPT, ADC, ODC, PRAI, SAMS, BBL, MATE, A622, and NBB1. In other aspects, tobacco plants provided herein further comprise a transgene overexpressing one or more genes encoding a product selected from the group consisting of PMT, MPO, QPT, ADC, ODC, PRAI, SAMS, BBL, MATE, A622, and NBB1.

Also disclosed herein are the transformation of tobacco plants with recombinant constructs or expression cassettes described herein using any suitable transformation methods known in the art. Methods for introducing polynucleotide sequences into tobacco plants are known in the art and include, but are not limited to, stable transformation methods, transient transformation methods, and virus-mediated methods. "Stable transformation" refers to transformation where the nucleotide construct of interest introduced into a plant integrates into the genome of the plant and is capable of being inherited by the progeny thereof "Transient transformation" is intended to mean that a sequence is introduced into the plant and is only temporally expressed or is only transiently present in the plant.

Suitable methods of introducing polynucleotides into plant cells of the present disclosure include microinjection (Crossway et al. (1986) *Biotechniques* 4:320-334), electroporation (Shillito et al. (1987) *Meth. Enzymol.* 153:313-336; Riggs et al. (1986) *Proc. Natl. Acad. Sci. USA* 83:5602-5606), *Agrobacterium*-mediated transformation (U.S. Pat. Nos. 5,104,310, 5,149,645, 5,177,010, 5,231,019, 5,463,174, 5,464,763, 5,469,976, 4,762,785, 5,004,863, 5,159,135, 5,563,055, and 5,981,840), direct gene transfer (Paszkowski et al. (1984) *EMBO J.* 3:2717-2722), and ballistic particle acceleration (see, for example, U.S. Pat. Nos. 4,945,050, 5,141,131, 5,886,244, 5,879,918, and 5,932,782; Tomes et al. (1995) in *Plant Cell, Tissue, and Organ Culture Fundamental Methods*, ed. Gamborg and Phillips (Springer-Verlag, Berlin); McCabe et al. (1988) *Biotechnology* 6:923-926). Also see Weissinger et al. (1988) *Ann. Rev. Genet.* 22:421-477; Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation).

In other aspects, recombinant constructs or expression cassettes disclosed herein may be introduced into plants by contacting plants with a virus or viral nucleic acids. Generally, such methods involve incorporating an expression cassette of the present disclosure within a viral DNA or RNA molecule. It is recognized that promoters for use in the expression cassettes disclosed herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221.

Any plant tissue that can be subsequently propagated using clonal methods, whether by organogenesis or embryogenesis, may be transformed with a recombinant construct or an expression cassette disclosed herein. By "organogenesis" in intended the process by which shoots and roots are developed sequentially from meristematic centers. By "embryogenesis" is intended the process by which shoots and roots develop together in a concerted fashion (not sequentially), whether from somatic cells or gametes. Exemplary tissues that are suitable for various transformation protocols described herein include, but are not limited to, callus tissue, existing meristematic tissue (e.g., apical meristems, axillary buds, and root meristems) and induced meristem tissue (e.g., cotyledon meristem and hypocotyl meristem), hypocotyls, cotyledons, leaf disks, pollen, embryos, and the like.

In some aspects, tobacco plants provided herein are from a tobacco type selected from the group consisting of flue-cured tobacco, air-cured tobacco, dark air-cured tobacco, dark fire-cured tobacco, *Galpao* tobacco, and Oriental tobacco. In other aspects, tobacco plants provided herein are from a tobacco type selected from the group consisting of Burley tobacco, Maryland tobacco, and dark tobacco.

Flue-cured tobaccos (also called Virginia or bright tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the U.S. In some aspects, low-alkaloid or low-nicotine tobacco plants or seeds provided herein are in a flue-cured tobacco background selected from the group consisting of CC 13, CC 27, CC 33, CC 37, CC 65, CC 67, CC 700, GF 318, GL 338, GL 368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, SPEIGHT 236, and any variety essentially derived from any one of the foregoing varieties. In other aspects, low-alkaloid or low-nicotine tobacco plants or seeds provided herein are in a flue-cured tobacco background selected from the group consisting of Coker 48, Coker 176, Coker 371-Gold, Coker 319, Coker 347, GL 939, K 149, K326, K 340, K 346, K 358, K 394, K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116, Va 182, and any variety essentially derived from any one of the foregoing varieties. See WO 2004/041006 A1. In further aspects, low-alkaloid or low-nicotine tobacco plants, seeds, hybrids, varieties, or lines disclosed herein are in any flue cured background selected from the group consisting of K326, K346, and NC196.

Air-cured tobaccos include Burley, Maryland, and dark tobaccos. The common factor is that curing is primarily without artificial sources of heat and humidity. Burley tobaccos are light to dark brown in color, high in oil, and low in sugar. Burley tobaccos are air-cured in barns. Major Burley growing countries are Argentina, Brazil, Italy, Malawi, and the U.S. Maryland tobaccos are extremely fluffy, have good burning properties, low nicotine and a neutral aroma. Major Maryland growing countries include the U.S. and Italy. In some aspects, low-alkaloid or low-nicotine tobacco plants or seeds provided herein are in a Burley tobacco background selected from the group consisting of Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R 711, R 712, NCBH 129, Bu 21×Ky 10, HB04P, Ky 14×L 8, Kt 200, Newton 98, Pedigo 561, Pf561 and Va 509. In further aspects, low-alkaloid or low-nicotine tobacco plants, seeds, hybrids, varieties, or lines disclosed herein are in any Burley background selected from the group consisting of TN 90, KT 209, KT 206, KT212, and HB 4488. In other aspects, low-alkaloid or low-nicotine tobacco plants or seeds provided herein are in a Maryland tobacco background selected from the group consisting of Md 10, Md 40, Md 201, Md 609, Md 872 and Md 341.

Dark air-cured tobaccos are distinguished from other types primarily by its curing process which gives dark air-cured tobacco its medium- to dark-brown color and distinct aroma. Dark air-cured tobaccos are mainly used in the production of chewing tobacco and snuff. In some aspects, low-alkaloid or low-nicotine tobacco plants or seeds provided herein are in a dark air-cured tobacco background selected from the group consisting of Sumatra, Jatim, Dominican Cubano, Besuki, One sucker, Green River, Virginia sun-cured, and Paraguan Passado.

Dark fire-cured tobaccos are generally cured with low-burning wood fires on the floors of closed curing barns. Their leaves have low sugar content but high nicotine content. Dark fire-cured tobaccos are used for making pipe blends, cigarettes, chewing tobacco, snuff and strong-tasting cigars. Major growing regions for dark fire-cured tobaccos are Tennessee, Kentucky, and Virginia, USA. In some aspects, low-alkaloid or low-nicotine tobacco plants or seeds provided herein are in a dark fire-cured tobacco background selected from the group consisting of Narrow Leaf Madole, Improved Madole, Tom Rosson Madole, Newton's VH Madole, Little Crittenden, Green Wood, Little Wood, Small Stalk Black Mammoth, DT 508, DT 518, DT 592, KY 171, DF 911, DF 485, TN D94, TN D950, VA 309, and VA 359.

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant and leaf size, characteristic of today's Oriental varieties, as well as its unique aroma properties are a result of the plant's adaptation to the poor soil and stressful climatic conditions in which it develop over many past centuries. In some aspects, low-alkaloid or low-nicotine tobacco plants or seeds provided herein are in a Oriental tobacco background selected from the group consisting of Izmir, Katerini, Samsun, Basma and Krumovgrad, Trabzon, Thesalian, Tasova, Sinop, Izmit, Hendek, Edirne, Semdinli, Adiyanman, Yayladag, Iskenderun, Duzce, Macedonian, Mavra, Prilep, Bafra, Bursa, Bucak, Bitlis, Balikesir, and any variety essentially derived from any one of the foregoing varieties.

In some aspects, low-alkaloid or low-nicotine tobacco plants, seeds, hybrids, varieties, or lines disclosed herein are essentially derived from or in the genetic background of BU 64, CC 101, CC 200, CC 27, CC 301, CC 400, CC 500, CC 600, CC 700, CC 800, CC 900, Coker 176, Coker 319, Coker 371 Gold, Coker 48, CU 263, DF911, *Galpao* tobacco, GL 26H, GL 350, GL 600, GL 737, GL 939, GL 973, HB 04P, K 149, K 326, K 346, K 358, K394, K 399, K 730, KDH 959, KT 200, KT204LC, KY 10, KY 14, KY 160, KY 17, KY 171, KY 907, KY907LC, KTY14×L8 LC, Little Crittenden, McNair 373, McNair 944, msKY 14×L8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, or VA359, Maryland 609, HB3307PLC, HB4488PLC, KT206LC, KT209LC, KT210LC, KT212LC, R610LC, PVH2310, NC196, KTD14LC, KTD6LC, KTD8LC, PD7302LC, PD7305LC, PD7309LC, PD7318LC, PD7319LC, PD7312LC, ShireyLC, or any commercial tobacco variety according to standard tobacco breeding techniques known in the art.

All foregoing mentioned specific varieties of dark air-cured, Burley, Maryland, dark fire-cured, or Oriental type are only listed for exemplary purposes. Any additional dark air-cured, Burley, Maryland, dark fire-cured, Oriental varieties are also contemplated in the present application.

Also provided herein are populations of tobacco plants described herein. In one aspect, a population of tobacco plants disclosed herein has a planting density of between about 5,000 and about 8000, between about 5,000 and about 7,600, between about 5,000 and about 7,200, between about 5,000 and about 6,800, between about 5,000 and about 6,400, between about 5,000 and about 6,000, between about 5,000 and about 5,600, between about 5,000 and about 5,200, between about 5,200 and about 8,000, between about 5,600 and about 8,000, between about 6,000 and about 8,000, between about 6,400 and about 8,000, between about 6,800 and about 8,000, between about 7,200 and about 8,000, or between about 7,600 and about 8,000 plants per acre. In another aspect, a population of tobacco plants disclosed herein is in a soil type with low to medium fertility.

Also provided herein are containers of seeds from tobacco plants described herein. A container of tobacco seeds of the present disclosure may contain any number, weight, or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Containers of tobacco seeds may be any container available in the art. By way of non-limiting example, a container may be a box, a bag, a packet, a pouch, a tape roll, a tube, or a bottle.

Also provided herein is cured tobacco material made from low-alkaloid or low-nicotine tobacco plants described herein. Further provided is cured tobacco material made from tobacco plants described herein with higher levels of total alkaloid or nicotine.

"Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In some aspects, green leaf tobacco provided herein can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation. Fermentation typically is characterized by high initial moisture content, heat generation, and a 10 to 20% loss of dry weight. See, e.g., U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cure, aged, and fermented tobacco can be further processed (e.g., cut, shredded, expanded, or blended). See, for example, U.S. Pat. Nos. 4,528,993; 4,660,577; and 4,987,907. In one aspect, the cured tobacco material of the present disclosure is sun-cured. In another aspect, the cured tobacco material of the present disclosure is flue-cured, air-cured, or fire-cured.

Tobacco material obtained from the tobacco lines, varieties or hybrids of the present disclosure can be used to make tobacco products. As used herein, "tobacco product" is defined as any product made or derived from tobacco that is intended for human use or consumption.

Tobacco products provided herein include, without limitation, cigarette products (e.g., cigarettes and bidi cigarettes), cigar products (e.g., cigar wrapping tobacco and cigarillos), pipe tobacco products, products derived from tobacco, tobacco-derived nicotine products, smokeless tobacco products (e.g., moist snuff, dry snuff, and chewing tobacco), films, chewables, tabs, shaped parts, gels, consumable units, insoluble matrices, hollow shapes, reconstituted tobacco, expanded tobacco, and the like. See, e.g., U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Tobacco products derived from plants of the present disclosure also include cigarettes and other smoking articles, particularly those smoking articles including filter elements, wherein the rod of smokable material includes cured tobacco within a tobacco blend. In an aspect, a tobacco product of the present disclosure is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the present disclosure is a smokeless tobacco product. Smokeless tobacco products are not combusted and include, but not limited to, chewing tobacco, moist smokeless tobacco, snus, and dry snuff Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally. In a further aspect, a tobacco product of the present disclosure is selected from the group consisting of loose leaf chewing tobacco, plug chewing tobacco, moist snuff, and nasal snuff. In yet another aspect, a tobacco product of the present disclosure is selected from the group consisting of an electronically heated cigarette, an e-cigarette, an electronic vaporing device.

In an aspect, a tobacco product of the present disclosure can be a blended tobacco product. In another aspect, a tobacco product of the present disclosure can be a low nicotine tobacco product. In a further aspect, a tobacco product of the present disclosure may comprise nornicotine at a level of less than about 3 mg/g. For example, the nornicotine content in such a product can be 3.0 mg/g, 2.5 mg/g, 2.0 mg/g, 1.5 mg/g, 1.0 mg/g, 750 µg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable.

In some aspects, cured tobacco material or tobacco products provided herein comprise an average nicotine level selected from the group consisting of about 0.01%, 0.02%, 0.05%, 0.75%, 0.1%, 0.15%, 0.2%, 0.3%, 0.35%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, and 9% on a dry weight basis. In other aspects, cured tobacco material or tobacco products provided herein comprise an average nicotine level selected from the group consisting of about between 0.01% and 0.02%, between 0.02% and 0.05%, between 0.05% and 0.75%, between 0.75% and 0.1%, between 0.1% and 0.15%, between 0.15% and 0.2%, between 0.2% and 0.3%, between 0.3% and 0.35%, between 0.35% and 0.4%, between 0.4% and 0.5%, between 0.5% and 0.6%, between 0.6% and 0.7%, between 0.7% and 0.8%, between 0.8% and 0.9%, between 0.9% and 1%, between 1% and 1.1%, between 1.1% and 1.2%, between 1.2% and 1.3%, between 1.3% and 1.4%, between 1.4% and 1.5%, between 1.5% and 1.6%, between 1.6% and 1.7%, between 1.7% and 1.8%, between 1.8% and 1.9%, between 1.9% and 2%, between 2% and 2.1%, between 2.1% and 2.2%, between 2.2% and 2.3%, between 2.3% and 2.4%, between 2.4% and 2.5%, between 2.5% and 2.6%, between 2.6% and 2.7%, between 2.7% and 2.8%, between 2.8% and 2.9%, between 2.9% and 3%, between 3% and 3.1%, between 3.1% and 3.2%, between 3.2% and 3.3%, between 3.3% and 3.4%, between 3.4% and 3.5%, and between 3.5% and 3.6% on a dry weight basis. In further aspects, cured tobacco material or tobacco products provided herein comprise an average nicotine level selected from the group consisting of about between 0.01% and 0.1%, between 0.02% and 0.2%, between 0.03% and 0.3%, between 0.04% and 0.4%, between 0.05% and 0.5%, between 0.75% and 1%, between 0.1% and 1.5%, between 0.15% and 2%, between 0.2% and 3%, and between 0.3% and 3.5% on a dry weight basis.

The present disclosure also provides methods for breeding tobacco lines, cultivars, or varieties comprising a desirable level of total alkaloid or nicotine, e.g., low nicotine or nicotine free. Breeding can be carried out via any known procedures. DNA fingerprinting, SNP mapping, haplotype mapping or similar technologies may be used in a marker-assisted selection (MAS) breeding program to transfer or breed a desirable trait or allele into a tobacco plant. For example, a breeder can create segregating populations in a $F_2$ or backcross generation using F1 hybrid plants disclosed herein or further crossing the F1 hybrid plants with other donor plants with an agronomically desirable genotype. Plants in the $F_2$ or backcross generations can be screened for a desired agronomic trait or a desirable chemical profile using one of the techniques known in the art or listed herein. Depending on the expected inheritance pattern or the MAS technology used, self-pollination of selected plants before each cycle of backcrossing to aid identification of the desired individual plants can be performed. Backcrossing or other breeding procedure can be repeated until the desired phenotype of the recurrent parent is recovered. A recurrent parent in the present disclosure can be a flue-cured variety, a Burley variety, a dark air-cured variety, a dark fire-cured variety, or an Oriental variety. Other breeding techniques can be found, for example, in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y., incorporated herein by reference in their entirety.

Results of a plant breeding program using the tobacco plants described herein includes useful lines, cultivars, varieties, progeny, inbreds, and hybrids of the present disclosure. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972; on Oct. 23, 1978; and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A first tobacco variety and a second tobacco variety from which the first variety is essentially derived, are considered as having essentially identical genetic background. A "line" as distinguished from a variety most often denotes a group of plants used non-commercially, for example in plant research. A line typically displays little overall variation between individuals for one or more traits of interest, although there may be some variation between individuals for other traits.

In some aspects, the present disclosure provides a method of introgressing a low nicotine trait into a tobacco variety, the method comprising: (a) crossing a first tobacco variety comprising a low nicotine trait with a second tobacco variety without the low nicotine trait to produce one or more progeny tobacco plants; (b) genotyping the one or more progeny tobacco plants for a polymorphic marker linked to the low nicotine trait, wherein the polymorphic marker is in a chromosomal interval flanked by any two of polymorphic loci listed in Table 3 or flanked by any two of polymorphic loci listed in Table 4; and (c) selecting a progeny tobacco plant comprising the low nicotine trait. In other aspects, these methods further comprise backcrossing the selected progeny tobacco plant with the second tobacco variety. In further aspects, these methods further comprise: (d) crossing the selected progeny plant with itself or with the second tobacco variety to produce one or more further progeny tobacco plants; and (e) selecting a further progeny tobacco plant comprising the low nicotine trait. In some aspects, the step (e) of selecting comprises marker-assisted selection. In some aspects, these methods produce a single gene conversion comprising a low nicotine trait. In some aspects, these methods produce a single gene conversion comprising a Nic1 introgression. In some aspects, the second second tobacco variety is an elite variety. In other aspects, the genotyping step of these methods involve one or more molecular marker assays. In other aspects, the polymorphic marker used this method comprises a polymorphism selected from the group consisting of single nucleotide polymorphisms (SNPs), insertions or deletions in DNA sequence (Indels), simple sequence repeats of DNA sequence (SSRs), a restriction fragment length polymorphism (RFLP), and a tag SNP. In other aspects, the selected progeny tobacco plant comprises a shorter chromosome deletion at Nic1 locus compared to LA Burley 21.

In other aspects, the present disclosure provides a method of introgressing a low nicotine trait into a tobacco variety, the method comprising: (a) crossing a first tobacco variety comprising a low nicotine trait with a second tobacco variety without the low nicotine trait to produce one or more progeny tobacco plants; (b) genotyping the one or more progeny tobacco plants for a polymorphic marker linked to the low nicotine trait, wherein the polymorphic marker is within 20 cM of any one of polymorphic loci listed in Table 3 and Table 4; and (c) selecting a progeny tobacco plant comprising the low nicotine trait. In some aspects, this method comprises selecting simultaneously or concurrently for one or more molecular markers associated with or closely linked to Nic1 locus as well as one or more molecular markers associated with or closely linked to Nic2 locus.

In some aspects, the present disclosure provides a method of selecting a tobacco plant having a low nicotine trait, the method comprising: (a) isolating nucleic acids from a collection of tobacco germplasm; (b) assaying the nucleic acids for one or more markers closely linked to Nic1 locus; and (c) selecting a tobacco plant having a low nicotine trait based on the marker assay. In some aspects, the assayed one or more markers closely linked to Nic1 locus are within about 20 cM, 10 cM, 5 cM, 4 cM, 3 cM, 2 cM, 1 cM, 0.5 cM, or less than 0.5 cM of any one of polymorphic loci listed in Table 3. In other aspects, this method further comprising assaying for one or more markers closely linked to Nic2 locus. In some aspects, the assayed one or more markers closely linked to Nic2 locus are within about 20 cM, 10 cM, 5 cM, 4 cM, 3 cM, 2 cM, 1 cM, 0.5 cM, or less than 0.5 cM of any one of polymorphic loci listed in Table 4. In some aspects, this method further comprises determining the nicotine level of the selected plant to confirm the low nicotine trait.

Also disclosed herein is a method of introgressing a low nicotine trait into a tobacco variety, the method comprising: (a) crossing a first tobacco variety comprising a low nicotine trait with a second tobacco variety without the low nicotine trait to produce one or more progeny tobacco plants; (b) genotyping the one or more progeny tobacco plants for a polymorphic marker linked to the low nicotine trait, wherein the polymorphic marker is in a chromosomal interval flanked by any two of polymorphic loci listed in Table 4; and (c) selecting a progeny tobacco plant comprising the low nicotine trait. In some aspects, these methods produce a single gene conversion comprising a low nicotine trait. In some aspects, these methods produce a single gene conversion comprising a Nic2 introgression. In some aspects, the second tobacco variety is an elite variety. In other aspects, the genotyping step of these methods involve one or more molecular marker assays. In other aspects, the polymorphic marker used this method comprises a polymorphism selected from the group consisting of single nucleotide polymorphisms (SNPs), insertions or deletions in DNA sequence (Indels), simple sequence repeats of DNA sequence (SSRs), a restriction fragment length polymorphism (RFLP), and a tag SNP. In other aspects, the selected progeny tobacco plant comprises a shorter chromosome deletion at Nic2 locus compared to LA Burley 21.

As used herein, "locus" is a chromosome region where a polymorphic nucleic acid, trait determinant, gene, or marker is located. The loci of this disclosure comprise one or more polymorphisms in a population; e.g., alternative alleles are present in some individuals. As used herein, "allele" refers to an alternative nucleic acid sequence at a particular locus. The length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. As used herein, the term "chromosome interval" designates a contiguous linear span of genomic DNA that resides on a single chromosome.

As used herein, a centimorgan ("cM") is a unit of measure of recombination frequency. One cM is equal to a 1% chance that a marker at one genetic locus will be separated from a marker at, a second locus due to crossing over in a single generation. Genetic distances referred herein can be calculated from recombination values using the Kosambi function (Kosambi, The estimation of map distances from recombination values. Annals of Eugenics, 12:172-75 (1944)).

As used herein, "closely linked to" or "associated with" means that the marker or locus is within about 20 cM, 10 cM, 5 cM, 1 cM, 0.5 cM, or less than 0.5 cM of another marker or locus. For example, 20 cM means that recombination between the marker and the locus with a frequency of equal to or less than about 20%.

As used herein, "introgression" or "introgress" refers to the transmission of a desired allele of a genetic locus from one genetic background to another.

As used herein, "crossed" or "cross" means to produce progeny via fertilization (e.g. cells, seeds or plants) and includes crosses between plants (sexual) and self fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the F1 generation. The term "BC1" refers to the second use of the recurrent parent, "BC2" refers to the third use of the recurrent parent, and so on. In some aspects, a backcross is performed repeatedly, with a progeny individual of each successive backcross generation being itself backcrossed to the same parental genotype.

As used herein, "single gene converted" or "single gene conversion" refers to plants that are developed using a plant breeding technique known as backcrossing, or via genetic engineering, wherein essentially all of the desired morphological and physiological characteristics of a variety are recovered in addition to the single gene transferred into the variety via the backcrossing technique or via genetic engineering.

As used herein, "elite variety" means any variety that has resulted from breeding and selection for superior agronomic performance.

As used herein, "selecting" or "selection" in the context of marker-assisted selection or breeding refer to the act of picking or choosing desired individuals, normally from a population, based on certain pre-determined criteria.

As used herein, the term "trait" refers to one or more detectable characteristics of a cell or organism which can be influenced by genotype. The phenotype can be observable to the naked eye, or by any other means of evaluation known in the art, e.g., microscopy, biochemical analysis, genomic analysis, an assay for a particular disease tolerance, etc. In some cases, a phenotype is directly controlled by a single gene or genetic locus, e.g., a "single gene trait." In other cases, a phenotype is the result of several genes.

As used herein, "marker assay" means a method for detecting a polymorphism at a particular locus using a particular method, e.g., measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "marker assisted selection" (MAS) is a process by which phenotypes are selected based on marker genotypes. "Marker assisted selection breeding" refers to the process of selecting a desired trait or traits in a plant or plants by detecting one or more nucleic acids from the plant, where the nucleic acid is linked to the desired trait, and then selecting the plant or germplasm possessing those one or more nucleic acids.

As used herein, "polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism (RFLP), and a tag SNP. A genetic marker, a gene, a DNA-derived sequence, a RNA-derived sequence, a promoter, a 5' untranslated region of a gene, a 3' untranslated region of a gene, microRNA, siRNA, a tolerance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

As used herein, "SNP" or "single nucleotide polymorphism" means a sequence variation that occurs when a single nucleotide (A, T, C, or G) in the genome sequence is altered or variable. "SNP markers" exist when SNPs are mapped to sites on the genome.

As used herein, "marker" or "molecular marker" or "marker locus" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. In some aspects, markers used herein exhibit LOD scores of 2 or greater, 3 or greater, 4 or greater, 5 or greater, 6 or greater, 7 or greater, 8 or greater, or 9 or greater with Nic1 or Nic2 loci disclosed herein, measuring using a method known in the art such as Qgene Version 2.23 (1996) and default parameters.

In one aspect, the present disclosure provides a tobacco plant, or part thereof, comprising a first chromosomal deletion flanked by and not comprising any two of Nic1 Marker Nos. 1 to 207, a second chromosomal deletion flanked by and not comprising any two of Nic2 Marker Nos. 1 to 340, or both said first and said second chromosomal deletions, wherein said tobacco plant is capable of producing leaves having a USDA grade index value of 50 or more, 55 or more, 60 or more, 65 or more, 70 or more, 75 or more, 80 or more, 85 or more, 90 or more, or 95 or more. In another aspect, a tobacco plant comprises a nicotine level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, and less than 0.05%. In one aspect, further provided are a population of the tobacco plants in this paragraph, cured tobacco material made therefrom, a tobacco blend comprising said cured tobacco material, and a tobacco product comprising the cured tobacco material.

In another aspect, the present disclosure provides a tobacco plant, or part thereof, comprising a mutation selected from the group consisting of a first chromosomal deletion flanked by and not comprising any two of Nic1 Marker Nos. 1 to 207, a second chromosomal deletion flanked by and not comprising any two of Nic2 Marker Nos. 1 to 340, and both said first and said second chromosomal deletions, wherein said tobacco plant is capable of producing leaves having a USDA grade index value comparable to that of a control plant when grown in similar growth conditions, wherein said control plant shares an essentially identical genetic background with said tobacco plant except said mutation. In one aspect, a tobacco plant comprises nicotine at a level below 1%, below 2%, below 5%, below 8%, below 10%, below 12%, below 15%, below 20%, below 25%, below 30%, below 40%, below 50%, below 60%, below 70%, or below 80% of the nicotine level of said control plant when grown in similar growth conditions. In one aspect, further provided are a population of the tobacco plants in this paragraph, cured tobacco material made therefrom, a tobacco blend comprising said cured tobacco material, and a tobacco product comprising the cured tobacco material.

In one aspect, a first chromosomal deletion is flanked by and not comprising any two of Nic1 Marker Nos. 1 to 20, 21 to 40, 41 to 60, 61 to 80, 81 to 100, 101 to 120, 121 to 140, 141 to 160, 161 to 180, 181 to 200, or 201 to 207. In another aspect, a first chromosomal deletion is flanked by and not comprising any two of Nic1 Marker Nos. 1 to 10, 11 to 20, 21 to 30, 31 to 40, 41 to 50, 51 to 60, 61 to 70, 71 to 80, 81 to 90, 91 to 100, 101 to 110, 111 to 120, 121 to 130, 131 to 140, 141 to 150, 151 to 160, 161 to 170, 171 to 180, 181 to 190, 191 to 200, or 201 to 207.

In one aspect, a second chromosomal deletion is flanked by and not comprising any two of Nic2 Marker Nos. 1 to 20, 21 to 40, 41 to 60, 61 to 80, 81 to 100, 101 to 120, 121 to 140, 141 to 160, 161 to 180, 181 to 200, 201 to 220, 221 to 240, 241 to 260, 261 to 280, 281 to 300, 301 to 320, or 321 to 340. In another aspect, a second chromosomal deletion is flanked by and not comprising any two of Nic2 Marker Nos. 1 to 10, 11 to 20, 21 to 30, 31 to 40, 41 to 50, 51 to 60, 61 to 70, 71 to 80, 81 to 90, 91 to 100, 101 to 110, 111 to 120, 121 to 130, 131 to 140, 141 to 150, 151 to 160, 161 to 170, 171 to 180, 181 to 190, 191 to 200, 201 to 210, 211 to 220, 221 to 230, 231 to 240, 241 to 250, 251 to 260, 261 to 270, 271 to 280, 281 to 290, 291 to 300, 301 to 310, 311 to 320, 321 to 330, or 331 to 340.

It is understood that any tobacco plant of the present disclosure can further comprise additional agronomically desirable traits, for example, by transformation with a genetic construct or transgene using a technique known in the art. Without limitation, an example of a desired trait is herbicide resistance, pest resistance, disease resistance; high yield; high grade index value; curability; curing quality; mechanical harvestability; holding ability; leaf quality; height, plant maturation (e.g., early maturing, early to medium maturing, medium maturing, medium to late maturing, or late maturing); stalk size (e.g., a small, medium, or a large stalk); or leaf number per plant (e.g., a small (e.g., 5-10 leaves), medium (e.g., 11-15 leaves), or large (e.g., 16-21) number of leaves), or any combination. In some aspects, low-nicotine or nicotine-free tobacco plants or seeds disclosed herein comprise one or more transgenes expressing one or more insecticidal proteins, such as, for example, a crystal protein of *Bacillus thuringiensis* or a vegetative insecticidal protein from *Bacillus cereus*, such as VIP3 (see, for example, Estruch et al. (1997) *Nat. Biotechnol.* 15:137). In other aspects, tobacco plants disclosed herein further comprise an introgressed trait conferring resistance to brown stem rot (U.S. Pat. No. 5,689,035) or resistance to cyst nematodes (U.S. Pat. No. 5,491,081).

The present disclosure also provides tobacco plants comprising an altered nicotine level but having a yield comparable to the yield of corresponding initial tobacco plants without such a nicotine level alternation. In one aspect, a low-nicotine or nicotine-free tobacco variety disclosed herein provides a yield selected from the group consisting of about between 1200 and 3500, between 1300 and 3400, between 1400 and 3300, between 1500 and 3200, between 1600 and 3100, between 1700 and 3000, between 1800 and 2900, between 1900 and 2800, between 2000 and 2700, between 2100 and 2600, between 2200 and 2500, and between 2300 and 2400 lbs/acre. In another aspect, a low-nicotine or nicotine-free tobacco variety disclosed herein provides a yield selected from the group consisting of about between 1200 and 3500, between 1300 and 3500, between 1400 and 3500, between 1500 and 3500, between 1600 and 3500, between 1700 and 3500, between 1800 and 3500, between 1900 and 3500, between 2000 and 3500, between 2100 and 3500, between 2200 and 3500, between 2300 and 3500, between 2400 and 3500, between 2500 and 3500, between 2600 and 3500, between 2700 and 3500, between 2800 and 3500, between 2900 and 3500, between 3000 and 3500, and between 3100 and 3500 lbs/acre. In further aspects, low-nicotine or nicotine-free tobacco plants disclosed herein provide a yield between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the yield of a control plant having essentially identical genetic background except a Nic1 mutation, a Nic2 mutation, a Nic1 transgene, a Nic2 transgene, or combinations thereof. In further aspects, low-nicotine or nicotine-free tobacco plants disclosed herein provide a yield between 70% and 125%, between 75% and 120%, between 80% and 115%, between 85% and 110%, or between 90% and 100% of the yield of a control plant having essentially identical genetic background except a Nic1 mutation, a Nic2 mutation, a Nic1 transgene, a Nic2 transgene, or combinations thereof In one aspect, a low-nicotine or nicotine-free tobacco variety disclosed herein is adapted for machine harvesting. In another aspect, a low-nicotine or nicotine-free tobacco variety disclosed herein is harvested mechanically.

In some aspects, tobacco plants provided herein are hybrid plants. Hybrids can be produced by preventing self-pollination of female parent plants (e.g., seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility wherein a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting F1 seed is harvested.

Plants can be used to form single-cross tobacco F1 hybrids. Pollen from a male parent plant is manually transferred to an emasculated female parent plant or a female parent plant that is male sterile to form F1 seed. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed. Self-incompatibility can be used to particular advantage to prevent self-pollination of female parents when forming a double-cross hybrid.

In one aspect, a low-nicotine or nicotine-free tobacco variety disclosed herein is male sterile. In another aspect, a low-nicotine or nicotine-free tobacco variety disclosed herein is cytoplasmic male sterile. Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp.

In further aspects, tobacco parts provided herein include, but are not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In one aspect, tobacco part provided herein does not include seed. In one aspect, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

The provided cells, tissues and organs may be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, vascular tissue. In another aspect, this disclosure provides a tobacco plant chloroplast. In a further aspect, this disclosure provides epidermal cells, stomata cell, leaf or root hairs, a storage root, or a tuber. In another aspect, this disclosure provides a tobacco protoplast.

Skilled artisans understand that tobacco plants naturally reproduce via seeds, not via asexual reproduction or vegetative propagation. In one aspect, this disclosure provides tobacco endosperm. In another aspect, this disclosure provides tobacco endosperm cells. In a further aspect, this disclosure provides a male or female sterile tobacco plant, which cannot reproduce without human intervention.

In some aspects, the present disclosure provides a nucleic acid molecule comprising at least about 40%, 45%, 50%, 55%, 60%, 65%, 70%, 75%, 80%, 85%, 90%, 91%, 92%, 93%, 94%, 95%, 96%, 97%, 98%, 99%, or 100% identity to a sequence selected from the group consisting of SEQ ID NOs: 9 to 48, 75 to 82, 86 to 115, and 131 to 146, and fragments thereof. In other aspects, the present disclosure provides a nucleic acid molecule comprising at least about 40%, 45%, 50%, 55%, 60%, 65%, 70%, 75%, 80%, 85%, 90%, 91%, 92%, 93%, 94%, 95%, 96%, 97%, 98%, 99%, or 100% identity to a sequence selected from the group consisting of SEQ ID NOs: 13, 28, 33, 48, 82, 86, 87, 101, 102, 145, 146, and fragments thereof. In some aspects, the present disclosure provides a polypeptide or protein comprising at least about 40%, 45%, 50%, 55%, 60%, 65%, 70%, 75%, 80%, 85%, 90%, 91%, 92%, 93%, 94%, 95%, 96%, 97%, 98%, 99%, or 100% identity to an amino acid sequence selected from the group consisting of SEQ ID NOs: 49 to 68, 116 to 130, and 147. In other aspects, the present disclosure provides a polypeptide or protein comprising at least about 40%, 45%, 50%, 55%, 60%, 65%, 70%, 75%, 80%, 85%, 90%, 91%, 92%, 93%, 94%, 95%, 96%, 97%, 98%, 99%, or 100% sequence similarity to an amino acid sequence selected from the group consisting of SEQ ID NOs: 49 to 68, 116 to 130, and 147. In other aspects, the present disclosure provides a biologically active variant of a protein having an amino acid sequence selected from the group consisting of SEQ ID NOs: 49 to 68, 116 to 130, and 147. A biologically active variant of a protein of the present disclosure may differ from that protein by as few as 1-15 amino acid residues, as few as 10, as few as 9, as few as 8, as few as 7, as few as 6, as few as 5, as few as 4, as few as 3, as few as 2, or as few as 1 amino acid residue. Also provided herein are orthologous genes or proteins of genes or proteins from Nic1 locus. "Orthologs" are genes derived from a common ancestral gene and which are found in different species as a result of speciation. Orthologs may share at least 60%, 70%, 75%, 80%, 85%, 90%, 91%, 92%, 93%, 94%, 95%, 96%, 97%, 98%, 99%, or greater sequence identity or similarity at the nucleotide sequence and/or the protein sequence level. Functions of orthologs are often highly conserved among species.

As used herein, the term "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity."

Nucleic acid molecules, polypeptides, or proteins provided herein can be isolated or substantially purified. An "isolated" or "purified" nucleic acid molecule, polypeptide, protein, or biologically active portion thereof, is substantially or essentially free from components that normally accompany or interact with the polynucleotide or protein as found in its naturally occurring environment. For example, an isolated or purified polynucleotide or protein is substantially free of other cellular material, or culture medium when produced by recombinant techniques, or substantially free of chemical precursors or other chemicals when chemically synthesized.

The present disclosure further provides a method manufacturing a tobacco product comprising tobacco material from tobacco plants disclosed herein. In some aspects, methods disclosed herein comprise conditioning aged tobacco material made from tobacco plants disclosed herein to increase its moisture content from between about 12.5% and about 13.5% to about 21%, blending the conditioned tobacco material to produce a desirable blend. In one aspect, the method of manufacturing a tobacco product disclosed herein further comprises casing or flavoring the blend. Generally, during the casing process, casing or sauce materials are added to blends to enhance their quality by balancing the chemical composition and to develop certain desired flavor characteristics. Further details for the casing process can be found in *Tobacco Production, Chemistry and Technology*, Edited by L. Davis and M. Nielsen, Blackwell Science, 1999.

Tobacco material provided herein can be also processed using methods including, but not limited to, heat treatment (e.g., cooking, toasting), flavoring, enzyme treatment, expansion and/or curing. Both fermented and non-fermented tobaccos can be processed using these techniques. Examples of suitable processed tobaccos include dark air-cured, dark fire cured, burley, flue cured, and cigar filler or wrapper, as well as the products from the whole leaf stemming operation. In some aspects, tobacco fibers include up to 70% dark tobacco on a fresh weight basis. For example, tobacco can be conditioned by heating, sweating and/or pasteurizing steps as described in U.S. Publication Nos. 2004/0118422 or 2005/0178398.

Tobacco material provided herein can be subject to fermentation. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. In addition to modifying the aroma of the leaf, fermentation can change either or both the color and texture of a leaf. Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco, Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into the oral product. The tobacco, in some cases, is long cut fermented cured moist tobacco having an oven volatiles content of between 48 and 50 weight percent prior to mixing with the copolymer and optionally flavorants and other additives.

In some aspects, tobacco material provided herein can be processed to a desired size. In certain aspects, tobacco fibers can be processed to have an average fiber size of less than 200 micrometers. In some aspects, tobacco fibers are between 75 and 125 micrometers. In other aspects, tobacco fibers are processed to have a size of 75 micrometers or less. In some aspects, tobacco fibers include long cut tobacco, which can be cut or shredded into widths of about 10 cuts/inch up to about 110 cuts/inch and lengths of about 0.1 inches up to about 1 inch. Double cut tobacco fibers can have a range of particle sizes such that about 70% of the double cut tobacco fibers falls between the mesh sizes of −20 mesh and 80 mesh.

Tobacco material provided herein can be processed to have a total oven volatiles content of about 10% by weight or greater; about 20% by weight or greater; about 40% by weight or greater; about 15% by weight to about 25% by weight; about 20% by weight to about 30% by weight; about 30% by weight to about 50% by weight; about 45% by weight to about 65% by weight; or about 50% by weight to about 60% by weight. Those of skill in the art will appreciate that "moist" tobacco typically refers to tobacco that has an oven volatiles content of between about 40% by weight and about 60% by weight (e.g., about 45% by weight to about 55% by weight, or about 50% by weight). As used herein, "oven volatiles" are determined by calculating the percentage of weight loss for a sample after drying the sample in a pre-warmed forced draft oven at 110° C. for 3.25 hours. The oral product can have a different overall oven volatiles content than the oven volatiles content of the tobacco fibers used to make the oral product. The processing steps described herein can reduce or increase the oven volatiles content.

The following paragraphs provide a list of exemplary embodiments.

Embodiment 1

A tobacco plant, or part thereof, comprising a mutation in Nic1 locus, a mutation in Nic2 locus, or both, wherein said tobacco plant is capable of producing leaves having a USDA grade index value of 50 or more.

Embodiment 2

The tobacco plant, or part thereof, of Embodiment 1, wherein said tobacco plant is capable of producing leaves having a USDA grade index value selected from the group consisting of 55 or more, 60 or more, 65 or more, 70 or more, 75 or more, 80 or more, 85 or more, 90 or more, and 95 or more.

Embodiment 3

The tobacco plant, or part thereof, of Embodiment 1, wherein said tobacco plant is capable of producing leaves having a USDA grade index value comparable to that of a control plant when grown in similar growth conditions, wherein said control plant shares an essentially identical genetic background with said tobacco plant except said mutation.

Embodiment 4

The tobacco plant, or part thereof, of Embodiment 1, wherein said tobacco plant is capable of producing leaves having a USDA grade index value of at least about 65%, at least about 70%, at least about 75%, at least about 80%, at least about 85%, at least about 90%, at least about 95%, or at least about 98% of the USDA grade index value of a control plant when grown in similar growth conditions, wherein said control plant shares an essentially identical genetic background with said tobacco plant except said mutation.

Embodiment 6

The tobacco plant, or part thereof, of Embodiment 1, wherein said tobacco plant comprises a nicotine level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, and less than 0.05%.

Embodiment 7

The tobacco plant, or part thereof, of Embodiment 1, wherein said tobacco plant further comprises a transgene or mutation directly suppressing the expression or activity of one or more genes encoding a product selected from the group consisting of PMT, MPO, QPT, BBL, A622, and MATE transporter.

Embodiment 8

A tobacco plant, or part thereof, comprising a mutation in Nic1 locus, a mutation in Nic2 locus, or both, wherein said tobacco plant is capable of producing leaves having a USDA grade index value comparable to that of a control plant when grown in similar growth conditions, wherein said control plant shares an essentially identical genetic background with said tobacco plant except said mutation.

Embodiment 9

The tobacco plant, or part thereof, of Embodiment 8, wherein said tobacco plant is capable of producing leaves having a USDA grade index value selected from the group consisting of 55 or more, 60 or more, 65 or more, 70 or more, 75 or more, 80 or more, 85 or more, 90 or more, and 95 or more.

Embodiment 10

The tobacco plant, or part thereof, of Embodiment 8, wherein said tobacco plant is capable of producing leaves having a USDA grade index value of at least about 65%, at least about 70%, at least about 75%, at least about 80%, at least about 85%, at least about 90%, at least about 95%, or at least about 98% of the grading index of said control plant.

Embodiment 11

The tobacco plant, or part thereof, of Embodiment 8, wherein said tobacco plant comprises nicotine at a level below 1%, below 2%, below 5%, below 8%, below 10%, below 12%, below 15%, below 20%, below 25%, below 30%, below 40%, below 50%, below 60%, below 70%, or below 80% of the nicotine level of said control plant when grown in similar growth conditions.

Embodiment 12

The tobacco plant, or part thereof, of Embodiment 8, wherein said tobacco plant further comprises a transgene or mutation directly suppressing the expression or activity of one or more genes encoding a product selected from the group consisting of PMT, MPO, QPT, BBL, A622, and MATE transporter.

Embodiment 13

A plant of a tobacco variety comprising a mutation selected from the group consisting of a nic1 mutation, a nic2 mutation, and a combination thereof, wherein said tobacco variety has a leaf grading index comparable to the leaf grading index of a control tobacco variety when grown in similar growth conditions, wherein said control tobacco variety shares an essentially identical genetic background with said tobacco variety except said mutation.

Embodiment 14

A non-transgenic tobacco plant, or part thereof, comprising a nicotine level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, and less than 0.05%, wherein said tobacco plant is capable of producing leaves having a USDA grade index value of 50 or more 55 or more, 60 or more, 65 or more, 70 or more, 75 or more, 80 or more, 85 or more, 90 or more, and 95 or more.

Embodiment 15

The non-transgenic tobacco plant, or part thereof, of claim 14, wherein said non-transgenic tobacco plant comprises a nicotine level of less than 2.0% and is capable of producing leaves having a USDA grade index value of 70 or more.

Embodiment 16

The non-transgenic tobacco plant, or part thereof, of claim 14, wherein said non-transgenic tobacco plant comprises a nicotine level of less than 1.0% and is capable of producing leaves having a USDA grade index value of 70 or more.

Embodiment 17

A tobacco plant, or part thereof, comprising a non-transgenic mutation, wherein said non-transgenic mutation reduces the nicotine level of said tobacco plant to below 1%, below 2%, below 5%, below 8%, below 10%, below 12%, below 15%, below 20%, below 25%, below 30%, below 40%, below 50%, below 60%, below 70%, or below 80% of the nicotine level of a control plant when grown in similar growth conditions, wherein said tobacco plant is capable of producing leaves having a USDA grade index value comparable to the USDA grade index value of said control plant, and wherein said control plant shares an essentially identical genetic background with said tobacco plant except said non-transgenic mutation.

Embodiment 18

A population of the tobacco plants of any one of Embodiments 1 to 17.

Embodiment 19

Cured tobacco material from the tobacco plant of any one of claims 1 to 17.

Embodiment 20

The cured tobacco material of Embodiment 19, wherein said cured tobacco material is made by a curing process selected from the group consisting of flue curing, air curing, fire curing, and sun curing.

Embodiment 21

A tobacco blend comprising the cured tobacco material of claim 19.

Embodiment 22

The tobacco blend of Embodiment 21, wherein the cured tobacco material constitutes about at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of cured tobacco in said tobacco blend by weight.

Embodiment 23

The tobacco blend of Embodiment 21, wherein the cured tobacco material constitutes about at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of cured tobacco in said tobacco blend by volume.

Embodiment 24

A tobacco product comprising the cured tobacco material of claim 19.

Embodiment 25

The tobacco product of Embodiment 24, wherein the tobacco product is selected from the group consisting of a cigarette, a cigarillo, a non-ventilated recess filter cigarette, a vented recess filter cigarette, a cigar, snuff, pipe tobacco, cigar tobacco, cigarette tobacco, chewing tobacco, leaf tobacco, shredded tobacco, and cut tobacco.

Embodiment 26

The tobacco product of Embodiment 24, wherein the tobacco product is a smokeless tobacco product.

Embodiment 27

The tobacco product of Embodiment 26, wherein the smokeless tobacco product is selected from the group consisting of loose leaf chewing tobacco, plug chewing tobacco, moist snuff, and nasal snuff.

Embodiment 28

A reconstituted tobacco comprising the cured tobacco material of claim 19.

Embodiment 29

A tobacco plant, or part thereof, comprising a mutation in Nic1 locus, wherein said mutation is absent from a LA Burley 21 variety.

Embodiment 30

The tobacco plant, or part thereof, of Embodiment 29, wherein said tobacco plant comprises a shorter chromosome deletion at Nic1 locus compared to said LA Burley 21 variety.

Embodiment 31

The tobacco plant, or part thereof, of Embodiment 29, wherein said tobacco plant comprises a lower level of nicotine compared to a control tobacco plant without said mutation when grown in similar growth conditions.

Embodiment 32

The tobacco plant, or part thereof, of Embodiment 29, wherein said tobacco plant comprises nicotine at a level below 1%, below 2%, below 5%, below 8%, below 10%, below 12%, below 15%, below 20%, below 25%, below 30%, below 40%, below 50%, below 60%, below 70%, or below 80% of the nicotine level in a control tobacco plant without said mutation when grown in similar growth conditions.

Embodiment 33

The tobacco plant, or part thereof, of Embodiment 29, wherein said tobacco plant comprises a lower level of total alkaloid compared to a control tobacco plant without said mutation when grown in similar growth conditions.

Embodiment 34

The tobacco plant, or part thereof, of Embodiment 29, wherein said tobacco plant comprises a lower level of one or more alkaloid selected from the group consisting of nicotine, nornicotine, anabasine, and anatabine, compared to a control tobacco plant without said mutation when grown in similar growth conditions.

Embodiment 35

The tobacco plant, or part thereof, of Embodiment 29, wherein said tobacco plant comprises a similar level of one or more compounds selected from the group consisting of 3-methylvaleric acid, valeric acid, isovaleric acid, a labdenoid, a cembrenoid, a sugar ester, and a reducing sugar, compared to a control tobacco plant without said mutation when grown in similar growth conditions.

Embodiment 36

The tobacco plant, or part thereof, of Embodiment 29, wherein said mutation is homozygous.

Embodiment 37

The tobacco plant, or part thereof, of Embodiment 29, wherein said mutation is heterozygous.

Embodiment 38

The tobacco plant, or part thereof, of Embodiment 29, wherein said mutation is selected from the group consisting of a point mutation, a deletion, an insertion, a duplication, and an inversion.

Embodiment 39

The tobacco plant, or part thereof, of Embodiment 29, wherein said mutation is introduced by an approach selected from the group consisting of random mutagenesis and targeted mutagenesis.

Embodiment 40

The tobacco plant, or part thereof, of Embodiment 39, wherein said targeted mutagenesis is mediated by meganuclease, zinc finger nuclease, TALEN, or CRISPR.

Embodiment 41

The tobacco plant, or part thereof, of Embodiment 29, wherein said tobacco plant further comprises a mutation in Nic2 locus.

Embodiment 42

The tobacco plant, or part thereof, of Embodiment 29, wherein said mutation is located within a gene comprising a sequence having at least 80%, at least 85%, at least 90%, at least 95%, at least 97%, at least 98%, at least 99% identity to a sequence selected from the group consisting of SEQ ID NOs: 9 to 28, 75 to 82, 86 to 100, 145, and fragments thereof.

Embodiment 43

The tobacco plant, or part thereof, of Embodiment 29, wherein said mutation reduces the expression or activity of said gene.

Embodiment 44

The tobacco plant, or part thereof, of Embodiment 29, wherein said mutation is located within a gene comprising a sequence having at least 80%, at least 85%, at least 90%, at least 95%, at least 97%, at least 98%, at least 99% identity to a sequence selected from the group consisting of SEQ ID NOs: 13, 28, 33, 48, 82, 86, 87, 101, 102, 145, and 146, and fragments thereof.

Embodiment 45

The tobacco plant, or part thereof, of Embodiment 29, wherein said mutation is located within a sequence having at least 80%, at least 85%, at least 90%, at least 95%, at least 97%, at least 98%, at least 99% identity to a sequence selected from the group consisting of SEQ ID NOs: 13, 28, 33, 48, 82, 86, 87, 101, 102, 145, and 146, and fragments thereof.

Embodiment 46

The tobacco plant, or part thereof, of Embodiment 29, wherein said mutation is located within a gene comprising a coding sequence having at least 80%, at least 85%, at least 90%, at least 95%, at least 97%, at least 98%, at least 99% identity to a sequence selected from the group consisting of SEQ ID NOs: 33, 48, 101, 102, and 146, and fragments thereof.

Embodiment 47

The tobacco plant, or part thereof, of Embodiment 29, wherein said mutation is located within a sequence having at least 80%, at least 85%, at least 90%, at least 95%, at least 97%, at least 98%, at least 99% identity to a sequence selected from the group consisting of SEQ ID NOs: 33, 48, 101, 102, and 146, and fragments thereof.

Embodiment 48

The tobacco plant, or part thereof, of Embodiment 29, wherein said mutation is located within a gene encoding a polypeptide having at least 80%, at least 85%, at least 90%, at least 95%, at least 97%, at least 98%, at least 99% identity to a sequence selected from the group consisting of SEQ ID NOs: 53, 68, 116, 117, 147, and fragments thereof.

Embodiment 49

The tobacco plant, or part thereof, of Embodiment 29, wherein said plant further comprises a reduced level of mRNA, protein, or both of one or more genes encoding a product selected from the group consisting of PMT, MPO, QPT, BBL, MATE, and A622, compared to a tobacco plant without said mutation when grown in similar growth conditions.

Embodiment 50

The tobacco plant, or part thereof, of Embodiment 29, wherein said plant further comprises a transgene or mutation suppressing the expression or activity of one or more genes encoding a product selected from the group consisting of PMT, MPO, QPT, BBL, A622, and MATE transporter.

Embodiment 51

The tobacco plant, or part thereof, of Embodiment 29, wherein said tobacco plant is a hybrid.

Embodiment 52

The tobacco plant, or part thereof, of Embodiment 29, wherein said part is selected from the group consisting of a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast.

Embodiment 53

The tobacco plant, or part thereof, of Embodiment 29, wherein said tobacco plant is from a variety selected from the group consisting of flue-cured tobacco, air-cured tobacco, dark fire-cured tobacco, and *Galpao* tobacco, and Oriental tobacco.

Embodiment 54

The tobacco plant, or part thereof, of Embodiment 29, wherein said tobacco plant is from a variety selected from the group consisting of Burley tobacco, Maryland tobacco, and dark air-cured tobacco.

Embodiment 55
A population of the tobacco plants of Embodiment 29.

Embodiment 56
Cured tobacco material from the tobacco plant of Embodiment 29.

Embodiment 57
The cured tobacco material of Embodiment 56, wherein said cured tobacco material comprises a lower level of nicotine compared to cured tobacco material from a control tobacco plant without said mutation.

Embodiment 58
The cured tobacco material of Embodiment 56, wherein said tobacco plant comprises nicotine at a level between 0.2% and 0.6%.

Embodiment 59
The cured tobacco material of Embodiment 56, wherein said tobacco plant comprises nicotine at a level between 1.0% and 3.0%.

Embodiment 60
The cured tobacco material of Embodiment 56, wherein said cured tobacco material is made by a curing process selected from the group consisting of flue curing, air curing, fire curing, and sun curing.

Embodiment 61
A tobacco blend comprising the cured tobacco material of claim 56.

Embodiment 62
A tobacco product comprising the cured tobacco material of claim 56.

Embodiment 63
The tobacco product of Embodiment 62, wherein the tobacco product is selected from the group consisting of a cigarette, a cigarillo, a non-ventilated recess filter cigarette, a vented recess filter cigarette, a cigar, snuff, pipe tobacco, cigar tobacco, cigarette tobacco, chewing tobacco, leaf tobacco, shredded tobacco, and cut tobacco.

Embodiment 64
The tobacco product of Embodiment 62, wherein the tobacco product is a smokeless tobacco product.

Embodiment 65
The tobacco product of Embodiment 64, wherein the smokeless tobacco product is selected from the group consisting of loose leaf chewing tobacco, plug chewing tobacco, moist snuff, and nasal snuff.

Embodiment 66
A reconstituted tobacco comprising the cured tobacco material of claim 56.

Embodiment 67
A recombinant DNA construct comprising a promoter that is functional in a tobacco cell and operably linked to a polynucleotide that encodes a polypeptide having an amino acid sequence at least 80%, at least 85%, at least 90%, at least 95%, at least 97%, at least 98%, at least 99% identical to an amino acid sequence selected from the group consisting of SEQ ID NOs: 49 to 68, 84, 116 to 130, 147, and fragments thereof.

Embodiment 68
A tobacco plant, or part thereof, comprising the recombinant DNA construct of claim 67.

Embodiment 69
A tobacco plant, or part thereof, of Embodiment 68, wherein said tobacco plant comprises a higher level of nicotine compared to a control tobacco plant without said recombinant DNA construct.

Embodiment 70
Cured tobacco material from the tobacco plant of Embodiment 68.

Embodiment 71
A tobacco product comprising the cured tobacco material of claim 70.

Embodiment 72
A method of increasing the nicotine level of a tobacco plant, said method comprising transforming a tobacco plant with the recombinant DNA construct of claim 67.

Embodiment 73
A recombinant DNA construct comprising a promoter that is functional in a tobacco cell and operably linked to a polynucleotide that encodes an RNA molecule capable of binding to an RNA encoding a polypeptide having an amino acid sequence at least 80%, at least 85%, at least 90%, at least 95%, at least 97%, at least 98%, at least 99% identical to an amino acid sequence selected from the group consisting of SEQ ID NO: 49 to 68, 84, 116 to 130, 147, and fragments thereof, and wherein said RNA molecule suppresses the expression of said polypeptide.

Embodiment 74
A tobacco plant, or part thereof, comprising the recombinant DNA construct of claim 73.

Embodiment 75
The tobacco plant, or part thereof, of Embodiment 74, wherein said RNA molecule is selected from the group consisting of a microRNA, an siRNA, and a trans-acting siRNA.

Embodiment 76
The tobacco plant, or part thereof, of Embodiment 74, wherein said polynucleotide encodes a double stranded RNA.

Embodiment 77
The tobacco plant, or part thereof, of Embodiment 74, wherein said tobacco plant comprises a lower level of nicotine compared to a control tobacco plant without said recombinant DNA construct.

Embodiment 78
Cured tobacco material from the tobacco plant of Embodiment 74.

Embodiment 79
A tobacco product comprising the cured tobacco material of claim 78.

Embodiment 80
A method of reducing the nicotine level of a tobacco plant, said method comprising transforming a tobacco plant with the recombinant DNA construct of claim 73.

Embodiment 81
A tobacco plant, or part thereof, comprising a heterologous expression cassette comprising a Nic1 inhibitory sequence of a gene comprising a sequence selected from the group consisting of SEQ ID NOs: 9 to 28, 75 to 82, 86 to 100, 145, and fragments thereof, wherein said inhibitory sequence is operably linked to a promoter that is functional in a plant cell, and wherein said inhibitory sequence has at least 90% sequence identity to a fragment of at least 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides of sequence selected from the group consisting of SEQ ID NOs: 9 to 28, 75 to 82, 86 to 100, 145, and fragments thereof.

Embodiment 82
The tobacco plant, or part thereof, of Embodiment 81, wherein said Nic1 inhibitory sequence is capable of being transcribed as an inhibitory polynucleotide selected from the group consisting of a single-stranded RNA polynucleotide, a double-stranded RNA polynucleotide, and a combination thereof.

Embodiment 83

The tobacco plant, or part thereof, of Embodiment 81, wherein said promoter is selected from the group consisting of a constitutive promoter, an inducible promoter, and a tissue-preferred promoter.

Embodiment 84

The tobacco plant, or part thereof, of Embodiment 81, wherein said promoter is a root-specific promoter.

Embodiment 85

A tobacco plant, or part thereof, comprising a heterologous expression cassette comprising a Nic1 inhibitory sequence of a gene comprising a sequence selected from the group consisting of SEQ ID NOs: 13, 28, 33, 48, 82, 86, 87, 101, 102, 145, and 146, and fragments thereof, wherein said inhibitory sequence is operably linked to a promoter that is functional in a plant cell, and wherein said inhibitory sequence has at least 90% sequence identity to a fragment of at least 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides of sequence selected from the group consisting of SEQ ID NOs: 13, 28, 33, 48, 82, 86, 87, 101, 102, 145, and 146, and fragments thereof.

Embodiment 86

A method of introgressing a low nicotine trait into a tobacco variety, said method comprising:
 a. crossing a first tobacco variety comprising a low nicotine trait with a second tobacco variety without said low nicotine trait to produce one or more progeny tobacco plants;
 b. genotyping the one or more progeny tobacco plants for a polymorphic marker linked to said low nicotine trait, wherein said polymorphic marker is in a chromosomal interval flanked by any two of polymorphic loci listed in Table 3 or flanked by any two of polymorphic loci listed in Table 4; and
 c. selecting a progeny tobacco plant comprising the low nicotine trait.

Embodiment 87

The method of Embodiment 86, wherein the method further comprises backcrossing said selected progeny tobacco plant with said second tobacco variety.

Embodiment 88

The method of Embodiment 86, wherein the method further comprises:
 d. crossing the selected progeny plant with itself or with the second tobacco variety to produce one or more further progeny tobacco plants; and
 e. selecting a further progeny tobacco plant comprising the low nicotine trait.

Embodiment 89

The method of Embodiment 88, wherein the step (e) of selecting comprises marker-assisted selection.

Embodiment 90

The method of Embodiment 86, wherein the method produces a single gene conversion comprising said low nicotine trait.

Embodiment 91

The method of Embodiment 86, wherein the second tobacco variety is an elite variety.

Embodiment 92

The method of Embodiment 86, wherein the genotyping involves one or more molecular marker assays.

Embodiment 93

The method of Embodiment 86, wherein the polymorphic marker comprises a polymorphism selected from the group consisting of single nucleotide polymorphisms (SNPs), insertions or deletions in DNA sequence (Indels), simple sequence repeats of DNA sequence (SSRs), a restriction fragment length polymorphism (RFLP), and a tag SNP.

Embodiment 94

The method of Embodiment 86, wherein the genotyping comprises assaying for the presence or absence of a nucleic acid sequence located within a sequence having at least 80%, at least 85%, at least 90%, at least 95%, at least 97%, at least 98%, at least 99% identity to a sequence selected from the group consisting of SEQ ID NOs: 9 to 28, 75 to 82, 86 to 100, 145, and fragments thereof.

Embodiment 95

The method of Embodiment 86, wherein the genotyping comprises assaying for the presence or absence of a nucleic acid sequence located within a sequence having at least 80%, at least 85%, at least 90%, at least 95%, at least 97%, at least 98%, at least 99% identity to a sequence selected from the group consisting of SEQ ID Nos: 13, 28, 33, 48, 82, 86, 87, 101, 102, 145, and 146, and fragments thereof.

Embodiment 96

The method of Embodiment 86, wherein the first tobacco variety is LA Burley 21.

Embodiment 97

The method of Embodiment 86, wherein the selected progeny tobacco plant comprises a shorter chromosome deletion at Nic1 locus compared to LA Burley 21.

Embodiment 98

A method of introgressing a low nicotine trait into a tobacco variety, said method comprising:
a. crossing a first tobacco variety comprising a low nicotine trait with a second tobacco variety without said low nicotine trait to produce one or more progeny tobacco plants;
b. genotyping the one or more progeny tobacco plants for a polymorphic marker linked to said low nicotine trait, wherein said polymorphic marker is within 20 cM of any one of polymorphic loci listed in Table 3 and Table 4, or is any one of SEQ ID Nos. 131 to 144; and
c. selecting a progeny tobacco plant comprising the low nicotine trait.

Embodiment 99

The method of Embodiment 98, wherein the genotyping comprises assaying for the presence or absence of a nucleic acid sequence located within a sequence having at least 80%, at least 85%, at least 90%, at least 95%, at least 97%, at least 98%, at least 99% identity to a sequence selected from the group consisting of SEQ ID NOs: 9 to 28, 75 to 82, 86 to 100, 145, and fragments thereof.

Embodiment 100

The method of Embodiment 98, wherein the genotyping comprises assaying for the presence or absence of a nucleic acid sequence located within a sequence having at least 80%, at least 85%, at least 90%, at least 95%, at least 97%, at least 98%, at least 99% identity to a sequence selected from the group consisting of SEQ ID NOs: 13, 28, 33, 48, 82, 86, 87, 101, 102, 145, and 146, and fragments thereof.

Embodiment 101

A method of selecting a tobacco plant having a low nicotine trait, said method comprising:
a. isolating nucleic acids from a collection of tobacco germplasm;
b. assaying the nucleic acids for one or more markers closely linked to Nic1 locus or Nic2 locus; and c. selecting a tobacco plant having a low nicotine trait based on the marker assay.

Embodiment 102

The method of Embodiment 101, wherein the one or more markers are within about 20 cM, 10 cM, 5 cM, 4 cM, 3 cM, 2 cM, 1 cM, 0.5 cM, or less than 0.5 cM of any one of polymorphic loci listed in Table 3 and Table 4, or any one of SEQ ID Nos. 131 to 144.

Embodiment 103

The method of Embodiment 101, wherein the assaying comprises assaying for the presence or absence of a nucleic acid sequence located within a sequence having at least 80%, at least 85%, at least 90%, at least 95%, at least 97%, at least 98%, at least 99% identity to a sequence selected from the group consisting of SEQ ID NOs: 9 to 28, 75 to 82, 86 to 100, 145, and fragments thereof.

Embodiment 104

The method of Embodiment 101, wherein the assaying comprises assaying for the presence or absence of a nucleic acid sequence located within a sequence having at least 80%, at least 85%, at least 90%, at least 95%, at least 97%, at least 98%, at least 99% identity to a sequence selected from the group consisting of SEQ ID NOs: 13, 28, 33, 48, 82, 86, 87, 101, 102, 145, and 146, and fragments thereof.

Embodiment 105

The method of Embodiment 101, wherein the method further comprises determining the nicotine level of said selected plant to confirm said low nicotine trait.

Embodiment 106

The method of Embodiment 101, wherein the collection of tobacco germplasm is a haploid breeding population.

Embodiment 107

A tobacco plant, or part thereof, comprising a first chromosomal deletion flanked by and not comprising any two of Nic1 Marker Nos. 1 to 207, a second chromosomal deletion flanked by and not comprising any two of Nic2 Marker Nos. 1 to 340, or both said first and said second chromosomal deletions, wherein said tobacco plant is capable of producing leaves having a USDA grade index value of 50 or more, 55 or more, 60 or more, 65 or more, 70 or more, 75 or more, 80 or more, 85 or more, 90 or more, or 95 or more.

Embodiment 108

The tobacco plant, or part thereof, of Embodiment 107, wherein said tobacco plant comprises a nicotine level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, and less than 0.05%.

Embodiment 109

The tobacco plant, or part thereof, of Embodiment 107, wherein said first chromosomal deletion is flanked by and not comprising any two of Nic1 Marker Nos. 1 to 20, 21 to 40, 41 to 60, 61 to 80, 81 to 100, 101 to 120, 121 to 140, 141 to 160, 161 to 180, 181 to 200, or 201 to 207.

Embodiment 110

The tobacco plant, or part thereof, of Embodiment 107, wherein said first chromosomal deletion is flanked by and not comprising any two of Nic1 Marker Nos. 1 to 10, 11 to 20, 21 to 30, 31 to 40, 41 to 50, 51 to 60, 61 to 70, 71 to 80, 81 to 90, 91 to 100, 101 to 110, 111 to 120, 121 to 130, 131 to 140, 141 to 150, 151 to 160, 161 to 170, 171 to 180, 181 to 190, 191 to 200, or 201 to 207.

Embodiment 111

The tobacco plant, or part thereof, of Embodiment 107, wherein said second chromosomal deletion is flanked by and not comprising any two of Nic2 Marker Nos. 1 to 20, 21 to 40, 41 to 60, 61 to 80, 81 to 100, 101 to 120, 121 to 140, 141 to 160, 161 to 180, 181 to 200, 201 to 220, 221 to 240, 241 to 260, 261 to 280, 281 to 300, 301 to 320, or 321 to 340.

Embodiment 112

The tobacco plant, or part thereof, of Embodiment 107, wherein said second chromosomal deletion is flanked by and not comprising any two of Nic2 Marker Nos. 1 to 10, 11 to 20, 21 to 30, 31 to 40, 41 to 50, 51 to 60, 61 to 70, 71 to 80, 81 to 90, 91 to 100, 101 to 110, 111 to 120, 121 to 130, 131 to 140, 141 to 150, 151 to 160, 161 to 170, 171 to 180, 181 to 190, 191 to 200, 201 to 210, 211 to 220, 221 to 230, 231 to 240, 241 to 250, 251 to 260, 261 to 270, 271 to 280, 281 to 290, 291 to 300, 301 to 310, 311 to 320, 321 to 330, or 331 to 340.

Embodiment 113

A tobacco plant, or part thereof, comprising a mutation selected from the group consisting of a first chromosomal deletion flanked by and not comprising any two of Nic1 Marker Nos. 1 to 207, a second chromosomal deletion flanked by and not comprising any two of Nic2 Marker Nos. 1 to 340, and both said first and said second chromosomal deletions, wherein said tobacco plant is capable of producing leaves having a USDA grade index value comparable to that of a control plant when grown in similar growth conditions, wherein said control plant shares an essentially identical genetic background with said tobacco plant except said mutation.

Embodiment 114

The tobacco plant, or part thereof, of Embodiment 113, wherein said tobacco plant comprises nicotine at a level below 1%, below 2%, below 5%, below 8%, below 10%, below 12%, below 15%, below 20%, below 25%, below 30%, below 40%, below 50%, below 60%, below 70%, or below 80% of the nicotine level of said control plant when grown in similar growth conditions.

Embodiment 115

A population of the tobacco plants of any one of Embodiments 107 to 114.

Embodiment 116

Cured tobacco material from the tobacco plant of any one of claims 107 to 114.

Embodiment 117

The cured tobacco material of Embodiment 116, wherein said cured tobacco material is made by a curing process selected from the group consisting of flue curing, air curing, fire curing, and sun curing.

Embodiment 118

A tobacco blend comprising the cured tobacco material of claim 116.

Embodiment 119

The tobacco blend of Embodiment 118, wherein the cured tobacco material constitutes about at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of cured tobacco in said tobacco blend by weight.

Embodiment 120

The tobacco blend of Embodiment 118, wherein the cured tobacco material constitutes about at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of cured tobacco in said tobacco blend by volume.

Embodiment 121

A tobacco product comprising the cured tobacco material of claim 116.

Embodiment 122

The tobacco product of Embodiment 121, wherein the tobacco product is selected from the group consisting of a cigarette, a cigarillo, a non-ventilated recess filter cigarette, a vented recess filter cigarette, a cigar, snuff, pipe tobacco, cigar tobacco, cigarette tobacco, chewing tobacco, leaf tobacco, shredded tobacco, and cut tobacco.

Embodiment 123

The tobacco product of Embodiment 121, wherein the smokeless tobacco product is selected from the group consisting of loose leaf chewing tobacco, plug chewing tobacco, moist snuff, and nasal snuff.

Having now generally described the disclosure, the same will be more readily understood through reference to the following examples that are provided by way of illustration, and are not intended to be limiting of the present disclosure, unless specified.

EXAMPLES

Example 1

Whole Genome Sequencing of Tobacco Lines Having Low Alkaloid

Whole genome sequencing was used to determine the genetic lesion underlying the nic1 mutation in Low Alkaloid (LA) Burley 21. Four tobacco lines were sequenced. These are LA Burley 21 (nic1 nic2, Average nicotine ~0.3% on a dry weight basis (Range~0.2-0.6%)), Low Intermediate (LI) Burley 21 (nic1 Nic2, Average nicotine ~2.3% (Range~1.5-3.0%)), High Intermediate (HI) Burley 21(Nic1 nic2, Average nicotine ~3.7% (Range~2.5-5.0%)), and wild-type Burley 21 (also referred to as "BU21") (Nic1 Nic2, Average nicotine ~4.7% (Range~4.0-6.0%)). LA Burley 21 (also referred to as "LA BU21") is a low total alkaloid line produced by incorporation of a low alkaloid gene(s) from a Cuban cigar variety into Burley 21 through several backcrosses (Legg et al. 1970).

Genomic DNA samples were prepared from tobacco leaves. Green leaf tissue from three plants each belonging to BU21 and LA BU21, as well as the High and Low Intermediates (HI BU21 and LI BU21, respectively) were collected. The tissue was flash frozen in liquid nitrogen and stored at −80° C. The stored tissue was ground in liquid Nitrogen and equal amount of tissue from the three plants belonging to each of the four lines was pooled together (~10 g total final weight) for sequencing.

DNA library preparation and sequencing were performed following standard industry protocols, which include, e.g., shearing of DNA to create paired end libraries with average insert size of 500 bp. The raw sequences were mapped to a proprietary TN90 genome, and Single Nucleotide Polymorphisms (SNPs) as well as Insertions and Deletions (InDels) were identified using a whole genome variant detection pipeline. The variant detection pipeline performs trimming and filtering of raw sequencing data based on sequence quality, followed by selection of reads with minimum length of 75 bp and maximum number of 2 unknown bases. These reads were then mapped to Altria's proprietary tobacco (TN90) genome using the software gaMap v2.0.0 (BETA). Only mapped reads with a quality score of at least 40 were further used in SNP and InDel detection using software gaVariant v.2.0.0 BETA. Only SNPs and InDels with a minimum variant quality of 37, genotype quality of 85 and a coverage depth of 7× were included for further analyses. The number of paired end sequencing reads, filtered reads, mapped reads, as well as percentage of mapped reads for each of the four lines are provided in Table 1. The mean coverage for the 4 varieties ranges between 22-40×, which exceeds the recommended coverage for variant detection (approximately 20×). Table 2 provides details on the number of SNPs and InDels detected in each of the four lines.

TABLE 1

Whole-genome sequencing statistics of the four sequenced Burley lines.

| Sample | Raw reads | Reads filtered | reads mapped | % Filtered | % Mapped |
| --- | --- | --- | --- | --- | --- |
| BU21 | 1,030,266,578 | 987,988,031 | 815,146,282 | 95.9 | 82.51 |
| HI BU21 | 928,747,952 | 889,038,519 | 738,942,909 | 95.72 | 83.12 |
| LI BU21 | 838,709,526 | 800,400,171 | 663,625,600 | 95.43 | 82.91 |
| LA BU21 | 792,837,196 | 755,706,369 | 621,019,698 | 95.32 | 82.18 |
| Total | 3,590,561,252 | 3,433,133,090 | 2,838,734,489 | 95.59 | 82.68 |

TABLE 2

Genotyping statistics of the four sequenced Burley lines.

| Sample | SNPs | Insertions | Deletions | % SNPs | % Insertions | % Deletions |
| --- | --- | --- | --- | --- | --- | --- |
| BU21 | 2,349,123 | 304,814 | 397,514 | 76.984 | 9.98915 | 13.02705 |
| HI BU21 | 2,253,395 | 292,635 | 386,493 | 76.842 | 9.97895 | 13.17954 |
| LI BU21 | 2,138,321 | 276,921 | 371,838 | 76.723 | 9.93588 | 13.34149 |
| LA BU21 | 2,083,729 | 265,561 | 358,655 | 76.949 | 9.80674 | 13.24455 |
| Total | 8,824,568 | 1,139,931 | 1,514,500 | 76.8745 | 9.92768 | 13.19816 |

Example 2

Analysis of the Genome Sequences to Identify Nic1 and Nic2 Loci

The genome sequences from Example 1 were analyzed to identify the nic1 and nic2 mutations in LA BU21. The sequences were first analyzed at Nic2 locus. The Nic2 locus was previously reported by Shoji et. al (2010) to comprise a deletion of 7 Ethylene Response Factor (ERF) genes. These deleted ERF genes were mapped to a single contiguous region of the TN90 genome. We scanned the sequencing data of BU21, HI BU21, LI BU21 and LA BU21 and identified that the variant profile in this region of the genome consists of homozygous reference (TN90) allele genotypes across BU21 and LI BU21, and missing data across HI BU21 and LA BU21. This indicates that Nic2 deletion is represented in the variant genotypes as missing data.

Previous literature suggests that Nic1 and Nic2 loci likely contain duplicated genes each originating from one of the progenitor species, *Nicotiana tomentosiformis* or *N. sylvestris* (Hibi et al., 1994). Further, Shoji et al. (2010) reported that Nic2 locus is derived from *N. tomentosiformis*, and that nic2 is a deletion. The similar nature of their origin suggested that nic1 may also be a deletion. A custom perl script was written to detect a pattern of homozygous or heterozygous reference allele calls in BU21 and HI BU21, and missing data in LI BU21 and LA BU21. The custom perl script detected a total of 14035 scaffolds with nearly 37916 variants sites total that match the pattern of missing data in LA BU21 and LI BU21 and homozygous genotypes in HI BU21 and BU21. The mean number of variants observed per scaffold is nearly 3 (2.701). One contiguous region or scaffold (Scaffold0002504, SEQ ID No: 1) contains 207 variant sites with this pattern (Table 3). Hence, this outlier scaffold has 76.67 times the number of variants with the specified pattern compared to the mean number of variants across the remaining scaffolds. Scaffold0002504 provides the first indication of the location of Nic1 locus.

Based on the coverage of the reads across scaffolds, no sequencing bias was observed to account for the absence of reads in LI BU21 and LA BU21. Further, at the known Nic2 locus (Scaffold0000549, SEQ ID No: 2), a similar pattern was observed where LA BU21 and HI BU21 show missing data and BU21 and LI BU21 show homozygous reference allele calls (340 sites on Scaffold0000549 compared to 2.49 sites observed in all scaffolds exhibiting such a pattern of variant sites) (Table 4).

TABLE 3

Polymorphic sites in a Nic1 deletion segment, NT1.0-Scaffold0002504. POS indicates the nucleotide position of each polymorphic site on Scaffold0002504. REF refers to the sequence of a reference TN90 allele. ALT refers to a sequence polymorphism found in K326, Narrow Leaf Madole, or Oriental type. "0/0" refers to homozygous for the reference TN90 allele while "./." refers to missing data (e.g., deletion).

| Nic1 Marker No. | POS | REF | ALT | BU21 | HI | LI | LA |
|---|---|---|---|---|---|---|---|
| 1 | 240 | T | A | 0/0 | 0/0 | ./. | ./. |
| 2 | 1750 | CA | C | 0/0 | 0/0 | ./. | ./. |
| 3 | 2064 | G | A | 0/0 | 0/0 | ./. | ./. |
| 4 | 2671 | G | A | 0/0 | 0/0 | ./. | ./. |
| 5 | 2678 | G | T | 0/0 | 0/0 | ./. | ./. |
| 6 | 5174 | G | T | 0/0 | 0/0 | ./. | ./. |
| 7 | 5176 | A | C | 0/0 | 0/0 | ./. | ./. |
| 8 | 5781 | C | T | 0/0 | 0/0 | ./. | ./. |
| 9 | 5812 | A | G | 0/0 | 0/0 | ./. | ./. |
| 10 | 6312 | G | T | 0/0 | 0/0 | ./. | ./. |
| 11 | 6349 | T | G | 0/0 | 0/0 | ./. | ./. |
| 12 | 6373 | T | C | 0/0 | 0/0 | ./. | ./. |
| 13 | 8028 | T | G | 0/0 | 0/0 | ./. | ./. |
| 14 | 12004 | AT | A | 0/0 | 0/0 | ./. | ./. |
| 15 | 12668 | T | C | 0/0 | 0/0 | ./. | ./. |
| 16 | 12939 | A | G | 0/0 | 0/0 | ./. | ./. |
| 17 | 13171 | G | T | 0/0 | 0/0 | ./. | ./. |
| 18 | 13644 | G | T | 0/0 | 0/0 | ./. | ./. |
| 19 | 14078 | G | A | 0/0 | 0/0 | ./. | ./. |
| 20 | 14085 | T | C | 0/0 | 0/0 | ./. | ./. |
| 21 | 29126 | G | T | 0/0 | 0/0 | ./. | ./. |
| 22 | 46969 | G | A | 0/0 | 0/0 | ./. | ./. |
| 23 | 54856 | C | T | 0/0 | 0/0 | ./. | ./. |
| 24 | 54923 | T | C | 0/0 | 0/0 | ./. | ./. |
| 25 | 63743 | T | C | 0/0 | 0/0 | ./. | ./. |
| 26 | 69020 | G | T | 0/0 | 0/0 | ./. | ./. |
| 27 | 78215 | A | G | 0/0 | 0/0 | ./. | ./. |
| 28 | 87817 | T | G | 0/0 | 0/0 | ./. | ./. |
| 29 | 91989 | A | G | 0/0 | 0/0 | ./. | ./. |
| 30 | 92936 | C | G | 0/0 | 0/0 | ./. | ./. |
| 31 | 104894 | G | T | 0/0 | 0/0 | ./. | ./. |
| 32 | 108471 | A | G | 0/0 | 0/0 | ./. | ./. |
| 33 | 108492 | G | A | 0/0 | 0/0 | ./. | ./. |
| 34 | 108503 | A | C | 0/0 | 0/0 | ./. | ./. |
| 35 | 109907 | A | C | 0/0 | 0/0 | ./. | ./. |

TABLE 3-continued

Polymorphic sites in a Nic1 deletion segment, NT1.0-Scaffold0002504. POS indicates the nucleotide position of each polymorphic site on Scaffold0002504. REF refers to the sequence of a reference TN90 allele. ALT refers to a sequence polymorphism found in K326, Narrow Leaf Madole, or Oriental type. "0/0" refers to homozygous for the reference TN90 allele while "./." refers to missing data (e.g., deletion).

| Nic1 Marker No. | POS | REF | ALT | BU21 | HI | LI | LA |
|---|---|---|---|---|---|---|---|
| 36 | 112193 | A | T | 0/0 | 0/0 | ./. | ./. |
| 37 | 114778 | C | T | 0/0 | 0/0 | ./. | ./. |
| 38 | 114852 | C | T | 0/0 | 0/0 | ./. | ./. |
| 39 | 117178 | A | G | 0/0 | 0/0 | ./. | ./. |
| 40 | 123634 | G | A | 0/0 | 0/0 | ./. | ./. |
| 41 | 130508 | A | G | 0/0 | 0/0 | ./. | ./. |
| 42 | 130966 | T | C | 0/0 | 0/0 | ./. | ./. |
| 43 | 131000 | C | T | 0/0 | 0/0 | ./. | ./. |
| 44 | 131045 | C | A | 0/0 | 0/0 | ./. | ./. |
| 45 | 134007 | A | G | 0/0 | 0/0 | ./. | ./. |
| 46 | 134046 | A | G | 0/0 | 0/0 | ./. | ./. |
| 47 | 136601 | C | T | 0/0 | 0/0 | ./. | ./. |
| 48 | 136884 | GT | G | 0/0 | 0/0 | ./. | ./. |
| 49 | 150080 | G | A | 0/0 | 0/0 | ./. | ./. |
| 50 | 150585 | T | A | 0/0 | 0/0 | ./. | ./. |
| 51 | 153975 | T | C | 0/0 | 0/0 | ./. | ./. |
| 52 | 159146 | A | G | 0/0 | 0/0 | ./. | ./. |
| 53 | 162586 | C | T | 0/0 | 0/0 | ./. | ./. |
| 54 | 163446 | G | A | 0/0 | 0/0 | ./. | ./. |
| 55 | 163641 | T | C | 0/0 | 0/0 | ./. | ./. |
| 56 | 167356 | T | C | 0/0 | 0/0 | ./. | ./. |
| 57 | 171095 | A | T | 0/0 | 0/0 | ./. | ./. |
| 58 | 181539 | A | G | 0/0 | 0/0 | ./. | ./. |
| 59 | 182327 | C | T | 0/0 | 0/0 | ./. | ./. |
| 60 | 190959 | C | T | 0/0 | 0/0 | ./. | ./. |
| 61 | 198368 | G | A | 0/0 | 0/0 | ./. | ./. |
| 62 | 198393 | A | G | 0/0 | 0/0 | ./. | ./. |
| 63 | 204573 | G | C | 0/0 | 0/0 | ./. | ./. |
| 64 | 205220 | A | G | 0/0 | 0/0 | ./. | ./. |
| 65 | 205252 | C | T | 0/0 | 0/0 | ./. | ./. |
| 66 | 206301 | C | A | 0/0 | 0/0 | ./. | ./. |
| 67 | 206500 | G | A | 0/0 | 0/0 | ./. | ./. |
| 68 | 206634 | A | C | 0/0 | 0/0 | ./. | ./. |
| 69 | 207061 | A | G | 0/0 | 0/0 | ./. | ./. |
| 70 | 207101 | G | A | 0/0 | 0/0 | ./. | ./. |
| 71 | 207131 | T | G | 0/0 | 0/0 | ./. | ./. |
| 72 | 207181 | T | A | 0/0 | 0/0 | ./. | ./. |
| 73 | 207204 | C | G | 0/0 | 0/0 | ./. | ./. |
| 74 | 207512 | C | A | 0/0 | 0/0 | ./. | ./. |
| 75 | 208518 | A | C | 0/0 | 0/0 | ./. | ./. |
| 76 | 208522 | C | T | 0/0 | 0/0 | ./. | ./. |
| 77 | 208556 | T | C | 0/0 | 0/0 | ./. | ./. |
| 78 | 208572 | T | C | 0/0 | 0/0 | ./. | ./. |
| 79 | 209297 | T | C | 0/0 | 0/0 | ./. | ./. |
| 80 | 209315 | C | T | 0/0 | 0/0 | ./. | ./. |
| 81 | 209661 | C | T | 0/0 | 0/0 | ./. | ./. |
| 82 | 209674 | T | C | 0/0 | 0/0 | ./. | ./. |
| 83 | 210485 | T | G | 0/0 | 0/0 | ./. | ./. |
| 84 | 211269 | T | C | 0/0 | 0/0 | ./. | ./. |
| 85 | 216116 | C | T | 0/0 | 0/0 | ./. | ./. |
| 86 | 222130 | G | A | 0/0 | 0/0 | ./. | ./. |
| 87 | 224309 | G | T | 0/0 | 0/0 | ./. | ./. |
| 88 | 224568 | C | T | 0/0 | 0/0 | ./. | ./. |
| 89 | 232343 | C | T | 0/0 | 0/0 | ./. | ./. |
| 90 | 238580 | C | T | 0/0 | 0/0 | ./. | ./. |
| 91 | 239069 | T | A | 0/0 | 0/0 | ./. | ./. |
| 92 | 242812 | A | T | 0/0 | 0/0 | ./. | ./. |
| 93 | 243675 | A | G | 0/0 | 0/0 | ./. | ./. |
| 94 | 244449 | A | G | 0/0 | 0/0 | ./. | ./. |
| 95 | 244950 | T | C | 0/0 | 0/0 | ./. | ./. |
| 96 | 245176 | A | G | 0/0 | 0/0 | ./. | ./. |
| 97 | 254755 | G | A | 0/0 | 0/0 | ./. | ./. |
| 98 | 255169 | C | T | 0/0 | 0/0 | ./. | ./. |
| 99 | 259166 | G | A | 0/0 | 0/0 | ./. | ./. |
| 100 | 271206 | G | A | 0/0 | 0/0 | ./. | ./. |

TABLE 3-continued

Polymorphic sites in a Nic1 deletion segment, NT1.0-Scaffold0002504. POS indicates the nucleotide position of each polymorphic site on Scaffold0002504. REF refers to the sequence of a reference TN90 allele. ALT refers to a sequence polymorphism found in K326, Narrow Leaf Madole, or Oriental type. "0/0" refers to homozygous for the reference TN90 allele while "./." refers to missing data (e.g., deletion).

| Nic1 Marker No. | POS | REF | ALT | BU21 | HI | LI | LA |
|---|---|---|---|---|---|---|---|
| 101 | 272201 | T | C | 0/0 | 0/0 | ./. | ./. |
| 102 | 273944 | T | C | 0/0 | 0/0 | ./. | ./. |
| 103 | 276518 | C | T | 0/0 | 0/0 | ./. | ./. |
| 104 | 276838 | T | A | 0/0 | 0/0 | ./. | ./. |
| 105 | 281675 | G | T | 0/0 | 0/0 | ./. | ./. |
| 106 | 284726 | G | T | 0/0 | 0/0 | ./. | ./. |
| 107 | 286609 | C | T | 0/0 | 0/0 | ./. | ./. |
| 108 | 286915 | A | G | 0/0 | 0/0 | ./. | ./. |
| 109 | 286966 | T | A | 0/0 | 0/0 | ./. | ./. |
| 110 | 286987 | A | G | 0/0 | 0/0 | ./. | ./. |
| 111 | 293036 | A | G | 0/0 | 0/0 | ./. | ./. |
| 112 | 300478 | G | T | 0/0 | 0/0 | ./. | ./. |
| 113 | 300631 | C | T | 0/0 | 0/0 | ./. | ./. |
| 114 | 300759 | A | T | 0/0 | 0/0 | ./. | ./. |
| 115 | 301119 | G | A | 0/0 | 0/0 | ./. | ./. |
| 116 | 303538 | A | C | 0/0 | 0/0 | ./. | ./. |
| 117 | 304744 | A | G | 0/0 | 0/0 | ./. | ./. |
| 118 | 306236 | C | T | 0/0 | 0/0 | ./. | ./. |
| 119 | 308259 | C | A | 0/0 | 0/0 | ./. | ./. |
| 120 | 313448 | A | G | 0/0 | 0/0 | ./. | ./. |
| 121 | 317046 | C | G | 0/0 | 0/0 | ./. | ./. |
| 122 | 318876 | GGGGGGT | G | 0/0 | 0/0 | ./. | ./. |
| 123 | 320878 | G | T | 0/0 | 0/0 | ./. | ./. |
| 124 | 321339 | T | G | 0/0 | 0/0 | ./. | ./. |
| 125 | 321361 | A | G | 0/0 | 0/0 | ./. | ./. |
| 126 | 321363 | C | T | 0/0 | 0/0 | ./. | ./. |
| 127 | 321532 | A | C | 0/0 | 0/0 | ./. | ./. |
| 128 | 324556 | A | G | 0/0 | 0/0 | ./. | ./. |
| 129 | 324990 | G | A | 0/0 | 0/0 | ./. | ./. |
| 130 | 329545 | T | A | 0/0 | 0/0 | ./. | ./. |
| 131 | 349886 | T | C | 0/0 | 0/0 | ./. | ./. |
| 132 | 350146 | A | C | 0/0 | 0/0 | ./. | ./. |
| 133 | 350163 | A | G | 0/0 | 0/0 | ./. | ./. |
| 134 | 350515 | T | G | 0/0 | 0/0 | ./. | ./. |
| 135 | 351620 | A | C | 0/0 | 0/0 | ./. | ./. |
| 136 | 353656 | A | G | 0/0 | 0/0 | ./. | ./. |
| 137 | 354639 | CT | C | 0/0 | 0/0 | ./. | ./. |
| 138 | 366150 | AG | A | 0/0 | 0/0 | ./. | ./. |
| 139 | 388388 | T | G | 0/0 | 0/0 | ./. | ./. |
| 140 | 390555 | G | A | 0/0 | 0/0 | ./. | ./. |
| 141 | 391708 | C | T | 0/0 | 0/0 | ./. | ./. |
| 142 | 392358 | G | C | 0/0 | 0/0 | ./. | ./. |
| 143 | 392712 | T | C | 0/0 | 0/0 | ./. | ./. |
| 144 | 401096 | G | T | 0/0 | 0/0 | ./. | ./. |
| 145 | 401445 | G | C | 0/0 | 0/0 | ./. | ./. |
| 146 | 404189 | A | C | 0/0 | 0/0 | ./. | ./. |
| 147 | 406610 | T | G | 0/0 | 0/0 | ./. | ./. |
| 148 | 407131 | C | T | 0/0 | 0/0 | ./. | ./. |
| 149 | 411268 | A | C | 0/0 | 0/0 | ./. | ./. |
| 150 | 412538 | T | A | 0/0 | 0/0 | ./. | ./. |
| 151 | 412550 | G | T | 0/0 | 0/0 | ./. | ./. |
| 152 | 413003 | A | C | 0/0 | 0/0 | ./. | ./. |
| 153 | 413373 | A | T | 0/0 | 0/0 | ./. | ./. |
| 154 | 413437 | C | T | 0/0 | 0/0 | ./. | ./. |
| 155 | 415425 | A | G | 0/0 | 0/0 | ./. | ./. |
| 156 | 415449 | A | C | 0/0 | 0/0 | ./. | ./. |
| 157 | 415458 | T | G | 0/0 | 0/0 | ./. | ./. |
| 158 | 417103 | A | C | 0/0 | 0/0 | ./. | ./. |
| 159 | 418099 | G | A | 0/0 | 0/0 | ./. | ./. |
| 160 | 418558 | A | G | 0/0 | 0/0 | ./. | ./. |
| 161 | 423778 | T | C | 0/0 | 0/0 | ./. | ./. |
| 162 | 430030 | G | T | 0/0 | 0/0 | ./. | ./. |
| 163 | 437935 | T | C | 0/0 | 0/0 | ./. | ./. |
| 164 | 440647 | G | A | 0/0 | 0/0 | ./. | ./. |

TABLE 3-continued

Polymorphic sites in a Nic1 deletion segment, NT1.0-Scaffold0002504. POS indicates the nucleotide position of each polymorphic site on Scaffold0002504. REF refers to the sequence of a reference TN90 allele. ALT refers to a sequence polymorphism found in K326, Narrow Leaf Madole, or Oriental type. "0/0" refers to homozygous for the reference TN90 allele while "./." refers to missing data (e.g., deletion).

| Nic1 Marker No. | POS | REF | ALT | BU21 | HI | LI | LA |
|---|---|---|---|---|---|---|---|
| 165 | 440664 | C | T | 0/0 | 0/0 | ./. | ./. |
| 166 | 442849 | T | A | 0/0 | 0/0 | ./. | ./. |
| 167 | 445778 | A | G | 0/0 | 0/0 | ./. | ./. |
| 168 | 446871 | T | C | 0/0 | 0/0 | ./. | ./. |
| 169 | 447998 | A | T | 0/0 | 0/0 | ./. | ./. |
| 170 | 450145 | A | G | 0/0 | 0/0 | ./. | ./. |
| 171 | 452523 | A | G | 0/0 | 0/0 | ./. | ./. |
| 172 | 452968 | G | A | 0/0 | 0/0 | ./. | ./. |
| 173 | 452987 | T | C | 0/0 | 0/0 | ./. | ./. |
| 174 | 453033 | C | T | 0/0 | 0/0 | ./. | ./. |
| 175 | 453112 | G | A | 0/0 | 0/0 | ./. | ./. |
| 176 | 453174 | T | C | 0/0 | 0/0 | ./. | ./. |
| 177 | 453188 | G | A | 0/0 | 0/0 | ./. | ./. |
| 178 | 454399 | T | C | 0/0 | 0/0 | ./. | ./. |
| 179 | 456245 | A | C | 0/0 | 0/0 | ./. | ./. |
| 180 | 466990 | T | C | 0/0 | 0/0 | ./. | ./. |
| 181 | 473415 | C | T | 0/0 | 0/0 | ./. | ./. |
| 182 | 479185 | G | A | 0/0 | 0/0 | ./. | ./. |
| 183 | 481321 | T | C | 0/0 | 0/0 | ./. | ./. |
| 184 | 481329 | T | C | 0/0 | 0/0 | ./. | ./. |
| 185 | 481922 | T | C | 0/0 | 0/0 | ./. | ./. |
| 186 | 485778 | G | A | 0/0 | 0/0 | ./. | ./. |
| 187 | 486466 | A | G | 0/0 | 0/0 | ./. | ./. |
| 188 | 487632 | G | A | 0/0 | 0/0 | ./. | ./. |
| 189 | 495057 | TA | T | 0/0 | 0/0 | ./. | ./. |
| 190 | 496107 | G | A | 0/0 | 0/0 | ./. | ./. |
| 191 | 496129 | G | T | 0/0 | 0/0 | ./. | ./. |
| 192 | 498389 | C | T | 0/0 | 0/0 | ./. | ./. |
| 193 | 502623 | G | T | 0/0 | 0/0 | ./. | ./. |
| 194 | 515727 | T | C | 0/0 | 0/0 | ./. | ./. |
| 195 | 517529 | C | T | 0/0 | 0/0 | ./. | ./. |
| 196 | 521866 | T | C | 0/0 | 0/0 | ./. | ./. |
| 197 | 525885 | AAAAAAAAAAAAAAAAAAAAAAAAAAAAAAAAAAAAAAAAAAAACTTT (SEQ ID NO: 71) | A | 0/0 | 0/0 | ./. | ./. |
| 198 | 528989 | A | G | 0/0 | 0/0 | ./. | ./. |
| 199 | 542757 | A | G | 0/0 | 0/0 | ./. | ./. |
| 200 | 542859 | C | A | 0/0 | 0/0 | ./. | ./. |
| 201 | 543285 | T | C | 0/0 | 0/0 | ./. | ./. |
| 202 | 543440 | G | C | 0/0 | 0/0 | ./. | ./. |
| 203 | 543565 | G | A | 0/0 | 0/0 | ./. | ./. |
| 204 | 543749 | C | T | 0/0 | 0/0 | ./. | ./. |
| 205 | 543771 | T | C | 0/0 | 0/0 | ./. | ./. |
| 206 | 543941 | C | A | 0/0 | 0/0 | ./. | ./. |
| 207 | 543958 | G | C | 0/0 | 0/0 | ./. | ./. |

TABLE 4

Polymorphic sites in a Nic2 deletion segment, NT1.0-Scaffold0000549. REF refers to the sequence of a reference TN90 allele. ALT refers to a sequence polymorphism found in K326, Narrow Leaf Madole, or Oriental type. "0/0" refers to homozygous for the reference TN90 allele while "./." refers to missing data (e.g., deletion).

| Nic2 Marker No. | POS | REF | ALT | BU21 | HI | LI | LA |
|---|---|---|---|---|---|---|---|
| 1 | 8514 | T | A | 0/0 | ./. | 0/0 | ./. |
| 2 | 12287 | A | C | 0/0 | ./. | 0/0 | ./. |
| 3 | 15020 | C | T | 0/0 | ./. | 0/0 | ./. |

TABLE 4-continued

Polymorphic sites in a Nic2 deletion segment, NT1.0-Scaffold0000549. REF refers to the sequence of a reference TN90 allele. ALT refers to a sequence polymorphism found in K326, Narrow Leaf Madole, or Oriental type. "0/0" refers to homozygous for the reference TN90 allele while "./." refers to missing data (e.g., deletion).

| Nic2 Marker No. | POS | REF | ALT | BU21 | HI | LI | LA |
|---|---|---|---|---|---|---|---|
| 4 | 20105 | C | T | 0/0 | ./. | 0/0 | ./. |
| 5 | 21133 | G | T | 0/0 | ./. | 0/0 | ./. |
| 6 | 21182 | A | C | 0/0 | ./. | 0/0 | ./. |
| 7 | 25267 | T | C | 0/0 | ./. | 0/0 | ./. |
| 8 | 27211 | A | G | 0/0 | ./. | 0/0 | ./. |
| 9 | 27965 | T | A | 0/0 | ./. | 0/0 | ./. |
| 10 | 28780 | A | G | 0/0 | ./. | 0/0 | ./. |
| 11 | 28800 | G | A | 0/0 | ./. | 0/0 | ./. |
| 12 | 28976 | T | A | 0/0 | ./. | 0/0 | ./. |
| 13 | 29013 | G | A | 0/0 | ./. | 0/0 | ./. |
| 14 | 31000 | C | T | 0/0 | ./. | 0/0 | ./. |
| 15 | 31074 | T | C | 0/0 | ./. | 0/0 | ./. |
| 16 | 31118 | A | G | 0/0 | ./. | 0/0 | ./. |
| 17 | 31136 | G | A | 0/0 | ./. | 0/0 | ./. |
| 18 | 31930 | T | G | 0/0 | ./. | 0/0 | ./. |
| 19 | 32523 | A | G | 0/0 | ./. | 0/0 | ./. |
| 20 | 33617 | A | C | 0/0 | ./. | 0/0 | ./. |
| 21 | 33661 | A | T | 0/0 | ./. | 0/0 | ./. |
| 22 | 35656 | T | C | 0/0 | ./. | 0/0 | ./. |
| 23 | 35674 | C | T | 0/0 | ./. | 0/0 | ./. |
| 24 | 44008 | C | T | 0/0 | ./. | 0/0 | ./. |
| 25 | 62895 | T | C | 0/0 | ./. | 0/0 | ./. |
| 26 | 62916 | G | A | 0/0 | ./. | 0/0 | ./. |
| 27 | 64381 | A | G | 0/0 | ./. | 0/0 | ./. |
| 28 | 77284 | A | T | 0/0 | ./. | 0/0 | ./. |
| 29 | 77363 | A | G | 0/0 | ./. | 0/0 | ./. |
| 30 | 77909 | G | C | 0/0 | ./. | 0/0 | ./. |
| 31 | 77975 | A | T | 0/0 | ./. | 0/0 | ./. |
| 32 | 77985 | A | G | 0/0 | ./. | 0/0 | ./. |
| 33 | 80196 | C | T | 0/0 | ./. | 0/0 | ./. |
| 34 | 87731 | C | T | 0/0 | ./. | 0/0 | ./. |
| 35 | 87799 | G | A | 0/0 | ./. | 0/0 | ./. |
| 36 | 89358 | G | T | 0/0 | ./. | 0/0 | ./. |
| 37 | 92022 | T | C | 0/0 | ./. | 0/0 | ./. |
| 38 | 92542 | C | A | 0/0 | ./. | 0/0 | ./. |
| 39 | 92675 | C | T | 0/0 | ./. | 0/0 | ./. |
| 40 | 92695 | G | A | 0/0 | ./. | 0/0 | ./. |
| 41 | 94612 | C | G | 0/0 | ./. | 0/0 | ./. |
| 42 | 94683 | C | T | 0/0 | ./. | 0/0 | ./. |
| 43 | 103131 | G | T | 0/0 | ./. | 0/0 | ./. |
| 44 | 108577 | A | G | 0/0 | ./. | 0/0 | ./. |
| 45 | 108967 | G | A | 0/0 | ./. | 0/0 | ./. |
| 46 | 113914 | T | C | 0/0 | ./. | 0/0 | ./. |
| 47 | 118142 | A | T | 0/0 | ./. | 0/0 | ./. |
| 48 | 118151 | T | C | 0/0 | ./. | 0/0 | ./. |
| 49 | 119780 | A | T | 0/0 | ./. | 0/0 | ./. |
| 50 | 121195 | G | A | 0/0 | ./. | 0/0 | ./. |
| 51 | 135236 | G | T | 0/0 | ./. | 0/0 | ./. |
| 52 | 135239 | C | T | 0/0 | ./. | 0/0 | ./. |
| 53 | 135401 | T | C | 0/0 | ./. | 0/0 | ./. |
| 54 | 135683 | T | A | 0/0 | ./. | 0/0 | ./. |
| 55 | 136546 | C | T | 0/0 | ./. | 0/0 | ./. |
| 56 | 136553 | T | G | 0/0 | ./. | 0/0 | ./. |
| 57 | 137241 | G | A | 0/0 | ./. | 0/0 | ./. |
| 58 | 137643 | CT | C | 0/0 | ./. | 0/0 | ./. |
| 59 | 138384 | C | G | 0/0 | ./. | 0/0 | ./. |
| 60 | 138450 | T | C | 0/0 | ./. | 0/0 | ./. |
| 61 | 138457 | G | A | 0/0 | ./. | 0/0 | ./. |
| 62 | 138663 | T | C | 0/0 | ./. | 0/0 | ./. |
| 63 | 138791 | G | A | 0/0 | ./. | 0/0 | ./. |
| 64 | 152981 | C | T | 0/0 | ./. | 0/0 | ./. |
| 65 | 152994 | G | A | 0/0 | ./. | 0/0 | ./. |
| 66 | 158500 | C | T | 0/0 | ./. | 0/0 | ./. |
| 67 | 159059 | G | A | 0/0 | ./. | 0/0 | ./. |
| 68 | 159855 | A | C | 0/0 | ./. | 0/0 | ./. |
| 69 | 162242 | C | A | 0/0 | ./. | 0/0 | ./. |
| 70 | 162272 | T | C | 0/0 | ./. | 0/0 | ./. |

TABLE 4-continued

Polymorphic sites in a Nic2 deletion segment, NT1.0-Scaffold0000549. REF refers to the sequence of a reference TN90 allele. ALT refers to a sequence polymorphism found in K326, Narrow Leaf Madole, or Oriental type. "0/0" refers to homozygous for the reference TN90 allele while "./." refers to missing data (e.g., deletion).

| Nic2 Marker No. | POS | REF | ALT | BU21 | HI | LI | LA |
|---|---|---|---|---|---|---|---|
| 71 | 162616 | T | C | 0/0 | ./. | 0/0 | ./. |
| 72 | 162698 | A | T | 0/0 | ./. | 0/0 | ./. |
| 73 | 163071 | T | C | 0/0 | ./. | 0/0 | ./. |
| 74 | 163389 | T | A | 0/0 | ./. | 0/0 | ./. |
| 75 | 163549 | C | T | 0/0 | ./. | 0/0 | ./. |
| 76 | 169105 | A | C | 0/0 | ./. | 0/0 | ./. |
| 77 | 169578 | A | G | 0/0 | ./. | 0/0 | ./. |
| 78 | 170180 | G | A | 0/0 | ./. | 0/0 | ./. |
| 79 | 170221 | G | T | 0/0 | ./. | 0/0 | ./. |
| 80 | 170292 | A | G | 0/0 | ./. | 0/0 | ./. |
| 81 | 176741 | TG | T | 0/0 | ./. | 0/0 | ./. |
| 82 | 177610 | G | A | 0/0 | ./. | 0/0 | ./. |
| 83 | 189973 | C | A | 0/0 | ./. | 0/0 | ./. |
| 84 | 190622 | T | C | 0/0 | ./. | 0/0 | ./. |
| 85 | 192179 | T | C | 0/0 | ./. | 0/0 | ./. |
| 86 | 192203 | A | G | 0/0 | ./. | 0/0 | ./. |
| 87 | 192520 | G | A | 0/0 | ./. | 0/0 | ./. |
| 88 | 198596 | A | T | 0/0 | ./. | 0/0 | ./. |
| 89 | 210148 | C | T | 0/0 | ./. | 0/0 | ./. |
| 90 | 211238 | A | G | 0/0 | ./. | 0/0 | ./. |
| 91 | 211276 | G | A | 0/0 | ./. | 0/0 | ./. |
| 92 | 211298 | C | T | 0/0 | ./. | 0/0 | ./. |
| 93 | 213281 | C | G | 0/0 | ./. | 0/0 | ./. |
| 94 | 221865 | T | G | 0/0 | ./. | 0/0 | ./. |
| 95 | 224164 | T | A | 0/0 | ./. | 0/0 | ./. |
| 96 | 226470 | A | G | 0/0 | ./. | 0/0 | ./. |
| 97 | 228965 | C | A | 0/0 | ./. | 0/0 | ./. |
| 98 | 230571 | G | A | 0/0 | ./. | 0/0 | ./. |
| 99 | 232100 | C | G | 0/0 | ./. | 0/0 | ./. |
| 100 | 232459 | G | A | 0/0 | ./. | 0/0 | ./. |
| 101 | 234537 | C | T | 0/0 | ./. | 0/0 | ./. |
| 102 | 241822 | G | A | 0/0 | ./. | 0/0 | ./. |
| 103 | 244741 | C | T | 0/0 | ./. | 0/0 | ./. |
| 104 | 246403 | G | A | 0/0 | ./. | 0/0 | ./. |
| 105 | 246519 | C | T | 0/0 | ./. | 0/0 | ./. |
| 106 | 247174 | G | A | 0/0 | ./. | 0/0 | ./. |
| 107 | 252132 | G | A | 0/0 | ./. | 0/0 | ./. |
| 108 | 252717 | T | C | 0/0 | ./. | 0/0 | ./. |
| 109 | 252728 | T | C | 0/0 | ./. | 0/0 | ./. |
| 110 | 255099 | A | G | 0/0 | ./. | 0/0 | ./. |
| 111 | 257486 | C | T | 0/0 | ./. | 0/0 | ./. |
| 112 | 258008 | C | A | 0/0 | ./. | 0/0 | ./. |
| 113 | 258101 | G | A | 0/0 | ./. | 0/0 | ./. |
| 114 | 260634 | C | T | 0/0 | ./. | 0/0 | ./. |
| 115 | 260944 | C | T | 0/0 | ./. | 0/0 | ./. |
| 116 | 261816 | T | C | 0/0 | ./. | 0/0 | ./. |
| 117 | 264558 | T | C | 0/0 | ./. | 0/0 | ./. |
| 118 | 265660 | G | A | 0/0 | ./. | 0/0 | ./. |
| 119 | 275884 | A | G | 0/0 | ./. | 0/0 | ./. |
| 120 | 277012 | A | G | 0/0 | ./. | 0/0 | ./. |
| 121 | 278708 | A | G | 0/0 | ./. | 0/0 | ./. |
| 122 | 278762 | T | C | 0/0 | ./. | 0/0 | ./. |
| 123 | 278781 | G | T | 0/0 | ./. | 0/0 | ./. |
| 124 | 281156 | A | C | 0/0 | ./. | 0/0 | ./. |
| 125 | 282192 | G | T | 0/0 | ./. | 0/0 | ./. |
| 126 | 285956 | A | G | 0/0 | ./. | 0/0 | ./. |
| 127 | 286075 | A | G | 0/0 | ./. | 0/0 | ./. |
| 128 | 290957 | G | T | 0/0 | ./. | 0/0 | ./. |
| 129 | 295851 | C | A | 0/0 | ./. | 0/0 | ./. |
| 130 | 297396 | G | C | 0/0 | ./. | 0/0 | ./. |
| 131 | 298942 | G | T | 0/0 | ./. | 0/0 | ./. |
| 132 | 299095 | A | G | 0/0 | ./. | 0/0 | ./. |
| 133 | 300592 | C | T | 0/0 | ./. | 0/0 | ./. |
| 134 | 301121 | C | G | 0/0 | ./. | 0/0 | ./. |
| 135 | 301147 | C | T | 0/0 | ./. | 0/0 | ./. |
| 136 | 306986 | G | A | 0/0 | ./. | 0/0 | ./. |
| 137 | 310002 | C | T | 0/0 | ./. | 0/0 | ./. |

TABLE 4-continued

Polymorphic sites in a Nic2 deletion segment, NT1.0-Scaffold0000549. REF refers to the sequence of a reference TN90 allele. ALT refers to a sequence polymorphism found in K326, Narrow Leaf Madole, or Oriental type. "0/0" refers to homozygous for the reference TN90 allele while "./." refers to missing data (e.g., deletion).

| Nic2 Marker No. | POS | REF | ALT | BU21 | HI | LI | LA |
|---|---|---|---|---|---|---|---|
| 138 | 314892 | C | T | 0/0 | ./. | 0/0 | ./. |
| 139 | 324211 | G | A | 0/0 | ./. | 0/0 | ./. |
| 140 | 327796 | T | G | 0/0 | ./. | 0/0 | ./. |
| 141 | 330726 | A | G | 0/0 | ./. | 0/0 | ./. |
| 142 | 331046 | G | A | 0/0 | ./. | 0/0 | ./. |
| 143 | 332636 | T | C | 0/0 | ./. | 0/0 | ./. |
| 144 | 336046 | G | C | 0/0 | ./. | 0/0 | ./. |
| 145 | 338147 | C | A | 0/0 | ./. | 0/0 | ./. |
| 146 | 340868 | C | T | 0/0 | ./. | 0/0 | ./. |
| 147 | 341170 | T | A | 0/0 | ./. | 0/0 | ./. |
| 148 | 359439 | T | A | 0/0 | ./. | 0/0 | ./. |
| 149 | 359447 | C | A | 0/0 | ./. | 0/0 | ./. |
| 150 | 362131 | A | G | 0/0 | ./. | 0/0 | ./. |
| 151 | 363467 | G | A | 0/0 | ./. | 0/0 | ./. |
| 152 | 365467 | T | A | 0/0 | ./. | 0/0 | ./. |
| 153 | 367311 | A | G | 0/0 | ./. | 0/0 | ./. |
| 154 | 370267 | G | A | 0/0 | ./. | 0/0 | ./. |
| 155 | 384941 | A | G | 0/0 | ./. | 0/0 | ./. |
| 156 | 393244 | G | T | 0/0 | ./. | 0/0 | ./. |
| 157 | 394169 | T | C | 0/0 | ./. | 0/0 | ./. |
| 158 | 394200 | A | G | 0/0 | ./. | 0/0 | ./. |
| 159 | 394213 | A | C | 0/0 | ./. | 0/0 | ./. |
| 160 | 394228 | G | A | 0/0 | ./. | 0/0 | ./. |
| 161 | 396927 | C | T | 0/0 | ./. | 0/0 | ./. |
| 162 | 404142 | T | C | 0/0 | ./. | 0/0 | ./. |
| 163 | 404761 | A | G | 0/0 | ./. | 0/0 | ./. |
| 164 | 406475 | G | A | 0/0 | ./. | 0/0 | ./. |
| 165 | 406481 | T | A | 0/0 | ./. | 0/0 | ./. |
| 166 | 410940 | G | A | 0/0 | ./. | 0/0 | ./. |
| 167 | 411032 | G | A | 0/0 | ./. | 0/0 | ./. |
| 168 | 411069 | T | A | 0/0 | ./. | 0/0 | ./. |
| 169 | 411317 | GA | G | 0/0 | ./. | 0/0 | ./. |
| 170 | 413027 | C | A | 0/0 | ./. | 0/0 | ./. |
| 171 | 413058 | C | T | 0/0 | ./. | 0/0 | ./. |
| 172 | 414268 | C | G | 0/0 | ./. | 0/0 | ./. |
| 173 | 416798 | T | C | 0/0 | ./. | 0/0 | ./. |
| 174 | 417540 | G | C | 0/0 | ./. | 0/0 | ./. |
| 175 | 420742 | A | G | 0/0 | ./. | 0/0 | ./. |
| 176 | 421259 | T | C | 0/0 | ./. | 0/0 | ./. |
| 177 | 426709 | A | G | 0/0 | ./. | 0/0 | ./. |
| 178 | 427690 | G | C | 0/0 | ./. | 0/0 | ./. |
| 179 | 430705 | G | A | 0/0 | ./. | 0/0 | ./. |
| 180 | 431773 | G | A | 0/0 | ./. | 0/0 | ./. |
| 181 | 433900 | A | G | 0/0 | ./. | 0/0 | ./. |
| 182 | 442372 | T | C | 0/0 | ./. | 0/0 | ./. |
| 183 | 451131 | G | A | 0/0 | ./. | 0/0 | ./. |
| 184 | 454572 | C | A | 0/0 | ./. | 0/0 | ./. |
| 185 | 460976 | G | A | 0/0 | ./. | 0/0 | ./. |
| 186 | 461460 | C | T | 0/0 | ./. | 0/0 | ./. |
| 187 | 464177 | A | G | 0/0 | ./. | 0/0 | ./. |
| 188 | 465089 | T | C | 0/0 | ./. | 0/0 | ./. |
| 189 | 465495 | T | G | 0/0 | ./. | 0/0 | ./. |
| 190 | 468266 | C | A | 0/0 | ./. | 0/0 | ./. |
| 191 | 474980 | C | T | 0/0 | ./. | 0/0 | ./. |
| 192 | 480131 | A | T | 0/0 | ./. | 0/0 | ./. |
| 193 | 483164 | T | C | 0/0 | ./. | 0/0 | ./. |
| 194 | 484777 | A | G | 0/0 | ./. | 0/0 | ./. |
| 195 | 485948 | G | A | 0/0 | ./. | 0/0 | ./. |
| 196 | 486626 | G | C | 0/0 | ./. | 0/0 | ./. |
| 197 | 494004 | C | T | 0/0 | ./. | 0/0 | ./. |
| 198 | 494393 | T | C | 0/0 | ./. | 0/0 | ./. |
| 199 | 495953 | C | T | 0/0 | ./. | 0/0 | ./. |
| 200 | 496552 | A | G | 0/0 | ./. | 0/0 | ./. |
| 201 | 499298 | A | G | 0/0 | ./. | 0/0 | ./. |
| 202 | 499947 | T | C | 0/0 | ./. | 0/0 | ./. |
| 203 | 501352 | G | A | 0/0 | ./. | 0/0 | ./. |
| 204 | 505470 | A | G | 0/0 | ./. | 0/0 | ./. |

TABLE 4-continued

Polymorphic sites in a Nic2 deletion segment, NT1.0-Scaffold0000549. REF refers to the sequence of a reference TN90 allele. ALT refers to a sequence polymorphism found in K326, Narrow Leaf Madole, or Oriental type. "0/0" refers to homozygous for the reference TN90 allele while "./." refers to missing data (e.g., deletion).

| Nic2 Marker No. | POS | REF | ALT | BU21 | HI | LI | LA |
|---|---|---|---|---|---|---|---|
| 205 | 509926 | G | A | 0/0 | ./. | 0/0 | ./. |
| 206 | 511336 | A | G | 0/0 | ./. | 0/0 | ./. |
| 207 | 513808 | TC | T | 0/0 | ./. | 0/0 | ./. |
| 208 | 515055 | C | T | 0/0 | ./. | 0/0 | ./. |
| 209 | 516444 | A | G | 0/0 | ./. | 0/0 | ./. |
| 210 | 519420 | A | T | 0/0 | ./. | 0/0 | ./. |
| 211 | 521028 | G | C | 0/0 | ./. | 0/0 | ./. |
| 212 | 521834 | T | C | 0/0 | ./. | 0/0 | ./. |
| 213 | 524240 | A | C | 0/0 | ./. | 0/0 | ./. |
| 214 | 524256 | T | C | 0/0 | ./. | 0/0 | ./. |
| 215 | 524317 | A | G | 0/0 | ./. | 0/0 | ./. |
| 216 | 524986 | G | A | 0/0 | ./. | 0/0 | ./. |
| 217 | 526266 | A | C | 0/0 | ./. | 0/0 | ./. |
| 218 | 526905 | C | T | 0/0 | ./. | 0/0 | ./. |
| 219 | 526987 | C | A | 0/0 | ./. | 0/0 | ./. |
| 220 | 530341 | A | G | 0/0 | ./. | 0/0 | ./. |
| 221 | 531695 | A | T | 0/0 | ./. | 0/0 | ./. |
| 222 | 541587 | T | C | 0/0 | ./. | 0/0 | ./. |
| 223 | 541648 | G | A | 0/0 | ./. | 0/0 | ./. |
| 224 | 544386 | A | G | 0/0 | ./. | 0/0 | ./. |
| 225 | 545716 | T | C | 0/0 | ./. | 0/0 | ./. |
| 226 | 546047 | C | A | 0/0 | ./. | 0/0 | ./. |
| 227 | 546372 | A | G | 0/0 | ./. | 0/0 | ./. |
| 228 | 546416 | A | G | 0/0 | ./. | 0/0 | ./. |
| 229 | 546434 | T | A | 0/0 | ./. | 0/0 | ./. |
| 230 | 546775 | C | T | 0/0 | ./. | 0/0 | ./. |
| 231 | 547015 | A | G | 0/0 | ./. | 0/0 | ./. |
| 232 | 554248 | A | G | 0/0 | ./. | 0/0 | ./. |
| 233 | 554496 | C | T | 0/0 | ./. | 0/0 | ./. |
| 234 | 556239 | A | G | 0/0 | ./. | 0/0 | ./. |
| 235 | 558480 | C | T | 0/0 | ./. | 0/0 | ./. |
| 236 | 562524 | C | T | 0/0 | ./. | 0/0 | ./. |
| 237 | 563642 | A | T | 0/0 | ./. | 0/0 | ./. |
| 238 | 563802 | T | A | 0/0 | ./. | 0/0 | ./. |
| 239 | 563862 | G | T | 0/0 | ./. | 0/0 | ./. |
| 240 | 573521 | C | T | 0/0 | ./. | 0/0 | ./. |
| 241 | 573552 | T | C | 0/0 | ./. | 0/0 | ./. |
| 242 | 574370 | C | A | 0/0 | ./. | 0/0 | ./. |
| 243 | 576866 | C | T | 0/0 | ./. | 0/0 | ./. |
| 244 | 577137 | C | T | 0/0 | ./. | 0/0 | ./. |
| 245 | 582336 | T | A | 0/0 | ./. | 0/0 | ./. |
| 246 | 585822 | G | A | 0/0 | ./. | 0/0 | ./. |
| 247 | 586808 | A | G | 0/0 | ./. | 0/0 | ./. |
| 248 | 592379 | A | C | 0/0 | ./. | 0/0 | ./. |
| 249 | 594088 | T | C | 0/0 | ./. | 0/0 | ./. |
| 250 | 594122 | T | A | 0/0 | ./. | 0/0 | ./. |
| 251 | 594128 | C | A | 0/0 | ./. | 0/0 | ./. |
| 252 | 596697 | T | C | 0/0 | ./. | 0/0 | ./. |
| 253 | 599034 | G | C | 0/0 | ./. | 0/0 | ./. |
| 254 | 609636 | T | C | 0/0 | ./. | 0/0 | ./. |
| 255 | 610500 | C | T | 0/0 | ./. | 0/0 | ./. |
| 256 | 610533 | T | A | 0/0 | ./. | 0/0 | ./. |
| 257 | 610938 | A | G | 0/0 | ./. | 0/0 | ./. |
| 258 | 614216 | A | G | 0/0 | ./. | 0/0 | ./. |
| 259 | 614885 | TTA | T | 0/0 | ./. | 0/0 | ./. |
| 260 | 617065 | G | A | 0/0 | ./. | 0/0 | ./. |
| 261 | 621974 | G | A | 0/0 | ./. | 0/0 | ./. |
| 262 | 623585 | T | G | 0/0 | ./. | 0/0 | ./. |
| 263 | 645256 | C | G | 0/0 | ./. | 0/0 | ./. |
| 264 | 645263 | T | C | 0/0 | ./. | 0/0 | ./. |
| 265 | 646476 | C | T | 0/0 | ./. | 0/0 | ./. |
| 266 | 652446 | AT | A | 0/0 | ./. | 0/0 | ./. |
| 267 | 660505 | C | T | 0/0 | ./. | 0/0 | ./. |
| 268 | 667339 | G | A | 0/0 | ./. | 0/0 | ./. |
| 269 | 668081 | A | G | 0/0 | ./. | 0/0 | ./. |
| 270 | 669231 | T | G | 0/0 | ./. | 0/0 | ./. |
| 271 | 680482 | G | A | 0/0 | ./. | 0/0 | ./. |

TABLE 4-continued

Polymorphic sites in a Nic2 deletion segment, NT1.0-Scaffold0000549. REF refers to the sequence of a reference TN90 allele. ALT refers to a sequence polymorphism found in K326, Narrow Leaf Madole, or Oriental type. "0/0" refers to homozygous for the reference TN90 allele while "./." refers to missing data (e.g., deletion).

| Nic2 Marker No. | POS | REF | ALT | BU21 | HI | LI | LA |
|---|---|---|---|---|---|---|---|
| 272 | 680899 | T | C | 0/0 | ./. | 0/0 | ./. |
| 273 | 681503 | A | G | 0/0 | ./. | 0/0 | ./. |
| 274 | 681579 | TA | T | 0/0 | ./. | 0/0 | ./. |
| 275 | 685669 | G | A | 0/0 | ./. | 0/0 | ./. |
| 276 | 687781 | T | C | 0/0 | ./. | 0/0 | ./. |
| 277 | 690142 | C | T | 0/0 | ./. | 0/0 | ./. |
| 278 | 696619 | G | A | 0/0 | ./. | 0/0 | ./. |
| 279 | 696973 | C | T | 0/0 | ./. | 0/0 | ./. |
| 280 | 699014 | T | C | 0/0 | ./. | 0/0 | ./. |
| 281 | 699059 | A | G | 0/0 | ./. | 0/0 | ./. |
| 282 | 699441 | A | G | 0/0 | ./. | 0/0 | ./. |
| 283 | 699482 | A | G | 0/0 | ./. | 0/0 | ./. |
| 284 | 699507 | A | C | 0/0 | ./. | 0/0 | ./. |
| 285 | 699568 | AC | A | 0/0 | ./. | 0/0 | ./. |
| 286 | 699991 | C | T | 0/0 | ./. | 0/0 | ./. |
| 287 | 701221 | G | A | 0/0 | ./. | 0/0 | ./. |
| 288 | 701338 | C | T | 0/0 | ./. | 0/0 | ./. |
| 289 | 704968 | A | G | 0/0 | ./. | 0/0 | ./. |
| 290 | 705347 | C | T | 0/0 | ./. | 0/0 | ./. |
| 291 | 708907 | T | C | 0/0 | ./. | 0/0 | ./. |
| 292 | 710281 | C | T | 0/0 | ./. | 0/0 | ./. |
| 293 | 711996 | T | C | 0/0 | ./. | 0/0 | ./. |
| 294 | 714019 | C | A | 0/0 | ./. | 0/0 | ./. |
| 295 | 714445 | T | C | 0/0 | ./. | 0/0 | ./. |
| 296 | 714483 | T | C | 0/0 | ./. | 0/0 | ./. |
| 297 | 714491 | T | C | 0/0 | ./. | 0/0 | ./. |
| 298 | 716492 | A | G | 0/0 | ./. | 0/0 | ./. |
| 299 | 716551 | A | G | 0/0 | ./. | 0/0 | ./. |
| 300 | 721681 | G | A | 0/0 | ./. | 0/0 | ./. |
| 301 | 722271 | T | A | 0/0 | ./. | 0/0 | ./. |
| 302 | 723002 | G | C | 0/0 | ./. | 0/0 | ./. |
| 303 | 732955 | T | C | 0/0 | ./. | 0/0 | ./. |
| 304 | 734117 | T | G | 0/0 | ./. | 0/0 | ./. |
| 305 | 743601 | TA | T | 0/0 | ./. | 0/0 | ./. |
| 306 | 745383 | C | T | 0/0 | ./. | 0/0 | ./. |
| 307 | 745938 | C | T | 0/0 | ./. | 0/0 | ./. |
| 308 | 747238 | T | C | 0/0 | ./. | 0/0 | ./. |
| 309 | 750673 | A | G | 0/0 | ./. | 0/0 | ./. |
| 310 | 751683 | G | T | 0/0 | ./. | 0/0 | ./. |
| 311 | 751702 | C | T | 0/0 | ./. | 0/0 | ./. |
| 312 | 762212 | A | G | 0/0 | ./. | 0/0 | ./. |
| 313 | 762934 | C | T | 0/0 | ./. | 0/0 | ./. |
| 314 | 765864 | C | T | 0/0 | ./. | 0/0 | ./. |
| 315 | 768978 | G | A | 0/0 | ./. | 0/0 | ./. |
| 316 | 770377 | T | A | 0/0 | ./. | 0/0 | ./. |
| 317 | 773111 | G | A | 0/0 | ./. | 0/0 | ./. |
| 318 | 773112 | T | A | 0/0 | ./. | 0/0 | ./. |
| 319 | 773155 | A | T | 0/0 | ./. | 0/0 | ./. |
| 320 | 778101 | C | A | 0/0 | ./. | 0/0 | ./. |
| 321 | 778231 | T | A | 0/0 | ./. | 0/0 | ./. |
| 322 | 779756 | C | T | 0/0 | ./. | 0/0 | ./. |
| 323 | 780381 | A | G | 0/0 | ./. | 0/0 | ./. |
| 324 | 780398 | A | C | 0/0 | ./. | 0/0 | ./. |
| 325 | 782275 | A | C | 0/0 | ./. | 0/0 | ./. |
| 326 | 782502 | T | G | 0/0 | ./. | 0/0 | ./. |
| 327 | 788379 | A | G | 0/0 | ./. | 0/0 | ./. |
| 328 | 788416 | T | A | 0/0 | ./. | 0/0 | ./. |
| 329 | 789721 | C | T | 0/0 | ./. | 0/0 | ./. |
| 330 | 795120 | G | A | 0/0 | ./. | 0/0 | ./. |
| 331 | 797627 | G | A | 0/0 | ./. | 0/0 | ./. |
| 332 | 799891 | A | C | 0/0 | ./. | 0/0 | ./. |
| 333 | 800525 | A | G | 0/0 | ./. | 0/0 | ./. |
| 334 | 801525 | T | C | 0/0 | ./. | 0/0 | ./. |
| 335 | 802686 | ATGCCATGTGGTTTATATTATTGGCACG | A | 0/0 | ./. | 0/0 | ./. |

TABLE 4-continued

Polymorphic sites in a Nic2 deletion segment, NT1.0-Scaffold0000549. REF refers to the sequence of a reference TN90 allele. ALT refers to a sequence polymorphism found in K326, Narrow Leaf Madole, or Oriental type. "0/0" refers to homozygous for the reference TN90 allele while "./." refers to missing data (e.g., deletion).

| Nic2 Marker No. | POS | REF | ALT | BU21 | HI | LI | LA |
|---|---|---|---|---|---|---|---|
|  |  | TGAG TTGT CCGT GCGA GTCC AGAT ATTT ATAC TATA GC (SEQ ID NO: 72) |  |  |  |  |  |
| 336 | 802777 | A | T | 0/0 | ./. | 0/0 | ./. |
| 337 | 807008 | T | C | 0/0 | ./. | 0/0 | ./. |
| 338 | 808634 | T | G | 0/0 | ./. | 0/0 | ./. |
| 339 | 813994 | G | A | 0/0 | ./. | 0/0 | ./. |
| 340 | 817957 | A | G | 0/0 | ./. | 0/0 | ./. |

(BU21, HI BU21, LI BU21, and LA BU21) using a customized sbeadex maxi plant kit (LGC genomics, LLC, Beverly, Mass.) on the automated DNA extraction instrument, Oktopure (LGC genomics, LLC, Beverly, Mass.). Ninety (90) out of the 173 individuals were randomly chosen from this population to be genotyped at both Nic1 and Nic2 locus along with a control locus. The identified Nic1 deletion was confirmed by PCR amplification of a selected region of the identified deletion. PCR primers were designed for the Nic1 locus using Primer3 web V. 4.0.0 and are shown in Table 5. Primer sequences for Nic2 locus, and the control locus were obtained from Shoji et al. (2010), and are also provided in Table 5.

PCR was performed in a 30 μL reaction with 5 μl of ~10 ng/μl DNA, 15 μl of 2× AmpliTaq Gold® 360 MasterMix (Applied Biosystems, Foster City, Calif.), 1.2 μl of 10 μM Forward primer, 1.2 μl of 10 μM Reverse primer, and 7.6 μl of ddH$_2$O. PCR reactions proceeded with an initial denaturation at 95° C. for 5 min, followed by 35 cycles, with a temperature profile of 94° C. for 20 s, 20 s at the optimal annealing temperature (Table 5), and 72° C. for 1 minute. This was followed by a 7-minute final elongation period at 72° C., and an indefinite hold at 4° C.

TABLE 5

Table listing primer sequences and annealing temperature used for PCR

| Locus | Specific Gene | Primer | Primer Sequence (SEQ ID) | PCR Tm |
|---|---|---|---|---|
| Nic1 | g100614_Scaffold0002504 | F | CAACCTAGCCACTGGTCCAT (SEQ ID No: 3) | 62 |
|  |  | R | TCAAACCAAGAGCGAGGAGT (SEQ ID No: 4) |  |
| Nic2 | ERF 189 | F | GGGCAATGGAAATGAATCTAGC (SEQ ID No: 5) | 55 |
|  |  | R | CTTCCTTCCTTTTCACATAG (SEQ ID No: 6) |  |
| Control | ERF 199 | F | CCATTCATTTTCATCCAAACCC (SEQ ID No: 7) | 55 |
|  |  | R | CGGAGTACTTTTCATGGGATTC (SEQ ID No: 8) |  |

Example 3

Confirmation of the Identified Nic1 Locus by Genetic Segregation Analysis

To help confirm the identity of the region identified as Nic1 locus, an F$_2$ population segregating for Nic1 and Nic2 loci was developed with the aim of observing markers for nic1 and nic2 segregating with the phenotype. The F$_2$ population was developed from a cross between TN90 with LA BU21, and has a population size of 173. DNA was extracted from green leaf tissue of individual F$_2$ plants as well as the parental lines and the four known Burley lines PCR products were then visualized on eGene (Qiagen N. V., Venlo, Netherlands), with presence of a PCR product band of desirable size scored as presence of a locus and its absence noted as deletion of the locus. The primer for gene ERF199 (Table 5) served as control, and its absence indicated issues with DNA quality and if absent the sample was removed from further analyses. Alkaloid measurements of nicotine, nornicotine, anatabine and anabasin were also made on each individual plant from leaf samples collected 2 weeks after topping (Table 6), using a GC-FID method based on CORESTA Recommended Methods (CRM N0.7)

and ISO Standards (ISO TC 126N 394 E.). Alkaloid measurements served as an additional confirmation for the nic1 and nic2 genotype.

All 90 F$_2$ individuals as well as TN90, BU21, HI BU21, LI BU21 and LA BU21 showed successful amplification of the control ERF 199 primers. A deletion of Nic2 locus was observed in 19 out of the 90 F$_2$ individuals, as well as in HI BU21 and LA BU21. A deletion of Nic1 locus was seen in 21 out of the 90 F2 individuals, as well as in LI BU21 and LA BU21. Also, both Nic1 and Nic2 loci were seen to be deleted in 5 out of the 90 F$_2$ plants, along with LA BU21. Table 6 provides information on the genotype calls for 90 out of the 173 F$_2$ individual. Table 7 provides the observed and expected number of plants for each genotype given a segregation ratio of 9:3:3:1 for the two loci. Average percent total alkaloid levels for each of the four genotypes observed in the F$_2$ segregating population ((LA Burley 21×TN 90 LC) (X)) are shown in Table 8.

TABLE 6

Nic1 and Nic2 genotypes and alkaloid measurements of individual plants of the F$_2$ population segregating for nic1 and nic2 ((LA Burley 21 × TN 90 LC) (X)). The absence of Nic1 and Ni2 genotype information indicate that those plants were not genotyped. BLQ: below level of quantification.

| Plant | Nic1 Genotype (Present = 1, Absent = 0) | Nic2 Genotype (Present = 1, Absent = 0) | Percent Total Alkaloid | Percent Nicotine |
|---|---|---|---|---|
| Plant 1 | 1 | 0 | 3.0011 | 2.8628 |
| Plant 2 | 1 | 1 | 2.6729 | 2.5628 |
| Plant 3 | 0 | 1 | 2.2933 | 2.2051 |
| Plant 4 | 0 | 0 | BLQ | BLQ |
| Plant 5 | 1 | 1 | 3.1597 | 3.0139 |
| Plant 6 | 1 | 1 | 2.9731 | 2.8266 |
| Plant 7 | 0 | 0 | BLQ | BLQ |
| Plant 8 | 1 | 1 | 2.8809 | 2.763 |
| Plant 9 | 1 | 1 | 4.1221 | 3.9034 |
| Plant 10 | 1 | 1 | 3.994 | 3.8198 |
| Plant 11 | 1 | 1 | 3.7119 | 3.5467 |
| Plant 12 | 1 | 1 | 3.6687 | 3.5089 |
| Plant 13 | 1 | 1 | 4.2203 | 4.0304 |
| Plant 14 | 1 | 0 | 3.2027 | 3.0498 |
| Plant 15 | 1 | 1 | 3.7481 | 3.5971 |
| Plant 16 | 0 | 1 | BLQ | BLQ |
| Plant 17 | 1 | 1 | 4.422 | 4.1744 |
| Plant 18 | 1 | 1 | 2.8292 | 2.7127 |
| Plant 19 | 1 | 0 | 2.7538 | 2.6094 |
| Plant 20 | | | 1.9167 | 1.8179 |
| Plant 21 | 1 | 1 | 4.3081 | 4.0381 |
| Plant 22 | 1 | 1 | 3.6128 | 3.4443 |
| Plant 23 | 1 | 1 | BLQ | BLQ |
| Plant 24 | 1 | 1 | BLQ | BLQ |
| Plant 25 | 0 | 1 | 1.9377 | 1.8346 |
| Plant 26 | 1 | 1 | 2.8042 | 2.6369 |
| Plant 27 | 1 | 1 | 3.2544 | 3.1033 |
| Plant 28 | 1 | 1 | 3.4886 | 3.3306 |
| Plant 29 | 1 | 1 | 2.7115 | 2.5954 |
| Plant 30 | 1 | 1 | BLQ | BLQ |
| Plant 31 | 1 | 1 | 4.1091 | 3.9219 |
| Plant 32 | 1 | 1 | 3.2426 | 3.1062 |
| Plant 33 | 0 | 1 | 1.9005 | 1.7845 |
| Plant 34 | | | BLQ | BLQ |
| Plant 35 | 0 | 1 | 3.0363 | 2.8753 |
| Plant 36 | 1 | 1 | 3.6491 | 3.4489 |
| Plant 37 | 0 | 1 | 1.7179 | 1.6199 |
| Plant 38 | 1 | 0 | 2.8954 | 2.7684 |
| Plant 39 | 1 | 1 | 3.5936 | 3.4294 |
| Plant 40 | 0 | 1 | 2.8582 | 2.7421 |
| Plant 41 | 1 | 0 | BLQ | BLQ |
| Plant 42 | | | 4.4196 | 4.2055 |
| Plant 43 | | | BLQ | BLQ |
| Plant 44 | 0 | 1 | 1.6122 | 1.5324 |
| Plant 45 | 1 | 1 | 2.4573 | 2.3326 |
| Plant 46 | 1 | 1 | 3.4145 | 3.1655 |

TABLE 6-continued

Nic1 and Nic2 genotypes and alkaloid measurements of individual plants of the F$_2$ population segregating for nic1 and nic2 ((LA Burley 21 × TN 90 LC) (X)). The absence of Nic1 and Ni2 genotype information indicate that those plants were not genotyped. BLQ: below level of quantification.

| Plant | Nic1 Genotype (Present = 1, Absent = 0) | Nic2 Genotype (Present = 1, Absent = 0) | Percent Total Alkaloid | Percent Nicotine |
|---|---|---|---|---|
| Plant 47 | 1 | 1 | 3.5314 | 3.3588 |
| Plant 48 | 1 | 1 | 3.7216 | 3.5305 |
| Plant 49 | 1 | 0 | 3.9067 | 3.7233 |
| Plant 50 | 1 | 0 | 3.0601 | 2.9073 |
| Plant 51 | 1 | 1 | 3.8504 | 3.6463 |
| Plant 52 | 0 | 1 | BLQ | BLQ |
| Plant 53 | 1 | 1 | 4.759 | 4.47 |
| Plant 54 | | | 3.6204 | 3.4389 |
| Plant 55 | 0 | 0 | 0.5823 | 0.5489 |
| Plant 56 | 1 | 1 | 3.5092 | 3.3467 |
| Plant 57 | | | 4.107 | 3.9257 |
| Plant 58 | 0 | 1 | 2.4405 | 2.3477 |
| Plant 59 | 0 | 0 | 0.4188 | 0.3927 |
| Plant 60 | 1 | 1 | 3.8854 | 3.7403 |
| Plant 61 | 1 | 1 | 5.0457 | 4.8093 |
| Plant 62 | 0 | 1 | 2.1401 | 2.0358 |
| Plant 63 | 1 | 1 | 3.5212 | 3.3729 |
| Plant 64 | 1 | 1 | 5.1868 | 4.9157 |
| Plant 65 | | | 2.1012 | 1.9855 |
| Plant 66 | 1 | 0 | 0.3436 | 0.3282 |
| Plant 67 | | | 2.3158 | 2.2265 |
| Plant 68 | 1 | 1 | 4.5611 | 4.3195 |
| Plant 69 | 1 | 0 | 3.5517 | 3.4176 |
| Plant 70 | 1 | 1 | 3.945 | 3.7651 |
| Plant 71 | 0 | 1 | 3.8097 | 3.6456 |
| Plant 72 | 1 | 0 | 4.1787 | 3.9818 |
| Plant 73 | 1 | 0 | 5.8965 | 5.5549 |
| Plant 74 | | | 3.5723 | 3.393 |
| Plant 75 | 1 | 1 | 5.6703 | 5.3808 |
| Plant 76 | 1 | 1 | 3.1131 | 2.9747 |
| Plant 77 | 1 | 1 | 4.2168 | 4.0215 |
| Plant 78 | 0 | 1 | 2.9419 | 2.79 |
| Plant 79 | 1 | 1 | 4.2109 | 3.9834 |
| Plant 80 | | | 4.3812 | 4.1685 |
| Plant 81 | 1 | 0 | 0.7258 | 0.6868 |
| Plant 82 | 1 | 0 | 4.0284 | 3.8092 |
| Plant 83 | 0 | 1 | 2.076 | 1.9724 |
| Plant 84 | 1 | 1 | 5.1348 | 4.8334 |
| Plant 85 | 1 | 1 | 5.6781 | 5.3311 |
| Plant 86 | 1 | 1 | 4.3462 | 4.1069 |
| Plant 87 | 1 | 1 | 4.0997 | 3.8974 |
| Plant 88 | 1 | 1 | 3.47 | 3.3158 |
| Plant 89 | 0 | 1 | 2.7871 | 2.6465 |
| Plant 90 | | | 3.5846 | 3.4166 |
| Plant 91 | | | 2.3103 | 2.187 |
| Plant 92 | | | 2.8975 | 2.7746 |
| Plant 93 | | | 3.5385 | 3.3521 |
| Plant 94 | | | 5.2231 | 4.9531 |
| Plant 95 | | | 0.5855 | 0.5538 |
| Plant 96 | | | 2.6133 | 2.4813 |
| Plant 97 | | | 4.3772 | 4.1254 |
| Plant 98 | | | 5.453 | 5.0786 |
| Plant 99 | | | 3.5055 | 3.2963 |
| Plant 100 | | | 2.0902 | 1.9902 |
| Plant 101 | | | 4.5207 | 4.2845 |
| Plant 102 | | | 2.0429 | 1.943 |
| Plant 103 | | | BLQ | BLQ |
| Plant 104 | | | 3.448 | 3.3 |
| Plant 105 | | | 4.3806 | 4.1605 |
| Plant 106 | | | 4.3696 | 4.1293 |
| Plant 107 | | | 4.0754 | 3.8637 |
| Plant 108 | | | 4.1516 | 3.8525 |
| Plant 109 | | | 3.6425 | 3.4421 |
| Plant 110 | | | 4.5431 | 4.3192 |
| Plant 111 | | | 4.4435 | 4.1513 |
| Plant 112 | | | 3.9523 | 3.737 |
| Plant 113 | | | 3.4997 | 3.3269 |
| Plant 114 | | | 3.8171 | 3.638 |
| Plant 115 | | | 3.4582 | 3.3031 |
| Plant 116 | 1 | 1 | 3.5845 | 3.4243 |

TABLE 6-continued

Nic1 and Nic2 genotypes and alkaloid measurements of individual plants of the F$_2$ population segregating for nic1 and nic2 ((LA Burley 21 × TN 90 LC) (X)). The absence of Nic1 and Ni2 genotype information indicate that those plants were not genotyped. BLQ: below level of quantification.

| Plant | Nic1 Genotype (Present = 1, Absent = 0) | Nic2 Genotype (Present = 1, Absent = 0) | Percent Total Alkaloid | Percent Nicotine |
|---|---|---|---|---|
| Plant 117 | | | 3.945 | 3.7507 |
| Plant 118 | 0 | 1 | 2.5889 | 2.4632 |
| Plant 119 | 1 | 1 | 3.5472 | 3.3747 |
| Plant 120 | 0 | 1 | 2.4497 | 2.3085 |
| Plant 121 | 1 | 1 | 4.1965 | 3.9772 |
| Plant 122 | 1 | 0 | 3.8719 | 3.6731 |
| Plant 123 | 1 | 1 | 4.5964 | 4.3886 |
| Plant 124 | 1 | 1 | 3.8232 | 3.667 |
| Plant 125 | | | 4.7023 | 4.4466 |
| Plant 126 | | | 3.4026 | 3.2343 |
| Plant 127 | | | 3.2645 | 3.1016 |
| Plant 128 | | | 2.842 | 2.7461 |
| Plant 129 | | | 3.8524 | 3.6496 |
| Plant 130 | | | 4.7094 | 4.4891 |
| Plant 131 | | | 0.4548 | 0.4254 |
| Plant 132 | | | 3.3652 | 3.211 |
| Plant 133 | | | 3.2598 | 3.1137 |
| Plant 134 | | | BLQ | BLQ |
| Plant 135 | | | 3.3438 | 3.2074 |
| Plant 136 | | | 3.7641 | 3.5279 |
| Plant 137 | | | 3.6367 | 3.4453 |
| Plant 138 | 0 | 0 | 0.4207 | 0.3995 |
| Plant 139 | | | 2.2626 | 2.0909 |
| Plant 140 | | | 4.102 | 3.8806 |
| Plant 141 | | | 4.4366 | 4.2298 |
| Plant 142 | | | 4.386 | 4.1759 |
| Plant 143 | | | 5.7992 | 5.4971 |
| Plant 144 | | | BLQ | BLQ |
| Plant 145 | | | 2.8282 | 2.6992 |
| Plant 146 | | | 2.7978 | 2.6543 |
| Plant 147 | | | 3.6949 | 3.5188 |
| Plant 148 | | | 2.3355 | 2.2257 |
| Plant 149 | | | 1.7436 | 1.6735 |
| Plant 150 | | | BLQ | BLQ |
| Plant 151 | | | 1.2908 | 1.2512 |
| Plant 152 | | | 2.09 | 1.999 |
| Plant 153 | | | 3.2661 | 3.1309 |
| Plant 154 | | | BLQ | BLQ |
| Plant 155 | | | 2.9794 | 2.8095 |
| Plant 156 | | | 5.3031 | 5.0703 |
| Plant 157 | | | 3.6654 | 3.4826 |
| Plant 158 | | | 3.7191 | 3.5198 |
| Plant 159 | | | 3.5148 | 3.359 |
| Plant 160 | | | 3.0729 | 2.9446 |
| Plant 161 | | | 4.0171 | 3.8311 |
| Plant 162 | | | 2.4201 | 2.3083 |
| Plant 163 | | | 4.4837 | 4.2994 |
| Plant 164 | | | 3.5759 | 3.4229 |
| Plant 165 | | | 3.8303 | 3.6354 |
| Plant 166 | | | 4.0415 | 3.8397 |
| Plant 167 | | | 2.3684 | 2.2563 |
| Plant 168 | | | 3.5194 | 3.3464 |
| Plant 169 | | | 4.3816 | 4.1756 |
| Plant 170 | | | 3.7741 | 3.5736 |
| Plant 171 | | | 2.1715 | 2.0453 |
| Plant 172 | | | 6.5454 | 6.1323 |
| Plant 173 | | | 6.9723 | 6.6948 |

TABLE 7

The observed segregation ratio for nic1 and nic2 in the studied F$_2$ population are not significantly different from the expected segregation ratio of 9:3:3:1 at a significance threshold of 0.05 ($\chi^2$ = 0.9827, df = 3, P value = 0.1944).

| Genotype | Ratio Expected | Number of Plants Expected | Number of Plants Observed |
|---|---|---|---|
| Nic1 Nic2 | 9/16 | 50.625 | 55 |
| Nic1 nic2 | 3/16 | 16.875 | 14 |
| nic1 Nic2 | 3/16 | 16.875 | 16 |
| nic1 nic2 | 1/16 | 5.625 | 5 |

TABLE 8

Average percent total alkaloid levels for each of the four genotypes observed in the F$_2$ segregating population ((LA Burley 21 x TN 90 LC) (X)). Both the mean and standard deviation are shown. Number indicates the number of plants for each genotype for which alkaloid levels were measured. The number of plants for each genotype differs from those listed in Table 7 because plants with alkaloid levels below level of quantification (BLQ) are excluded here.

| Genotype | Number | Mean | Std Dev | Std Err Mean | Lower 95% | Upper 95% |
|---|---|---|---|---|---|---|
| Nic1 Nic2 | 49 | 3.8419 | 0.74094 | 0.10585 | 3.6291 | 4.0547 |
| Nic1 nic2 | 13 | 3.18588 | 1.43233 | 0.39726 | 2.3203 | 4.0514 |
| nic1 Nic2 | 15 | 2.43933 | 0.58525 | 0.15111 | 2.1152 | 2.7634 |
| nic1 nic2 | 3 | 0.47393 | 0.09385 | 0.05419 | 0.2408 | 0.7071 |

Example 4

Identification of Genes in Nic1 Deletion Based on the Expression Pattern of Genes in the Identified Nic1 Deletion Segment The identified Nic1 deletion segment, NT1.0-Scaffold0002504, has at least 20 annotated genes. Their expression patterns were analyzed in tobacco roots based on a Root RNASeq dataset. The Root RNASeq dataset were constructed based on RNA-sequencing and transcriptional profiling of root tissues from four varieties: BU21, HI BU21, LI BU21 and LA BU21.

Tobacco plants of these four varieties were grown in the greenhouse until a majority of the lines started budding, and then root and leaf tissue samples were harvested. Root tissue (~100 mg) from 15 plants each of the four varieties, from untopped plants and topped plants were collected. Table 9 provides details of the number of samples, time points and conditions at which sample was collected from these plants. Roots from each genotype were harvested at various time points. RNA was extracted from the roots and pooled together to form two separate pooled samples for each genotype; one before topping and one after. Specifically, tobacco roots were flash frozen in liquid nitrogen and then macerated using 2000 Geno/Grinder Spex sample prep. The macerated tissue was further used for RNA extraction on the automated Maxwell® 16 systems (Promega, Madison, Wis.), using the tissue RNA extraction kit (Promega, Madison, Wis.). The isolated RNA was quantified using a Nanodrop1000 to confirm that all samples met the minimum yield required for 2×100 bp paired end sequencing using HiSeq2000.

After sequencing, the raw RNASeq reads were trimmed and further filtered. The filtered RNASeq reads were then mapped to ALCS's proprietary tobacco genome using the transcriptome mapping application in CLC genomics workbench v.7.1 (Qiagen, N.V., Velno, The Netherlands). The raw expression of a gene is measured as the number of mapped reads for each of the 204,695 annotated genes within the tobacco genome. The gene expression value for each gene was then normalized using the reads per kilobase of transcript per million mapped reads (RPKM) values to obtain relative levels of gene expression.

Among the 20 genes annotated in the identified Nic1 deletion segment, NT1.0-Scaffold0002504, 18 genes show no expression in any of the varieties at any condition. Only 2 genes were expressed in the root (Table 10). They are g100614_Scaffold0002504 and g100631_Scaffold0002504 (having genomic sequences of SEQ ID NOs: 28 and 13, cDNA sequences of SEQ ID NOs: 48 and 33, protein sequences of SEQ ID NOs: 68 and 53, respectively). Both expressed genes are annotated as "late blight resistance protein homolog". Similar expression patterns were also observed for genes at Nic2 locus (Table 11).

TABLE 9

Tissue sampling designs for RNAseq-based transcriptional profiling of tobacco roots.

| | | Number of plants sampled | | | | |
|---|---|---|---|---|---|---|
| | | Time point | | | | |
| Genotype | Condition | 30 mins | 2 hrs | 6 hrs | 24 hrs | 72 hrs |
| Burley 21 | Before Topping | 3 | 3 | 3 | 3 | 3 |
| | After Topping | 3 | 3 | 3 | 3 | 3 |
| HI Burley 21 | Before Topping | 3 | 3 | 3 | 3 | 3 |
| | After Topping | 3 | 3 | 3 | 3 | 3 |
| LI Burley 21 | Before Topping | 3 | 3 | 3 | 3 | 3 |
| | After Topping | 3 | 3 | 3 | 3 | 3 |
| LA Burley 21 | Before Topping | 3 | 3 | 3 | 3 | 3 |
| | After Topping | 3 | 3 | 3 | 3 | 3 |

Example 5

Identification of Genes Regulated by Nic1 and Nic2

The Root RNASeq dataset from Example 4 also allowed the identification of genes, the expression of which is regulated by Nic1 or Nic2. Pairwise comparisons of gene expression in four varieties: BU21, HI BU21, LI BU21 and LA BU21 were performed. FIG. 1 shows the number of genes identified as up or down regulated between each possible pairwise combination of varieties at false discovery rate (FDR) corrected P value of 0.05.

Figure 2:
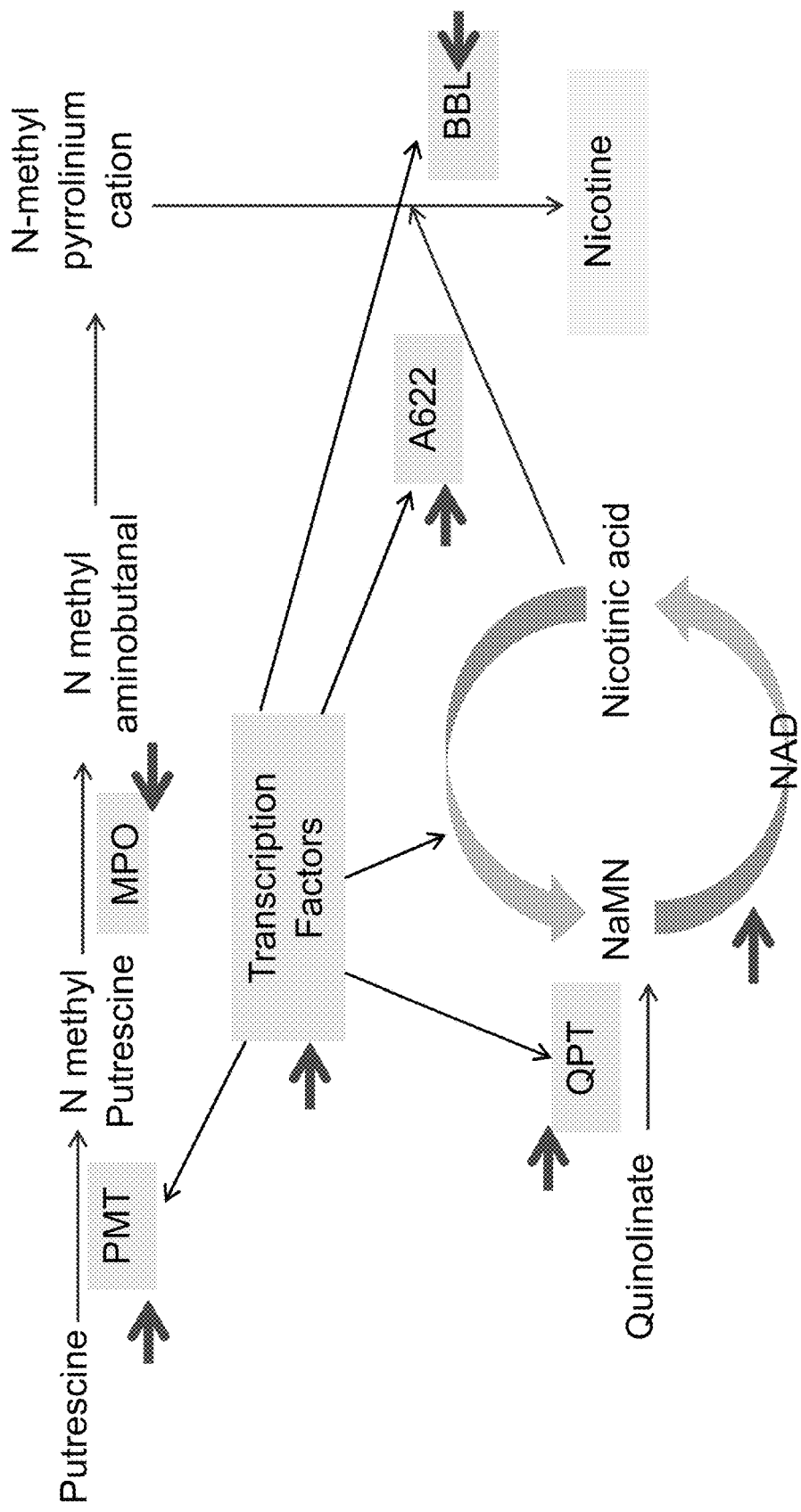
FIG. 2 shows that Nic1 regulates genes involved in nicotine biosynthesis. Red arrows indicate genes whose expression is upregulated in the presence of Nic1, especially within comparisons (i) BU21 vs LA BU21, and (ii) HI BU21 vs LA BU21.

The comparisons of BU21 vs LA BU21 and that of HI BU21 vs LA BU21 are the most informative, with identification of all genes in the Nicotine biosynthesis pathway post formation of Putrescine. The effects of Nic1 locus (present in BU21 and HI BU21, but absent in LA BU21) were also confirmed. FIG. 2 indicate some of the genes upregulated in presence of Nic1.

Example 6

Development of Molecular Markers at or Near Nic1 and Nic2 Deletion Segments

The identified Nic1 deletion segment, NT1.0-Scaffold0002504, has a length of at least 544,860 bps. Within this segment, at least 207 variant sites were detected between a reference TN90 genome sequence and BU21 lines representing a pattern of deletion (Table 3)

The identified Nic2 deletion segment within scaffoldNT1.0-Scaffold0000549 (total length of NT1.0-Scaffold0000549=1,142,469 bps), has a length of at least 820,000 bps. Within this segment, at least 340 polymorphic sites were detected between a reference TN90 genome sequence and Burley 21 lines representing a pattern of deletion (Table 4)

Example 7

Breeding of Tobacco Varieties Containing Low Nicotine

The identified nic1 deletion segment, genes within, and molecular markers associated therewith are used to breed and produce low nicotine tobacco hybrids, varieties, and lines which comprise a nic1 deletion or partial deletion. These genes and markers are also used to screen for additional nic1 and nic2 alleles from various *Nicotiana* germplasm, for example, different *Nicotiana* species or *Nicotiana tabacum* lines. A collection of forty-three *Nicotiana* species, forty-nine *Nicotiana rustica* lines, and approximately six hundred *Nicotiana tabacum* lines that can be screened is provided in Table 8 of U.S. Pat. No. 7,700,834.

Germplasm identified as having novel nic1 or nic2 alleles is used as source material for breeding with cultivated tobaccos. Interspecific or intraspecific hybridization methods combined with standard breeding methods, such as backcrossing or the pedigree method, may be used to transfer a desirable nic1 or nic2 mutant allele from the donor source to cultivated tobaccos. For example, a low-nicotine variety comprising a nic1, nic2, or both mutant alleles (e.g., a donor parent such as LA Burley 21) is crossed to an elite high-nicotine variety having a desirable genetic background and agronomically elite traits. $F_1$ progeny plants from this cross is optionally assayed for one or more molecular markers exemplified in Tables 9 and 10. An $F_1$ progeny plant is then backcrossed with the parent elite high-nicotine variety (recurrent parent). Plants from the BC1 generation are genotyped using molecular markers exemplified in Tables 9 and 10 to select for tobacco plants with smaller nic1 or nic2 deletion segments. After multiple rounds of backcrossing (e.g., 5-7 generations), an new elite tobacco variety is obtained comprising both a low-nicotine trait and other desirable traits from the recurrent parent elite line. This new elite tobacco variety is also free to any genetic drag associated with the low-nicotine trait due to genetic recombination events around Nic1 and Nic2 loci. These recombination events unlink nic1 and nic2 mutations from any associated detrimental mutations and thus reduce or avoid genetic drag. Using the above breeding and marker-assisted selection strategy, one can also achieve the pyramiding or stacking of a low-nicotine trait with other transgenes or natural alleles that reduce nicotine or nornicotine levels.

Low-nicotine tobacco hybrids, varieties, or lines can be made as a Burley type, a dark type, a flue-cured type, a Maryland type or an Oriental type tobacco, or can be essentially derived from BU 64, CC 101, CC 200, CC 27, CC 301, CC 400, CC 500, CC 600, CC 700, CC 800, CC 900, Coker 176, Coker 319, Coker 371 Gold, Coker 48, CU 263, DF911, *Galpao* tobacco, GL 26H, GL 350, GL 600, GL 737, GL 939, GL 973, HB 04P, K 149, K 326, K 346, K 358, K394, K 399, K 730, KDH 959, KT 200, KT204LC, KY 10, KY 14, KY 160, KY 17, KY 171, KY 907, KY907LC, KTY14×L8 LC, Little Crittenden, McNair 373, McNair 944, msKY 14×L8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVHSO, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, or VA359, Maryland 609, HB3307PLC, HB4488PLC, KT206LC, KT209LC, KT210LC, KT212LC, R610LC, PVH2310, NC196, KTD14LC, KTD6LC, KTD8LC, PD7302LC, PD7305LC, PD7309LC, PD7318LC, PD7319LC, PD7312LC, ShireyLC, or any commercial tobacco variety according to standard tobacco breeding techniques known in the art.

TABLE 10

Genes annotated in a Nic1 deletion scaffold, NT1.0-Scaffold0002504 (SEQ ID No. 1). "Start" and "End" denote the starting and ending nucleotide positions of the annotated genes on scaffold NT1.0-Scaffold0002504. Only two bolded genes (g100631_Scaffold0002504 and g100614_Scaffold0002504) were observed to express in the root of BU21 and HI BU21 both before and after topping. No expression of these two genes were detected in LI BU21 or LA BU21 roots. All other listed genes show no root expression in BU21, HI BU21, LI BU21, or LA BU21 based on the Root RNASeq dataset. The asterisk (*) indicates that SEQ ID Nos. 83 and 84 correspond to refined cDNA and amino acid sequences of SEQ ID NO. 80, respectively.

| Gene | Blast Hit Description | Start | End | Genomic sequence (SEQ ID) | Refined genomic sequence (SEQ ID) | cDNA sequence (SEQ ID) | Amino acid sequence (SEQ ID) |
|---|---|---|---|---|---|---|---|
| g100624_Scaffold0002504 | gi\|113205363\|gb\|AAT66771.2\|Putative polyprotein, identical [Solanum demissum] | 23574 | 44762 | 9 | | 29 | 49 |
| g100616_Scaffold0002504 | gi\|113205363\|gb\|AAT66771.2\|Putative polyprotein, identical [Solanum demissum] | 49007 | 62258 | 10 | | 30 | 50 |
| g100619_Scaffold0002504 | gi\|460410342\|ref\|XP_004250589.1\|PREDICTED: uncharacterized protein LOC101263780 [Solanum lycopersicum] | 63561 | 67079 | 11 | | 31 | 51 |
| g100629_Scaffold0002504 | gi\|113205363\|gb\|AAT66771.2\|Putative polyprotein, identical [Solanum demissum] | 72790 | 84448 | 12 | | 32 | 52 |
| g100631_Scaffold0002504 | **gi\|460370553\|ref\|XP_004231117.1\| PREDICTED: putative late blight resistance protein homolog R1A-10-like [ [*Solanum lycopersicum*]] | 124722 | 127361 | 13 | | 33 | 53** |
| g100627_Scaffold0002504 | gi\|113205316\|gb\|ABI34339.1\|Polyprotein, 3'-partial, putative [Solanum demissum] | 130345 | 131552 | 14 | | 34 | 54 |
| g100630_Scaffold0002504 | gi\|113205316\|gb\|ABI34339.1\|Polyprotein, 3'-partial, putative [Solanum demissum] | 146435 | 147770 | 15 | | 35 | 55 |
| g100633_Scaffold0002504 | gi\|113205316\|gb\|ABI34339.1\|Polyprotein, 3'-partial, putative [Solanum demissum] | 174793 | 179215 | 16 | | 36 | 56 |
| g100620_Scaffold0002504 | NA | 186534 | 189120 | 17 | | 37 | 57 |
| g100625_Scaffold0002504 | gi\|460395064\|ref\|XP_004243109.1\|PREDICTED: uncharacterized protein LOC101263429 [Solanum lycopersicum] | 247160 | 250636 | 18 | | 38 | 58 |
| g100615_Scaffold0002504 | gi\|113205363\|gb\|AAT66771.2\|Putative polyprotein, identical [Solanum demissum] | 263965 | 268932 | 19 | | 39 | 59 |
| g100618_Scaffold0002504 | gi\|460410504\|ref\|XP_004250667.1\|PREDICTED: uncharacterized protein LOC101267192 [Solanum lycopersicum] | 282902 | 284495 | 20 | | 40 | 60 |
| g100622_Scaffold0002504 | NA | 305097 | 306605 | 21 | 75 | 41 | 61 |
| g100617_Scaffold0002504 | gi\|113205345\|gb\|AAT38783.2\|hypothetical protein SDM1_46t00006 [Solanum demissum] | 351391 | 354310 | 22 | 76 | 42 | 62 |
| g100621_Scaffold0002504 | gi\|113205363\|gb\|AAT66771.2\|Putative polyprotein, identical [Solanum demissum] | 385927 | 388324 | 23 | 77 | 43 | 63 |
| g100632_Scaffold0002504 | NA | 421150 | 422045 | 24 | 78 | 44 | 64 |
| g100628_Scaffold0002504 | NA | 427647 | 432434 | 25 | 79 | 45 | 65 |
| g100623_Scaffold0002504 | gi\|89179421\|gb\|ABD63156.1\|Retrotransposon gag protein [Asparagus officinalis] | 471868 | 472786 | 26 | 80* | 46 | 66 |
| g100626_Scaffold0002504 | gi\|147845547\|emb\|CAN78493.1\|hypothetical protein VITISV_037041 [Vitis vinifera] | 477222 | 483825 | 27 | 81 | 47 | 67 |
| g100614_Scaffold0002504 | **gi\|460406698\|ref\|XP_004248798.1\| PREDICTED: putative late blight resistance protein homolog R1B-14-like [ [*Solanum lycopersicum*]] | 530011 | 535390 | 28 | 82 | 48 | 68** |

TABLE 11

Genes annotated in a Nic2 deletion scaffold, NT1.0-Scaffold0000549 (SEQ ID No. 2). "Start" and "End" denote the starting and ending nucleotide positions of the annotated genes on scaffold NT1.0-Scaffold0002504. Only three bolded genes (g38885_Scaffold0000549, g38878_Scaffold0000549 and g38864_Scaffold0000549) were observed to express in the root of BU21 and LI BU21 both before and after topping. No expression of these three genes were detected in HI BU21 or LA BU21 roots. All other listed genes show no root expression in BU21, HI BU21, LI BU21, or LA BU21 based on the Root RNASeq dataset.

| Gene | Blast Hit Description | Start | End |
|---|---|---|---|
| g38875_Scaffold0000549 | gi\|47824950\|gb\|AAT38724.1\|Putative retrotransposon protein, identical [*Solanum demissum*] | 1064 | 2604 |
| g38854_Scaffold0000549 | gi\|460414233\|ref\|XP_004252477.1\|PREDICTED: uncharacterized protein LOC101245629 [*Solanum lycopersicum*] | 12488 | 12827 |
| g38847_Scaffold0000549 | gi\|460407027\|ref\|XP_004248959.1\|PREDICTED: uncharacterized protein LOC101266468 [*Solanum lycopersicum*] | 40706 | 42338 |
| g38857_Scaffold0000549 | gi\|460410342\|ref\|XP_004250589.1\|PREDICTED: uncharacterized protein LOC101263780 [*Solanum lycopersicum*] | 63740 | 66314 |
| g38861_Scaffold0000549 | gi\|460395064\|ref\|XP_004243109.1\|PREDICTED: uncharacterized protein LOC101263429 [*Solanum lycopersicum*] | 69289 | 71053 |
| g38873_Scaffold0000549 | gi\|460407027\|ref\|XP_004248959.1\|PREDICTED: uncharacterized protein LOC101266468 [*Solanum lycopersicum*] | 71359 | 78187 |
| g38871_Scaffold0000549 | gi\|460415745\|ref\|XP_004253217.1\|PREDICTED: uncharacterized protein LOC101263890 [*Solanum lycopersicum*] | 99417 | 112568 |
| g38850_Scaffold0000549 | NA | 136925 | 137758 |
| g38855_Scaffold0000549 | NA | 141858 | 144628 |
| g38872_Scaffold0000549 | NA | 147982 | 150752 |
| g38849_Scaffold0000549 | gi\|147865536\|emb\|CAN81563.1\|hypothetical protein VITISV_019697 [*Vitis vinifera*] | 151800 | 153027 |
| g38866_Scaffold0000549 | gi\|460407027\|ref\|XP_004248959.1\|PREDICTED: uncharacterized protein LOC101266468 [*Solanum lycopersicum*] | 159812 | 161152 |
| g38853_Scaffold0000549 | gi\|460407027\|ref\|XP_004248959.1\|PREDICTED: uncharacterized protein LOC101266468 [*Solanum lycopersicum*] | 165374 | 166727 |
| g38868_Scaffold0000549 | NA | 205238 | 206813 |
| g38884_Scaffold0000549 | gi\|460406842\|ref\|XP_004248867.1\|PREDICTED: putative ribonuclease H protein At1g65750-like [*Solanum lycopersicum*] | 223785 | 228636 |
| g38876_Scaffold0000549 | NA | 246679 | 246970 |
| g38856_Scaffold0000549 | NA | 263028 | 264922 |
| g38859_Scaffold0000549 | NA | 267551 | 269920 |
| g38848_Scaffold0000549 | gi\|460410377\|ref\|XP_004250606.1\|PREDICTED: uncharacterized protein LOC101247390 [*Solanum lycopersicum*] | 274617 | 278325 |
| g38885_Scaffold0000549 | **gi\|296278604\|gb\|ADH04266.1\|ERF1 [*Nicotiana benthamiana*] | 279007 | 279583** |
| g38862_Scaffold0000549 | NA | 281949 | 283475 |
| g38877_Scaffold0000549 | gi\|147773804\|emb\|CAN60970.1\|hypothetical protein VITISV_026408 [*Vitis vinifera*] | 313840 | 316312 |
| g38869_Scaffold0000549 | gi\|147775355\|emb\|CAN65719.1\|hypothetical protein VITISV_020846 [*Vitis vinifera*] | 320254 | 322003 |
| g38881_Scaffold0000549 | gi\|460410342\|ref\|XP_004250589.1\|PREDICTED: uncharacterized protein LOC101263780 [*Solanum lycopersicum*] | 336602 | 338552 |
| g38852_Scaffold0000549 | gi\|113205363\|gb\|AAT66771.2\|Putative polyprotein, identical [*Solanum demissum*] | 352315 | 358329 |
| g38886_Scaffold0000549 | gi\|460387720\|ref\|XP_004239522.1\|PREDICTED: uncharacterized protein LOC101244956 [*Solanum lycopersicum*] | 359255 | 372066 |
| g38878_Scaffold0000549 | **gi\|296278604\|gb\|ADH04266.1\|ERF1 [*Nicotiana benthamiana*] | 372621 | 375461** |
| g38860_Scaffold0000549 | gi\|460366233\|ref\|XP_004228993.1\|PREDICTED: uncharacterized protein LOC101255727 [*Solanum lycopersicum*] | 386045 | 387443 |
| g38864_Scaffold0000549 | **gi\|296278604\|gb\|ADH04266.1\|ERF1 [*Nicotiana benthamiana*] | 416812 | 419577** |
| g38863_Scaffold0000549 | NA | 449315 | 449560 |
| g38865_Scaffold0000549 | NA | 449684 | 449943 |
| g38879_Scaffold0000549 | gi\|470132088\|ref\|XP_004301918.1\|PREDICTED: uncharacterized protein LOC101298139 [*Fragaria vesca* subsp. *vesca*] | 456673 | 458830 |
| g38867_Scaffold0000549 | gi\|460395064\|ref\|XP_004243109.1\|PREDICTED: uncharacterized protein LOC101263429 [*Solanum lycopersicum*] | 550298 | 551726 |
| g38883_Scaffold0000549 | NA | 666517 | 668921 |
| g38846_Scaffold0000549 | NA | 679387 | 681160 |
| g38843_Scaffold0000549 | gi\|113205316\|gb\|ABI34339.1\|Polyprotein, 3'-partial, putative [*Solanum demissum*] | 696597 | 697503 |
| g38880_Scaffold0000549 | gi\|4406792\|gb\|AAD20101.1\|putative retroelement pol polyprotein [*Arabidopsis thaliana*] | 748082 | 752804 |
| g38870_Scaffold0000549 | gi\|156603850\|ref\|XP_001618917.1\|hypothetical protein NEMVEDRAFT_v1g68789 [*Nematostella vectensis*]gi\|156200895\|gb\|EDO26817.1\|predicted protein [*Nematostella vectensis*] | 766567 | 768613 |
| g38874_Scaffold0000549 | gi\|460415871\|ref\|XP_004253277.1\|PREDICTED: uncharacterized protein LOC101244169 [*Solanum lycopersicum*] | 769094 | 773060 |
| g38844_Scaffold0000549 | gi\|460415745\|ref\|XP_004253217.1\|PREDICTED: uncharacterized protein LOC101263890 [*Solanum lycopersicum*] | 781866 | 785313 |

Example 8

Development of Tobacco Varieties with Desirable Nicotine Levels Via a Transgenic Approach Both overexpression and suppression approaches are taken to investigate the function of Nic1 genes. Two sets of transgenic plants are generated, one using the full length coding sequence and the other using an RNAi sequence. For expression of the full length coding sequence or the RNAi sequence, an expression vector can be constructed to have a CsVMV promoter and a NOS terminator, as well as a cassette having a Kanamycin selection marker (NPT II) under direction of an actin2 promoter and having a NOS terminator. Exemplary transformation cassette sequences of RNAi constructs targeting genes in Nic deletion segment can be found in SEQ ID Nos: 69 and 70. One of ordinary skill in the art understands that other target sequences can be used in constructing RNAi constructs or other transgenic approach for gene silencing (e.g., artificial microRNA, trans-acting siRNA, etc.).

Nucleic acid constructs carrying transgenes of interest are introduced into tobacco leaf disc using DNA bombardment or a biolistic approach. See, for example, Sanford et al., 1993, Methods Enzymol., 217:483-510; and Okuzaki and Tabei, 2012, Plant Biotechnology, 29:307-310. Briefly, the plasmid DNA containing the transformation cassette is coated on 1 μm gold particles (DNA/gold) as follows. The 1 μm gold particles are baked at 180° C. for 12 hours, and a stock solution (40 mg/ml) is prepared. To make a mixture for 10 shots, 100 μl of the stock solution is mixed with 40 μl of expression vector DNA (1 μg/μl), 100 μl of 2.5 M $CaCl_2$, and 40 μl of 0.1 M spermidine in a 1.5-ml tube. The mixture is centrifuged for 30 s at 13,000×g, and the pellet is washed with 500 μl 100% ethanol. The DNA/gold mixture is suspended in 100 μl of water, and 10 μl is applied onto a macrocarrier, dried, and then bombarded. Two shots are bombarded per plate using a 1,100 psi rupture disc under partial vacuum (711 mmHg) in a PDS-1000/He system (Bio-Rad Laboratories, Hercules, Calif., USA). Narrow Leaf Madole (NLM) and Tennessee 90 (TN90) tobacco leaf discs are used for transformation with the RNAi constructs, and with the full length gene constructs. Whole tobacco leaf (about 45×30 mm in length) is placed on the MS medium overnight, and the leaf disc is bombarded with the construct on the second day. Leaves are then cut into small pieces (about 5×5 mm) and replaced on the TOM medium (MS medium with 20 g sucrose/L; 1 mg/L IAA and 2.5 mg/L BAP) to grow at 27° C. for 3-5 days, then transferred to TOM medium to grow, which contains 300 mg/l Kanamycin (TOM-Kan). Tissues are transferred to new TOM-Kan plates every 2-3 weeks for 4-6 weeks (27° C., 16 h light). Kanamycin-resistant primary shoots are regenerated at 4-6 weeks after bombardment. Shoots are transferred to MS-Kanamycin plates to grow root. The leaves and/or roots from T1 plants (and subsequent generations) are then evaluated to determine the amount of one or more alkaloids and/or one or more TSNAs.

Example 9

Development of Novel Nic1 Mutations Via Random Mutagenesis

Random mutagenesis of tobacco plants are performed using Ethyl methanesulfonate (EMS) mutagenesis or fast neutron bombardment. EMS mutagenesis consists of chemically inducing random point mutations over the length of the genome. Fast neutron mutagenesis consists of exposing seeds to neutron bombardment which causes large deletions through double stranded DNA breakage.

For EMS mutagenesis, one gram (approximately 10,000 seeds) of Tennessee 90 tobacco (TN90) seeds are washed in 0.1% Tween for fifteen minutes and then soaked in 30 ml of ddH2O for two hours. One hundred fifty (150) μl of 0.5% EMS (Sigma, Catalogue No. M-0880) is then mixed into the seed/ddH2O solution and incubated for 8-12 hours (rotating at 30 rpm) under a hood at room temperature (RT; approximately 20° C.). The liquid then is removed from the seeds and mixed into 1 M NaOH overnight for decontamination and disposal. The seeds are then washed twice with 100 ml ddH2O for 2-4 hours. The washed seeds were then suspended in 0.1% agar solution.

The EMS-treated seeds in the agar solution are evenly spread onto water-soaked Carolina's Choice Tobacco Mix (Carolina Soil Company, Kinston, N.C.) in flats at ~2000 seeds/flat. The flats are then covered with plastic wrap and placed in a growth chamber. Once the seedlings emerge from the soil, the plastic wrap is punctured to allow humidity to decline gradually. The plastic wrap is completely removed after two weeks. Flats are moved to a greenhouse and fertilized with NPK fertilizer. The seedlings re plugged into a float tray and grown until transplanting size. The plants are subsequently transplanted into a field. During growth, the plants self-pollinate to form M1 seeds. At the mature stage, five capsules are harvested from each plant and individual designations are given to the set of seeds from each plant. This forms the M1 population. A composite of M1 seed from each M0 plant are grown, and leaves from M1 plants are collected for DNA extraction. Target genes are amplified and sequenced for mutation identification.

Example 10

Development of Novel Nic1 Mutations Via Targeted Mutagenesis

Tobacco lines with low nicotine while maintaining high leaf quality are produced by introducing mutations into Nic1 locus via precise genome engineering technologies, for example, Transcription activator-like effector nucleases (TALENs), meganuclease, zinc finger nuclease, and CRISPR. Genome modifications are made in commercial tobacco varieties such as TN90, K326 and Narrow Leaf Madole.

For example, specific target sequences from Nic1 genes can serve as TALEN target binding regions. The TALEN sites are specific for the single gene or a DNA segment from Nic1 locus. TALEN regions 1 and 2 would be used to disrupt a critical region of Nic1 and partial fuse together to create long stretch deletion but smaller than entire Nic1 deletion region. The plants created will be expected to have low nicotine contents but high leaf quality.

Based on target DNA sequences, sequences for transcription activator like (TAL) effector proteins are synthesized and cloned into plant expression vectors to serve as entry vectors. Depending on the purpose, different protocols are used to generate mutagenic tobacco lines: 1) one or more entry vectors (pALCS1 containing the target TALs) are directly transformed into tobacco protoplasts to generate random sequence deletion or insertion mutagenic tobacco lines; 2) a donor sequence (e.g., a reporter gene, e.g., the GUS gene) flanked on the left and right side with sequences that are homologous with the target insertion sequence is co-transformed into tobacco protoplasts with one or more entry vectors (pALCS1 containing the target TALs) to generated mutagenic tobacco lines containing a reporter gene; and 3) a donor sequence containing target TALs that have a point mutation is co-transformed into tobacco protoplasts with one or more entry vectors (pALCS1 containing the target TALs) to generated mutagenic tobacco lines having a point mutation; 4) a donor sequence containing a tissue specific promoter sequence to generate mutant tobacco lines that express the endogenous gene in a tissue specific manner; and 5) a donor sequence containing a combination of the aforementioned donor sequences with a reporter gene construct to facilitate mutant tobacco screening.

Tobacco protoplasts are isolated from TN90 tobacco leaves growing in Magenta boxes in a growth chamber.

Well-expanded leaves (5 cm) from 3-4-week-old plants are cut into 0.5 to 1-mm leaf strips from the middle part of a leaf Leaf strips are transferred into the prepared enzyme solution (1% cellulase R10, 0.25% macerozyme R10, 0.4 M mannitol, 20 mM KCl, 20 mM MES (pH 5.7), 10 mM CaCl2, 0.1% BSA) by dipping both sides of the strips. Leaf strips are vacuum infiltrated for 30 min in the dark using a desiccator with continuing digestion in the dark for 4 hour to overnight at room temperature without shaking Protoplasts are filtered in 100 µm nylon filter and purified with 3 ml Lymphoprep. Protoplasts are centrifuged and washed with W5n solution (154 mM NaCl, 125 mM $CaCl_2$, 5 mM KCl, 2 mM MES, 991 mg/l glucose pH 5.7) and suspended in W5n solution at the concentration of 5×105/ml. Protoplasts are kept on ice for 30 min to settle at the bottom of the tube by gravity. W5n solution was moved and protoplasts were re-suspended in P2 solution at room temperature. 50 µl DNA (10-20 µg of plasmid), 500 µl protoplasts (2×105 protoplasts) and 550 µl of PEG solution (40%, v/v 10 ml 4 g PEG4000, 0.2 M mannitol, 0.1 M CaCl2) are mixed gently in a 15-ml microfuge tube, and the mixture incubated at room temperature for 5 min.

Protoplasts are pelleted and re-suspended with 1 ml 2×8EN1 (8EN1: MS salt without $NH_4NO_3$, MS vitamin, 0.2% myo-Inositol, 4 mM MES, 1 mg/l NAA, 1 mg/l IAA, 0.5 M mannitol, 0.5 mg/l BAP, 1.5% sucrose). Transformed protoplasts are jellified with equal amount of low-meting agarose (LMA), and 0.2 ml of protoplast-LAM is dropped to form a bead. 10 ml 8EN1 is added to the bead, and in 7 days, 5 ml 8EN1 is taken out and 5 ml 8EN2 (8EN1 with 0.25 M mannitol) is added; after another 7 days (14 day), 10 ml 8EN2 is taken out and 10 ml 8EN2 is added; in another 7 days (21 day), 5 ml 8EN2 is taken out and 5 ml 8EN3 (8EN1 with 3% sucrose and without mannitol) is added; after another 7 days (28 day), 10 ml 8EN3 is taken out and 10 ml 8EN3 is added. Protoplasts are kept for two weeks until micro-callus growth. Callus is transferred to NCM solid media until it reaches about 5 mm (usually about two weeks). Callus was transferred to TOM-Kan solid media to grow shoots, and transformed tobacco plants were regenerated using the methods described herein.

Example 11

Further Genetic Confirmation of the Identified Nic1 Lesion

A genetic segregation analysis was conducted in an $F_2$ population of 522 plants from a cross between TN90 with LA BU21 (Table 12). This $F_2$ population ((LA Burley 21×TN 90 LC) (X)) was subject to PCR-based genotyping of the Nic1 and Nic2 loci as described in Example 3. The percent total alkaloid and percent nicotine levels of each plant were also measured as in Example 3. Briefly, tobacco samples were collected at an intermediate growth stage (layby stage) for genotyping. The plants were topped at an elongated bud stage. Samples for chemistry analysis were taken two weeks after topping of the plants.

Figure 3:
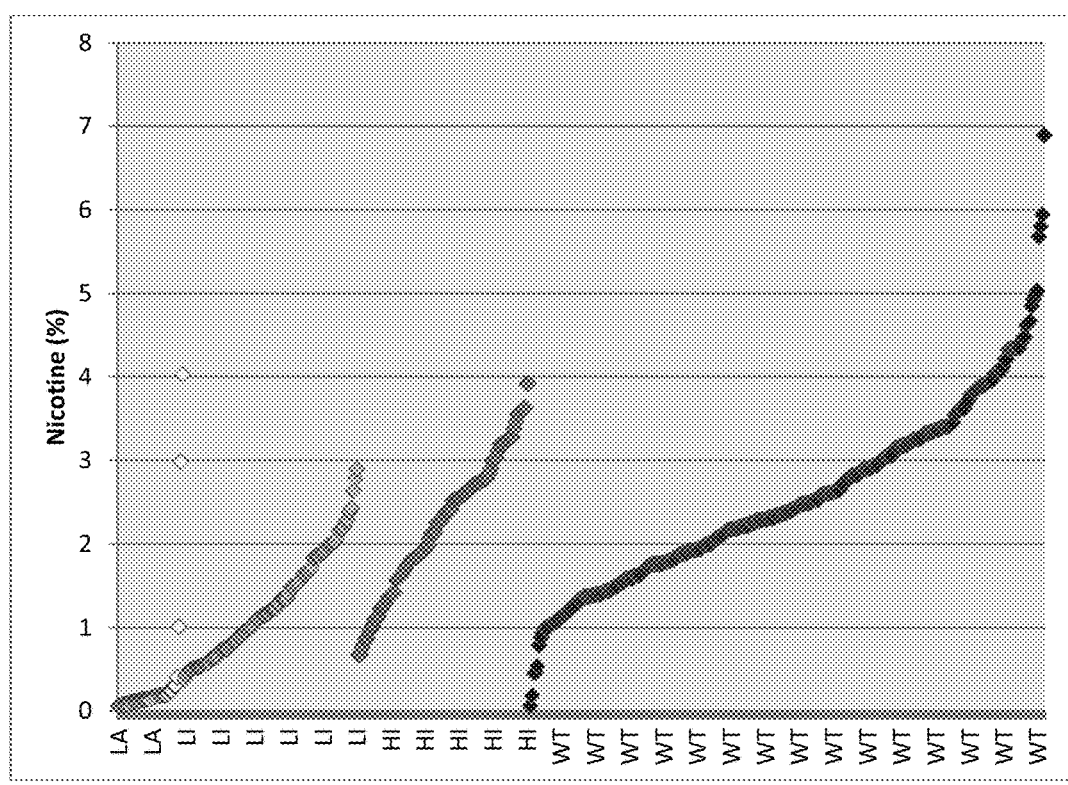
FIG. 3 shows genotypic and chemistry data of an $F_2$ population by plotting the chemistry (y axis) of each plant by it genotype (x axis).
Figure 4:
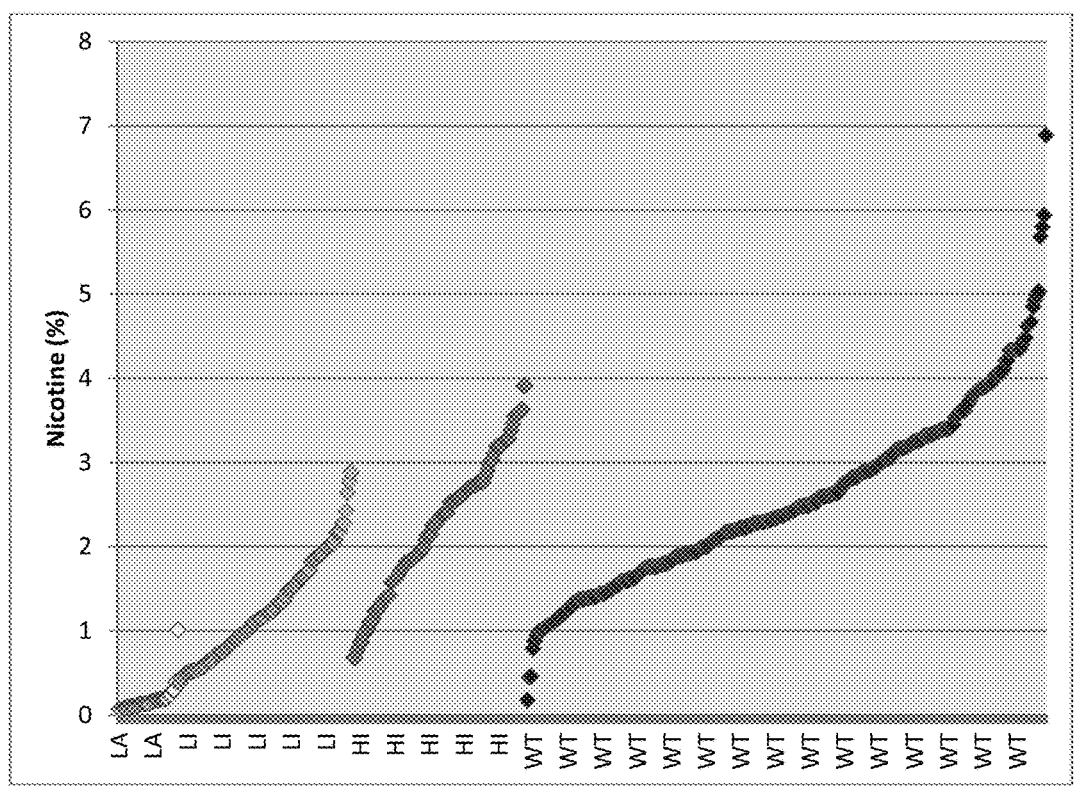
FIG. 4 is identical to FIG. 3 except excluding 8 outliers likely due to sampling errors.

The genotypic data again confirm a segregation ratio of 9:3:3:1 for the Nic1 and Nic2 loci in the $F_2$ population. Average percent total alkaloid and average percent nicotine levels in each of the four genotypes are also consistent with the segregation data and the earlier observation that nic1 has a stronger effect than nic2 over the total alkaloid and nicotine levels (Tables 13 and 14). The genotype and chemistry data of this $F_2$ population are further shown in FIGS. 3 and 4 by plotting the chemistry (y axis) of each plant by it genotype (x axis). FIG. 4 differs from FIG. 3 in its exclusion of 8 plants that were likely switched due to sampling or processing errors.

Figure 5:
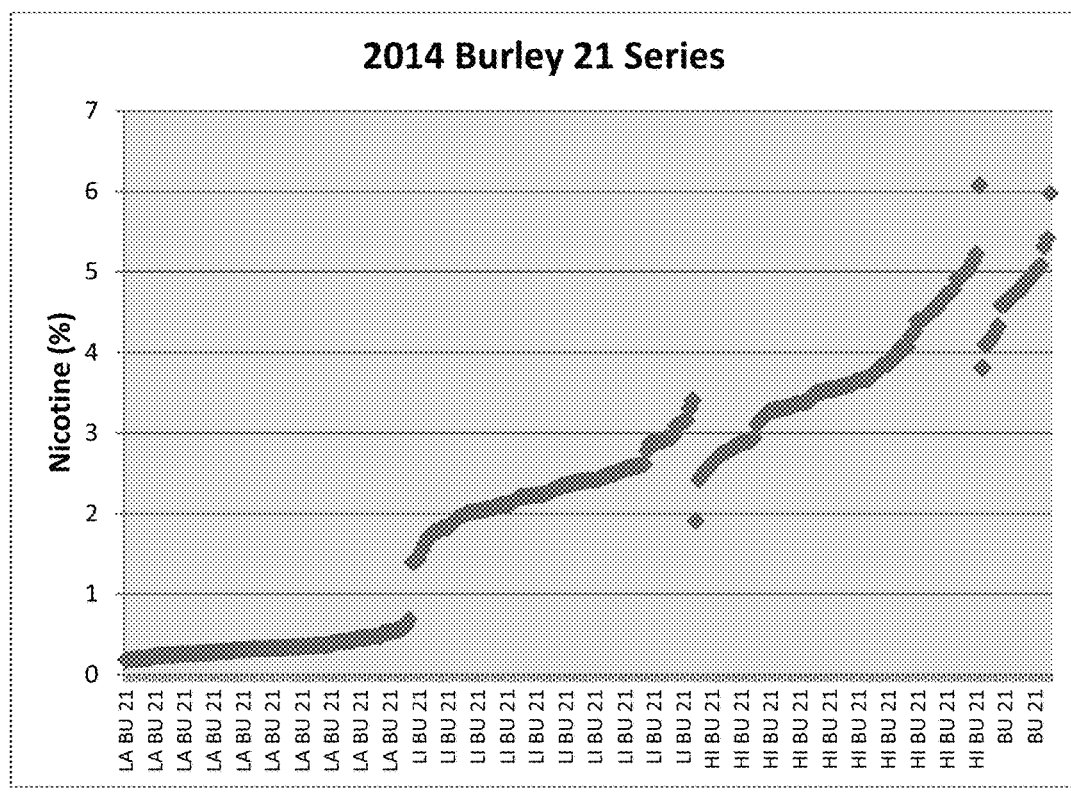
FIG. 5 shows percent nicotine levels of isogenic BU21 low alkaloid series (LA BU21, LI BU21, HI BU21, and BU21) in a 2014 field test.
Figure 6:
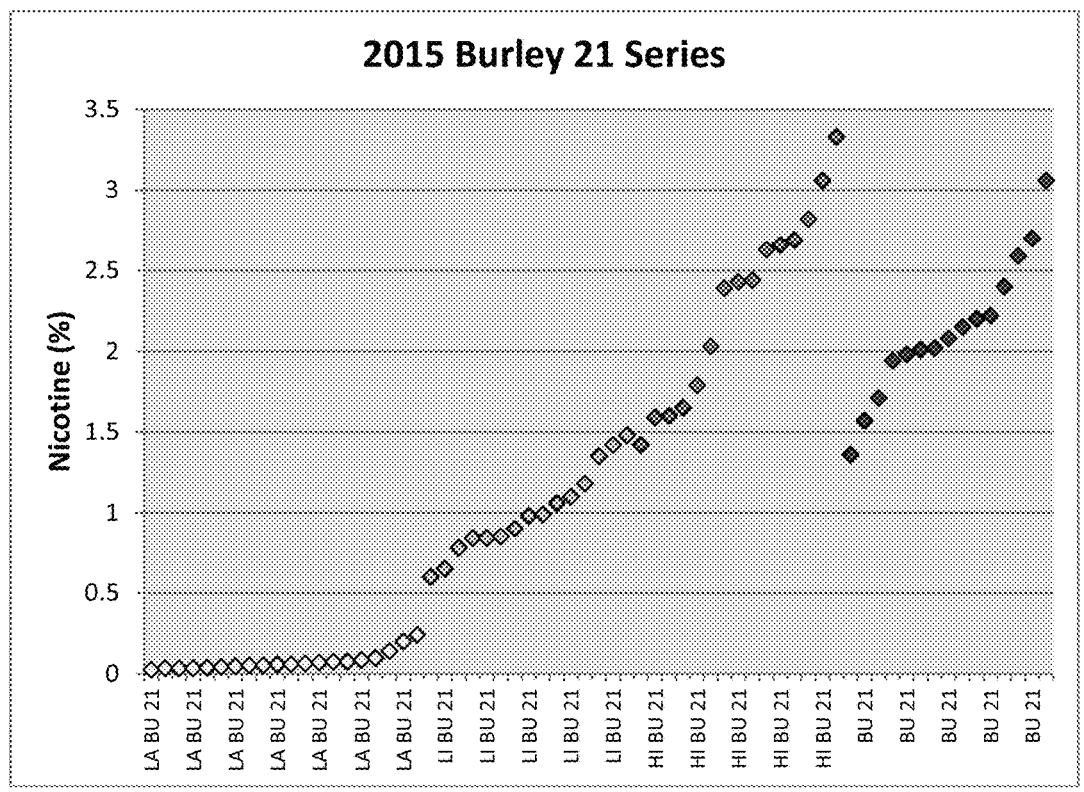
FIG. 6 shows percent nicotine levels of isogenic BU21 low alkaloid series (LA BU21, LI BU21, HI BU21, and BU21) in a 2015 field test.

Moreover, groups of isogenic BU21 low alkaloid series germplasm (LA BU21, LI BU21, HI BU21, and BU21) were tested across two years. The low alkaloid trait is not affected by year-to-year variations in leaf alkaloid levels. Shown is FIGS. 5 and 6, the percent reduction of nicotine content appeared consistent across two years, illustrating that the low alkaloid trait is not impacted by environmental factors or field conditions.

TABLE 12

Nic1 and Nic2 genotypes and alkaloid measurements of individual plants of a larger $F_2$ population segregating for nic1 and nic2 ((LA Burley 21 × TN 90 LC) (X)). N/S represent no sample. Asterisks represent four pairs (8 total having plant Nos: 163 and 164, 174 and 175, 361 and 362, 481 and 482, also in bold) of adjacent plants where DNA or leaf samples were likely switched during either sampling, processing or analysis stage. Each of the four pairs of plants were side by side in the field.

| Plant No. | Nic1 (Present = 1, Deleted = 0) | Nic2 (Present = 1, Deleted = 0) | Percent Nicotine | Percent Total Alkaloids |
|---|---|---|---|---|
| 1 | 1 | 1 | 1.33 | 1.389 |
| 2 | 1 | 1 | 1.59 | 1.66 |
| 3 | 0 | 1 | 0.72 | 0.7511 |
| 4 | 1 | 1 | 2.59 | 2.753 |
| 5 | 1 | 0 | 0.81 | 0.8422 |
| 6 | 1 | 1 | 1.04 | 1.096 |
| 7 | 1 | 1 | 1.76 | 1.843 |
| 8 | 1 | 1 | 1.07 | 1.121 |
| 9 | 1 | 0 | 1.85 | 1.938 |
| 10 | 1 | 1 | 1.58 | 1.662 |
| 11 | 1 | 0 | 1.1 | 1.147 |
| 12 | 1 | 0 | 0.68 | 0.7045 |
| 13 | 1 | 1 | 1.33 | 1.39 |
| 14 | 1 | 0 | 1.77 | 1.828 |
| 15 | 1 | 1 | 1.83 | 1.93 |
| 16 | 1 | 1 | 3.34 | 3.513 |
| 17 | 0 | 0 | 0.059 | 0.0643 |
| 18 | 1 | 1 | 3.36 | 3.543 |
| 19 | 0 | 0 | 0.062 | 0.0661 |
| 20 | 1 | 1 | 2.31 | 2.437 |
| 21 | 1 | 0 | 1.23 | 1.286 |
| 22 | 1 | 0 | 1.61 | 1.701 |
| 23 | 1 | 1 | 1.18 | 1.241 |
| 24 | 0 | 0 | 0.106 | 0.1099 |
| 25 | 0 | 1 | 1.41 | 1.487 |
| 26 | 1 | 1 | 2.47 | 2.6 |
| 27 | 1 | 1 | 2.16 | 2.245 |
| 28 | 1 | 1 | 2.22 | 2.334 |
| 29 | 1 | 0 | 2.54 | 2.667 |
| 30 | 1 | 1 | 1.37 | 1.429 |
| 31 | 1 | 1 | 1.86 | 1.956 |
| 32 | 1 | 1 | 1.68 | 1.762 |
| 33 | 1 | 0 | 1.91 | 1.996 |
| 34 | 1 | 1 | 2.89 | 3.051 |
| 35 | 0 | 1 | 1.15 | 1.205 |
| 36 | 1 | 1 | 2.92 | 3.064 |
| 37 | 1 | 0 | 2.84 | 3.005 |
| 38 | 0 | 1 | 1.49 | 1.566 |
| 39 | 0 | 0 | 0.17 | 0.1796 |
| 40 | 1 | 0 | 3.02 | 3.211 |
| 41 | 1 | 0 | 1.29 | 1.35 |
| 42 | 1 | 1 | 1.73 | 1.805 |
| 43 | 1 | 0 | 1.37 | 1.469 |
| 44 | 1 | 1 | 2.18 | 2.279 |
| 45 | 0 | 0 | 0.16 | 0.1719 |
| 46 | 1 | 0 | 2.38 | 2.495 |
| 47 | 1 | 1 | 2.34 | 2.455 |
| 48 | 1 | 0 | 1.39 | 1.455 |
| 49 | 1 | 0 | 2.9 | 3.044 |
| 50 | 0 | 1 | 2.18 | 2.307 |
| 51 | 0 | 1 | 1.34 | 1.393 |
| 52 | 1 | 0 | 1.9 | 1.98 |
| 53 | 1 | 1 | 1.49 | 1.566 |

TABLE 12-continued

Nic1 and Nic2 genotypes and alkaloid measurements of individual plants of a larger $F_2$ population segregating for nic1 and nic2 ((LA Burley 21 × TN 90 LC) (X)). N/S represent no sample. Asterisks represent four pairs (8 total having plant Nos: 163 and 164, 174 and 175, 361 and 362, 481 and 482, also in bold) of adjacent plants where DNA or leaf samples were likely switched during either sampling, processing or analysis stage. Each of the four pairs of plants were side by side in the field.

| Plant No. | Nic1 (Present = 1, Deleted = 0) | Nic2 (Present = 1, Deleted = 0) | Percent Nicotine | Percent Total Alkaloids |
|---|---|---|---|---|
| 54 | 1 | 1 | 2.22 | 2.347 |
| 55 | 1 | 1 | 3.21 | 3.359 |
| 56 | 1 | 1 | 3.67 | 3.862 |
| 57 | 1 | 1 | 2.07 | 2.17 |
| 58 | 0 | 1 | 0.83 | 0.8704 |
| 59 | 1 | 1 | 2.37 | 2.492 |
| 60 | 1 | 1 | 2.25 | 2.395 |
| 61 | 1 | 1 | 2.53 | 2.678 |
| 62 | 1 | 1 | 2.19 | 2.326 |
| 63 | 1 | 1 | 1.92 | 1.997 |
| 64 | 1 | 1 | 3.06 | 3.229 |
| 65 | 1 | 1 | 3.2 | 3.369 |
| 66 | 1 | 1 | 2.83 | 2.997 |
| 67 | 1 | 1 | 4.07 | 4.257 |
| 68 | 1 | 1 | 2.4 | 2.498 |
| 69 | 0 | 1 | 1.66 | 1.734 |
| 70 | 1 | 1 | 1.93 | 2.045 |
| 71 | 1 | 1 | 3.79 | 3.99 |
| 72 | 0 | 0 | 0.079 | 0.0849 |
| 73 | 1 | 1 | 2.17 | 2.289 |
| 74 | 1 | 0 | 3.58 | 3.778 |
| 75 | 1 | 1 | 2.63 | 2.76 |
| 76 | 0 | 1 | 1.52 | 1.603 |
| 77 | 1 | 1 | 3.04 | 3.211 |
| 78 | 1 | 1 | 2.82 | 2.979 |
| 79 | 1 | 1 | 2.6 | 2.74 |
| 80 | 1 | 1 | 2.48 | 2.597 |
| 81 | 1 | 1 | 1.88 | 1.977 |
| 82 | 1 | 1 | 2.98 | 3.106 |
| 83 | 0 | 1 | 0.99 | 1.0255 |
| 84 | 0 | 0 | 0.3 | 0.3194 |
| 85 | 1 | 1 | 1.79 | 1.873 |
| 86 | 1 | 1 | 2.37 | 2.477 |
| 87 | 1 | 1 | 2.79 | 2.932 |
| 88 | 1 | 1 | 2.14 | 2.301 |
| 89 | 1 | 1 | 4.35 | 4.588 |
| 90 | 0 | 0 | 0.09 | 0.0972 |
| 91 | 0 | 1 | 1.59 | 1.67 |
| 92 | 1 | 0 | 1.71 | 1.789 |
| 93 | 1 | 1 | 3.94 | 4.114 |
| 94 | 1 | 1 | 2.65 | 2.755 |
| 95 | 0 | 1 | 1.14 | 1.211 |
| 96 | 1 | 0 | 2.14 | 2.248 |
| 97 | 1 | 1 | 2.62 | 2.743 |
| 98 | 1 | 0 | 0.95 | 0.9865 |
| 99 | 1 | 1 | 2.61 | 2.729 |
| 100 | 1 | 1 | 3.33 | 3.485 |
| 101 | 1 | 0 | 2.77 | 2.878 |
| 102 | 1 | 1 | 2.31 | 2.424 |
| 103 | 0 | 1 | 0.49 | 0.5099 |
| 104 | 1 | 1 | 2.5 | 2.611 |
| 105 | 0 | 1 | 0.97 | 1.012 |
| 106 | 1 | 1 | 2.29 | 2.404 |
| 107 | 1 | 1 | 1.11 | 1.16 |
| 108 | 1 | 0 | 1.87 | 1.947 |
| 109 | 0 | 1 | 0.95 | 1 |
| 110 | 1 | 1 | 3.05 | 3.209 |
| 111 | 1 | 0 | 3.28 | 3.437 |
| 112 | 1 | 0 | 3.46 | 3.637 |
| 113 | 1 | 1 | 4.33 | 4.594 |
| 114 | 1 | 1 | 4.35 | 4.552 |
| 115 | 1 | 1 | 3.56 | 3.746 |
| 116 | 1 | 1 | 1.85 | 1.93 |
| 117 | 1 | 1 | 5.94 | 6.305 |
| 118 | 0 | 1 | 1.47 | 1.559 |
| 119 | 1 | 1 | 3.8 | 4.028 |
| 120 | 0 | 1 | 1.9 | 2.007 |
| 121 | 1 | 0 | 3.38 | 3.573 |
| 122 | 0 | 0 | 0.3 | 0.3191 |
| 123 | 1 | 1 | 4.04 | 4.245 |
| 124 | 1 | 1 | 3.4 | 3.622 |
| 125 | 0 | 1 | 1.09 | 1.141 |
| 126 | 1 | 0 | 2.71 | 2.828 |
| 127 | 1 | 1 | 4.93 | 5.178 |
| 128 | 1 | 0 | 2.65 | 2.801 |
| 129 | 1 | 1 | 1.62 | 1.693 |
| 130 | 1 | 0 | 2.13 | 2.232 |
| 131 | 0 | 1 | 2.64 | 2.789 |
| 132 | 1 | 1 | 3.17 | 3.329 |
| 133 | 0 | 1 | 1.99 | 2.108 |
| 134 | 1 | 1 | 2.28 | 2.377 |
| 135 | 1 | 1 | 3.85 | 4.019 |
| 136 | 1 | 1 | 3.62 | 3.792 |
| 137 | 1 | 0 | 3.19 | 3.355 |
| 138 | 0 | 1 | 1.49 | 1.565 |
| 139 | 1 | 1 | 4.33 | 4.516 |
| 140 | 1 | 1 | 3.88 | 4.097 |
| 141 | 1 | 1 | 5.68 | 6.003 |
| 142 | 1 | 1 | 3.15 | 3.292 |
| 143 | 1 | 0 | 2.35 | 2.456 |
| 144 | 1 | 0 | 3.63 | 3.786 |
| 145 | 1 | 1 | 3.32 | 3.532 |
| 146 | 1 | 1 | 3.26 | 3.407 |
| 147 | 1 | 1 | 3.37 | 3.507 |
| 148 | 1 | 0 | 3.21 | 3.388 |
| 149 | 1 | 1 | 3.7 | 3.873 |
| 150 | 0 | 0 | 0.4 | 0.4279 |
| 151 | 1 | 1 | 1.41 | 1.482 |
| 152 | 1 | 1 | 2.18 | 2.273 |
| 153 | 1 | 1 | 2.58 | 2.725 |
| 154 | 0 | 1 | 2.89 | 3.088 |
| 155 | 1 | 1 | 1.51 | 1.593 |
| 156 | 0 | 1 | 2.03 | 2.143 |
| 157 | 0 | 1 | 2.03 | 2.151 |
| 158 | 1 | 0 | 1.27 | 1.323 |
| 159 | 1 | 1 | 1.62 | 1.734 |
| 160 | 1 | 1 | 4.48 | 4.67 |
| 161 | 1 | 1 | 1 | 1.045 |
| 162 | 1 | 1 | 3.17 | 3.309 |
| 163* | 1 | 1 | 0.18 | 0.1906 |
| 164* | 0 | 1 | 2.38 | 2.493 |
| 165 | 1 | 1 | 3.62 | 3.745 |
| 166 | 1 | 1 | N/S | N/S |
| 167 | 1 | 0 | 2.62 | 2.717 |
| 168 | 1 | 1 | 2.31 | 2.428 |
| 169 | 1 | 0 | 2.52 | 2.645 |
| 170 | 1 | 1 | 4.35 | 4.527 |
| 171 | 1 | 0 | 1.66 | 1.741 |
| 172 | 1 | 1 | 3.03 | 3.159 |
| 173 | 1 | 0 | 3.2 | 3.343 |
| 174* | 1 | 1 | 0.059 | 0.0653 |
| 175* | 0 | 0 | 4.03 | 4.197 |
| 176 | 1 | 1 | 2.85 | 3.01 |
| 177 | 1 | 1 | 2.91 | 3.086 |
| 178 | 1 | 1 | 4.21 | 4.395 |
| 179 | 1 | 1 | 1.09 | 1.154 |
| 180 | 1 | 1 | 1.15 | 1.206 |
| 181 | 1 | 0 | 3.2 | 3.345 |
| 182 | 1 | 1 | 3.28 | 3.406 |
| 183 | 1 | 1 | 3.17 | 3.324 |
| 184 | 1 | 0 | 3.24 | 3.392 |
| 185 | 1 | 1 | 0.94 | 0.987 |
| 186 | 1 | 1 | 3.95 | 4.123 |
| 187 | 1 | 0 | 0.68 | 0.7094 |
| 188 | 0 | 1 | 1.94 | 2.007 |
| 189 | 1 | 1 | 0.46 | 0.4809 |

TABLE 12-continued

Nic1 and Nic2 genotypes and alkaloid measurements of individual plants of a larger $F_2$ population segregating for nic1 and nic2 ((LA Burley 21 × TN 90 LC) (X)). N/S represent no sample. Asterisks represent four pairs (8 total having plant Nos: 163 and 164, 174 and 175, 361 and 362, 481 and 482, also in bold) of adjacent plants where DNA or leaf samples were likely switched during either sampling, processing or analysis stage. Each of the four pairs of plants were side by side in the field.

| Plant No. | Nic1 (Present = 1, Deleted = 0) | Nic2 (Present = 1, Deleted = 0) | Percent Nicotine | Percent Total Alkaloids |
|---|---|---|---|---|
| 190 | 0 | 1 | 2.28 | 2.356 |
| 191 | 1 | 1 | 2.25 | 2.336 |
| 192 | 1 | 0 | 2.74 | 2.842 |
| 193 | 1 | 1 | 3.9 | 4.091 |
| 194 | 1 | 1 | 3.39 | 3.578 |
| 195 | 1 | 0 | 2.59 | 2.698 |
| 196 | 0 | 0 | 0.131 | 0.1383 |
| 197 | 1 | 1 | 2.28 | 2.365 |
| 198 | 1 | 0 | 2.27 | 2.395 |
| 199 | 0 | 0 | 0.1 | 0.1063 |
| 200 | 1 | 1 | 2.39 | 2.496 |
| 201 | 0 | 1 | 1.02 | 1.09 |
| 202 | 1 | 1 | 1.99 | 2.09 |
| 203 | 1 | 1 | 3.44 | 3.594 |
| 204 | 1 | 1 | 3.05 | 3.167 |
| 205 | 0 | 1 | 0.85 | 0.8839 |
| 206 | 0 | 1 | 2.18 | 2.331 |
| 207 | 1 | 1 | 1.89 | 1.971 |
| 208 | 1 | 1 | 1.37 | 1.445 |
| 209 | 1 | 1 | 3.26 | 3.432 |
| 210 | 1 | 1 | 1.28 | 1.3224 |
| 211 | 0 | 1 | 1.86 | 1.966 |
| 212 | 1 | 1 | 1.53 | 1.59 |
| 213 | 0 | 0 | 0.142 | 0.1513 |
| 214 | 1 | 1 | 2.22 | 2.331 |
| 215 | 1 | 1 | 2.94 | 3.075 |
| 216 | 0 | 1 | 1.72 | 1.801 |
| 217 | 1 | 1 | 3.89 | 4.044 |
| 218 | 1 | 1 | 4.47 | 4.691 |
| 219 | 0 | 1 | 1.63 | 1.696 |
| 220 | 1 | 0 | 3.28 | 3.432 |
| 221 | 1 | 0 | 1.14 | 1.193 |
| 222 | 1 | 1 | 3.91 | 4.089 |
| 223 | 1 | 0 | 0.87 | 0.9002 |
| 224 | 1 | 1 | 1.8 | 1.891 |
| 225 | 1 | 1 | 2.25 | 2.369 |
| 226 | 1 | 0 | 2.59 | 2.738 |
| 227 | 0 | 1 | 0.89 | 0.933 |
| 228 | 0 | 1 | 0.64 | 0.669 |
| 227B | 1 | 1 | 1.38 | 1.439 |
| 228B | 1 | 1 | 3.25 | 3.421 |
| 229 | 1 | 0 | 3.57 | 3.71 |
| 230 | 0 | 1 | 2.43 | 2.583 |
| 231 | 1 | 1 | 3.23 | 3.398 |
| 232 | 1 | 1 | 4.85 | 5.187 |
| 233 | 0 | 1 | 1.09 | 1.138 |
| 234 | 0 | 0 | 0.24 | 0.2521 |
| 235 | 1 | 1 | 2.49 | 2.597 |
| 236 | 1 | 1 | 4.07 | 4.327 |
| 237 | 0 | 1 | 1.17 | 1.235 |
| 238 | 0 | 0 | 0.16 | 0.1683 |
| 239 | 1 | 1 | 3.18 | 3.323 |
| 240 | 1 | 0 | 2.39 | 2.5 |
| 241 | 1 | 1 | 1.72 | 1.805 |
| 242 | 0 | 1 | 0.95 | 0.992 |
| 243 | 0 | 1 | 0.75 | 0.787 |
| 244 | 1 | 1 | 2.28 | 2.398 |
| 245 | 1 | 1 | 1.89 | 1.989 |
| 246 | 1 | 0 | 3.91 | 4.084 |
| 247 | 1 | 1 | 2.53 | 2.648 |
| 248 | 0 | 1 | 0.68 | 0.7146 |
| 249 | 1 | 1 | 2.82 | 2.966 |
| 250 | 1 | 1 | 1.76 | 1.841 |
| 251 | 0 | 0 | 0.18 | 0.1936 |
| 252 | 1 | 1 | 1.39 | 1.452 |
| 253 | 1 | 1 | 3.54 | 3.722 |
| 254 | 1 | 1 | 4.05 | 4.247 |
| 255 | 1 | 1 | 2.09 | 2.192 |
| 256 | 1 | 1 | 1.47 | 1.551 |
| 257 | 1 | 0 | 2.54 | 2.677 |
| 258 | 1 | 1 | 3.83 | 4.002 |
| 259 | 1 | 0 | 1.23 | 1.301 |
| 260 | 1 | 1 | 1.92 | 2.017 |
| 261 | 1 | 1 | 2.17 | 2.323 |
| 262 | 1 | 0 | 2.41 | 2.552 |
| 263 | 1 | 0 | 2.3 | 2.435 |
| 262B | 1 | 0 | 1.34 | 1.408 |
| 263B | 1 | 1 | 3.39 | 3.577 |
| 264 | 0 | 1 | 1.98 | 2.093 |
| 265 | 0 | 1 | 0.8 | 0.854 |
| 266 | 1 | 1 | 1.76 | 1.863 |
| 267 | 1 | 1 | 1.87 | 1.989 |
| 268 | 0 | 0 | 0.19 | 0.2031 |
| 269 | 0 | 0 | 0.12 | 0.1293 |
| 270 | 0 | 1 | 0.57 | 0.607 |
| 271 | 0 | 0 | 0.139 | 0.1481 |
| 272 | 1 | 0 | 1.81 | 1.893 |
| 273 | 1 | 0 | 2.13 | 2.244 |
| 274 | 0 | 1 | 0.52 | 0.5523 |
| 275 | 0 | 1 | 1.7 | 1.805 |
| 276 | 1 | 0 | 1.83 | 1.922 |
| 277 | 1 | 1 | 2 | 2.101 |
| 278 | 0 | 1 | 0.91 | 0.9535 |
| 279 | 1 | 1 | 3.25 | 3.439 |
| 280 | 1 | 1 | 3.45 | 3.586 |
| 281 | 1 | 1 | 4.62 | 4.807 |
| 282 | 1 | 1 | 3.41 | 3.566 |
| 283 | 0 | 1 | 1.34 | 1.407 |
| 284 | 1 | 1 | 2.43 | 2.556 |
| 285 | 1 | 1 | 1.44 | 1.514 |
| 286 | 1 | 1 | 2.49 | 2.614 |
| 287 | 0 | 0 | 0.137 | 0.1445 |
| 288 | 1 | 1 | 1.78 | 1.863 |
| 289 | 0 | 1 | 0.53 | 0.5681 |
| 290 | 1 | 1 | N/S | N/S |
| 291 | 0 | 1 | 0.73 | 0.775 |
| 292 | 1 | 1 | 1.43 | 1.504 |
| 293 | 1 | 1 | 1.92 | 2.012 |
| 294 | 0 | 1 | 0.51 | 0.5388 |
| 295 | 1 | 0 | 2.07 | 2.181 |
| 296 | 1 | 1 | 1.4 | 1.463 |
| 297 | 1 | 1 | 4.21 | 4.548 |
| 298 | 1 | 0 | 3.11 | 3.225 |
| 299 | 1 | 1 | 3.93 | 4.158 |
| 300 | 1 | 1 | 1.99 | 2.062 |
| 301 | 0 | 1 | 0.56 | 0.5858 |
| 302 | 1 | 1 | 1.93 | 2.018 |
| 303 | 1 | 1 | 1.06 | 1.114 |
| 304 | 1 | 1 | 6.89 | 7.302 |
| 305 | 1 | 0 | 2.25 | 2.366 |
| 306 | 1 | 0 | 1.42 | 1.479 |
| 307 | 1 | 0 | 2.39 | 2.591 |
| 308 | 1 | 1 | 2.52 | 2.635 |
| 309 | 1 | 0 | 1.84 | 1.933 |
| 310 | 1 | 1 | 2.29 | 2.412 |
| 311 | 1 | 1 | 1.62 | 1.707 |
| 312 | 0 | 1 | 1.89 | 1.988 |
| 313 | 1 | 1 | 2.48 | 2.577 |
| 314 | 0 | 0 | 1.01 | 1.056 |
| 315 | 1 | 1 | 2.21 | 2.334 |
| 316 | 1 | 1 | 1.54 | 1.617 |
| 317 | 1 | 1 | N/S | N/S |
| 318 | 0 | 1 | 0.65 | 0.6821 |
| 319 | 1 | 1 | 3.32 | 3.493 |
| 320 | 1 | 0 | 2.68 | 2.8 |
| 321 | 1 | 1 | 2.71 | 2.835 |

TABLE 12-continued

Nic1 and Nic2 genotypes and alkaloid measurements of individual plants of a larger F₂ population segregating for nic1 and nic2 ((LA Burley 21 × TN 90 LC) (X)). N/S represent no sample. Asterisks represent four pairs (8 total having plant Nos: 163 and 164, 174 and 175, 361 and 362, 481 and 482, also in bold) of adjacent plants where DNA or leaf samples were likely switched during either sampling, processing or analysis stage. Each of the four pairs of plants were side by side in the field.

| Plant No. | Nic1 (Present = 1, Deleted = 0) | Nic2 (Present = 1, Deleted = 0) | Percent Nicotine | Percent Total Alkaloids |
|---|---|---|---|---|
| 322 | 1 | 0 | 1.97 | 2.068 |
| 323 | 1 | 1 | 2.76 | 2.905 |
| 324 | 1 | 0 | 3.92 | 4.122 |
| 325 | 1 | 0 | 2.56 | 2.724 |
| 326 | 1 | 1 | 3.18 | 3.355 |
| 327 | 0 | 1 | 2.08 | 2.165 |
| 328 | 1 | 0 | 2.77 | 2.89 |
| 329 | 1 | 1 | 2.11 | 2.216 |
| 330 | 1 | 0 | 1.81 | 1.878 |
| 331 | 0 | 0 | 0.2 | 0.2096 |
| 332 | 1 | 1 | 1.8 | 1.894 |
| 333 | 0 | 1 | 0.75 | 0.7875 |
| 334 | 1 | 0 | 2.78 | 2.92 |
| 335 | 0 | 0 | 0.19 | 0.2044 |
| 336 | 1 | 1 | 2.2 | 2.31 |
| 337 | 1 | 1 | 1.54 | 1.606 |
| 338 | 0 | 0 | 0.19 | 0.1986 |
| 339 | 1 | 1 | 2.05 | 2.153 |
| 340 | 1 | 0 | 1.57 | 1.644 |
| 341 | 1 | 1 | 2.64 | 2.768 |
| 342 | 1 | 1 | 2.4 | 2.522 |
| 343 | 1 | 1 | 2.1 | 2.213 |
| 344 | 1 | 1 | 2.83 | 2.989 |
| 345 | 1 | 0 | 2.77 | 2.899 |
| 346 | 1 | 1 | 1.44 | 1.509 |
| 347 | | | 2.89 | 3.042 |
| 348 | 1 | 1 | 1.76 | 1.841 |
| 349 | 0 | 1 | 0.59 | 0.6235 |
| 350 | 1 | 1 | 3.62 | 3.804 |
| 351 | | | 0.67 | 0.707 |
| 352 | 1 | 0 | 2.25 | 2.352 |
| 353 | 1 | 1 | 1.7 | 1.786 |
| 354 | 1 | 1 | 2.36 | 2.463 |
| 355 | 1 | 1 | N/S | N/S |
| 356 | 1 | 1 | 3.36 | 3.549 |
| 357 | 1 | 1 | 1.63 | 1.706 |
| 358 | 0 | 1 | 0.84 | 0.887 |
| 359 | 0 | 1 | 0.5 | 0.5223 |
| 360 | 1 | 1 | 2.44 | 2.568 |
| 361* | 0 | 1 | 1.86 | 1.931 |
| 362* | 0 | 0 | 2.98 | 3.122 |
| 363 | 0 | 0 | 0.072 | 0.0754 |
| 364 | 0 | 1 | 1.64 | 1.739 |
| 365 | 1 | 1 | 3.4 | 3.602 |
| 366 | 1 | 0 | 2.72 | 2.872 |
| 367 | 0 | 1 | 1.12 | 1.205 |
| 368 | 1 | 1 | 3 | 3.207 |
| 369 | 1 | 1 | 1.45 | 1.542 |
| 370 | 1 | 1 | 4.65 | 4.975 |
| 371 | 1 | 1 | 3.1 | 3.271 |
| 372 | 1 | 1 | 1.2 | 1.252 |
| 373 | 1 | 1 | 1.94 | 2.049 |
| 374 | 0 | 0 | 0.24 | 0.2523 |
| 375 | 1 | 1 | 3.4 | 3.528 |
| 376 | 1 | 0 | 2.73 | 2.863 |
| 377 | 0 | 1 | 0.57 | 0.5979 |
| 378 | 1 | 1 | 2.34 | 2.447 |
| 379 | 1 | 1 | 2.9 | 3.073 |
| 380 | 1 | 1 | 2.03 | 2.156 |
| 381 | 1 | 1 | 2.07 | 2.177 |
| 382 | 0 | 1 | 1.23 | 1.301 |
| 383 | 1 | 1 | 2.42 | 2.554 |
| 384 | 1 | 1 | 3.32 | 3.518 |
| 385 | 1 | 1 | 2.18 | 2.293 |
| 386 | 1 | 1 | 1.58 | 1.668 |
| 387 | 0 | 1 | 1.21 | 1.285 |
| 388 | 0 | 0 | 0.074 | 0.0789 |
| 389 | 1 | 1 | 1.65 | 1.725 |
| 390 | 1 | 1 | 2.36 | 2.507 |
| 391 | 1 | 1 | 1.94 | 2.055 |
| 392 | 1 | 1 | 2 | 2.102 |
| 393 | 1 | 1 | 2.61 | 2.705 |
| 394 | 0 | 1 | 1 | 1.06 |
| 395 | 1 | 1 | 2.53 | 2.641 |
| 396 | 1 | 1 | 1.03 | 1.081 |
| 397 | 0 | 0 | 0.136 | 0.1417 |
| 398 | 1 | 1 | 0.99 | 1.033 |
| 399 | 1 | 1 | 1.96 | 2.062 |
| 400 | 0 | 0 | 0.113 | 0.1193 |
| 401 | 1 | 1 | 1.75 | 1.841 |
| 402 | 1 | 1 | 2.34 | 2.442 |
| 403 | 1 | 1 | 1.92 | 2.002 |
| 404 | 1 | 1 | 3.87 | 4.06 |
| 405 | 1 | 1 | 2.94 | 3.068 |
| 406 | 1 | 1 | 1.15 | 1.204 |
| 407 | 1 | 1 | 3.15 | 3.359 |
| 408 | 1 | 1 | 1.83 | 1.923 |
| 409 | 1 | 1 | 2.28 | 2.402 |
| 410 | 1 | 1 | 2.76 | 2.906 |
| 411 | 1 | 1 | 1.88 | 1.994 |
| 412 | 1 | 1 | 1.28 | 1.342 |
| 413 | 1 | 1 | 1.12 | 1.175 |
| 414 | 0 | 1 | 1.28 | 1.341 |
| 415 | 1 | 1 | 2.22 | 2.334 |
| 416 | 0 | 1 | 1.05 | 1.099 |
| 417 | 1 | 1 | 3.01 | 3.148 |
| 418 | 1 | 1 | 3.27 | 3.444 |
| 419 | 1 | 1 | 1.77 | 1.86 |
| 420 | 1 | 1 | 1.44 | 1.497 |
| 421 | 0 | 1 | 0.55 | 0.5777 |
| 422 | 1 | 0 | 2.7 | 2.825 |
| 423 | 1 | 1 | 1.24 | 1.315 |
| 424 | 1 | 1 | 2.95 | 3.106 |
| 425 | 0 | 1 | 0.63 | 0.6607 |
| 426 | 1 | 1 | 2.88 | 3.014 |
| 427 | 1 | 1 | 2.31 | 2.455 |
| 428 | 1 | 0 | 1.92 | 1.994 |
| 429 | 1 | 1 | 3.05 | 3.232 |
| 430 | 1 | 1 | 1.76 | 1.88 |
| 431 | 0 | 0 | 0.11 | 0.1164 |
| 432 | 0 | 1 | 0.78 | 0.8129 |
| 433 | 0 | 1 | 2.01 | 2.134 |
| 434 | 1 | 1 | 1.98 | 2.095 |
| 435 | | | 1.71 | 1.801 |
| 436 | 1 | 0 | 3.27 | 3.447 |
| 437 | 0 | 1 | 0.89 | 0.944 |
| 438 | 1 | 1 | 2.9 | 3.049 |
| 439 | 0 | 0 | 0.18 | 0.1905 |
| 440 | 1 | 1 | 4.12 | 4.367 |
| 441 | 0 | 1 | 1.53 | 1.623 |
| 442 | 1 | 1 | 4.07 | 4.315 |
| 443 | 0 | 1 | 1.35 | 1.429 |
| 444 | 1 | 0 | 2.98 | 3.12 |
| 445 | 1 | 1 | 4.98 | 5.272 |
| 446 | 0 | 1 | 1.22 | 1.288 |
| 447 | 1 | 1 | 4.34 | 4.578 |
| 448 | 1 | 1 | 2.89 | 3.028 |
| 449 | 1 | 1 | 5.8 | 6.135 |
| 450 | 1 | 1 | 4.34 | 4.553 |
| 451 | 1 | 0 | 3.6 | 3.791 |
| 452 | 1 | 1 | 4.67 | 4.947 |
| 453 | 0 | 1 | 1.83 | 1.918 |
| 454 | 1 | 1 | 2.6 | 2.692 |
| 455 | 1 | 1 | 5.03 | 5.301 |
| 456 | 1 | 1 | 4.41 | 4.695 |
| 457 | 1 | 0 | 2.62 | 2.741 |

TABLE 12-continued

Nic1 and Nic2 genotypes and alkaloid measurements of individual plants of a larger $F_2$ population segregating for nic1 and nic2 ((LA Burley 21 x TN 90 LC) (X)). N/S represent no sample. Asterisks represent four pairs (8 total having plant Nos: 163 and 164, 174 and 175, 361 and 362, 481 and 482, also in bold) of adjacent plants where DNA or leaf samples were likely switched during either sampling, processing or analysis stage. Each of the four pairs of plants were side by side in the field.

| Plant No. | Nic1 (Present = 1, Deleted = 0) | Nic2 (Present = 1, Deleted = 0) | Percent Nicotine | Percent Total Alkaloids |
|---|---|---|---|---|
| 458 | 0 | 0 | 0.133 | 0.1425 |
| 459 | 0 | 1 | 0.53 | 0.5534 |
| 460 | 0 | 1 | 0.63 | 0.6663 |
| 461 | 0 | 1 | 2.78 | 2.943 |
| 462 | 1 | 1 | 2.64 | 2.785 |
| 463 | 0 | 1 | 1.23 | 1.296 |
| 464 | 0 | 1 | 1.55 | 1.629 |
| 465 | 1 | 1 | 2.49 | 2.626 |
| 466 | 1 | 1 | 2.8 | 2.936 |
| 467 | 0 | 0 | 0.19 | 0.2026 |
| 468 | 0 | 1 | 1.91 | 2.029 |
| 469 | 1 | 1 | 1.37 | 1.442 |
| 470 | 0 | 1 | 1.29 | 1.375 |
| 471 | 1 | 1 | 3.74 | 3.919 |
| 472 | 0 | 1 | 1.67 | 1.78 |
| 473 | 1 | 1 | 1.39 | 1.479 |
| 474 | 1 | 1 | 0.88 | 0.926 |
| 475 |  |  | 2.53 | 2.679 |
| 476 | 1 | 1 | 3.59 | 3.756 |
| 477 | 1 | 1 | 3.96 | 4.196 |
| 478 | 1 | 1 | 1.59 | 1.679 |
| 479 | 0 | 1 | 2.27 | 2.385 |
| 480 | 0 | 0 | 0.108 | 0.1147 |
| 481* | 0 | 1 | 2.21 | 2.363 |
| 482* | 1 | 1 | 0.54 | 0.5726 |
| 483 | 1 | 1 | 1.76 | 1.854 |
| 484 | 1 | 1 | 3.34 | 3.512 |
| 485 | 1 | 1 | 1.4 | 1.468 |
| 486 | 1 | 0 | 0.87 | 0.9085 |
| 487 | 0 | 1 | 0.38 | 0.3976 |
| 488 | 1 | 1 | 2.53 | 2.662 |
| 489 | 0 | 1 | 1.34 | 1.412 |
| 490 | 0 | 1 | 1.17 | 1.246 |
| 491 | 0 | 1 | 0.43 | 0.4505 |
| 492 | 1 | 0 | 3.55 | 3.741 |
| 493 | 0 | 1 | 2.16 | 2.294 |
| 494 | 1 | 1 | 2.6 | 2.736 |
| 495 | 1 | 1 | 2.73 | 2.905 |
| 496 | 1 | 1 | 2.46 | 2.591 |
| 497 | 1 | 1 | 1.8 | 1.906 |
| 498 | 0 | 1 | 0.75 | 0.7913 |
| 499 | 1 | 1 | 1.37 | 1.461 |
| 500 | 1 | 0 | 1.63 | 1.731 |
| 501 | 1 | 1 | 1.34 | 1.417 |
| 502 | 1 | 0 | 0.98 | 1.0156 |
| 503 | 1 | 1 | 0.79 | 0.8276 |
| 504 | 1 | 0 | 1.75 | 1.812 |
| 505 | 1 | 1 | 1.49 | 1.571 |
| 506 | 0 | 0 | 0.084 | 0.0892 |
| 507 | 1 | 1 | 1.2 | 1.247 |
| 508 | 1 | 0 | 1.98 | 2.081 |
| 509 | 1 | 0 | 1.03 | 1.0704 |
| 510 | 1 | 0 | 1.4 | 1.475 |
| 511 | 1 | 0 | 0.76 | 0.791 |
| 512 | 1 | 1 | 1.4 | 1.491 |
| 513 | 1 | 1 | 2.29 | 2.402 |
| 514 | 1 | 1 | 1.14 | 1.19 |
| 515 | 1 | 1 | 1 | 1.044 |
| 516 | 1 | 1 | 1.26 | 1.356 |
| 517 | 0 | 1 | 0.52 | 0.5535 |
| 518 | 1 | 1 | 0.45 | 0.4786 |
| 519 | 1 | 0 | 1.59 | 1.651 |
| 520 | 1 | 1 | 1.59 | 1.667 |
| 521 | 0 | 1 | 0.46 | 0.4803 |
| 522 | 1 | 0 | 1.1 | 1.162 |

TABLE 13

Genetic segregation of an $F_2$ segregating population ((LA Burley 21 x TN 90 LC) (X)) and average percent total alkaloid and percent nicotine levels in each of the four segregating genotypes. Both the mean and standard deviation are shown. Three plants with missing samples are excluded rendering the total number of plants analyzed to be 518.

| Genotype | Ratio Expected | Number of Plants Expected | Number of Plants Observed | Average Percent Nicotine | Std Dev (Nicotine) | Average Percent Total Alkaloid | Std Dev (Total Alkaloid) |
|---|---|---|---|---|---|---|---|
| Nic1 Nic2 | 9/16 | 291.9 | 288 | 2.55 | 1.08 | 2.68 | 1.14 |
| Nic1 nic2 | 3/16 | 97.3 | 96 | 2.25 | 0.83 | 2.36 | 0.87 |
| nic1 Nic2 | 3/16 | 97.3 | 97 | 1.30 | 0.61 | 1.37 | 0.65 |
| nic1 nic2 | 1/16 | 32.4 | 37 | 0.36 | 0.78 | 0.38 | 0.81 |

TABLE 14

A re-analysis of the segregation population in Table 12 further excluding the four plant pairs which were likely switched (plant Nos: 163 and 164, 174 and 175, 361 and 362, 481 and 482) and rendering the total plant number to be 510.

| Genotype | Ratio Expected | Number of Plants Expected | Number of Plants Observed | Average Percent Nicotine | Std Dev (Nicotine) | Average Percent Total Alkaloid | Std Dev (Total Alkaloid) |
| --- | --- | --- | --- | --- | --- | --- | --- |
| Nic1 Nic2 | 9/16 | 286.88 | 285 | 2.57 | 1.06 | 2.71 | 1.11 |
| Nic1 nic2 | 3/16 | 95.63 | 96 | 2.25 | 0.83 | 2.36 | 0.87 |
| nic1 Nic2 | 3/16 | 95.63 | 95 | 1.28 | 0.60 | 1.35 | 0.64 |
| nic1 nic2 | 1/16 | 31.88 | 34 | 0.18 | 0.16 | 0.19 | 0.17 |

Example 12

Genome Re-sequencing to Validate and Refine Sequences in the Identified Nic1 Lesion Genomic sequences of the identified Nic1 scaffold and annotated genes were re-sequenced using PacBio's SMRT sequencing technology (NT2.0). Sequence quality of Nic1 locus region (NT1.0-Scaffold0002504) was improved. Briefly, base pairs (bps) 1 to 133,550 of NT2.0-Scaffold4274 (SEQ ID No: 73) correspond to and replace NT1.0-Scaffold0002504 between bps 384,701 to 542,313 in the minus orientation. Base pairs 1 to 59,671 of NT2.0-Scaffold14415 (SEQ ID No: 74) correspond to and replace NT1.0-Scaffold0002504 between bps 288,601 to 363,040 in the minus orientation.

Additional genomic sequence data are provided in SEQ ID Nos: 75 to 82 for the 8 genes previously identified in SEQ ID Nos: 21 to 28, respectively. A new set of cDNA and protein sequences of "g100623_Scaffold0002504" are also identified (new sequences of SEQ ID No: 83 and 84 relative to previous sequences of SEQ ID No: 46 and 66, respectively).

Each and every U.S. or foreign patent, publication of patent application, non-patent literature or any other reference mentioned in this application is incorporated by reference in its entirety.

Example 13

Figure 7:
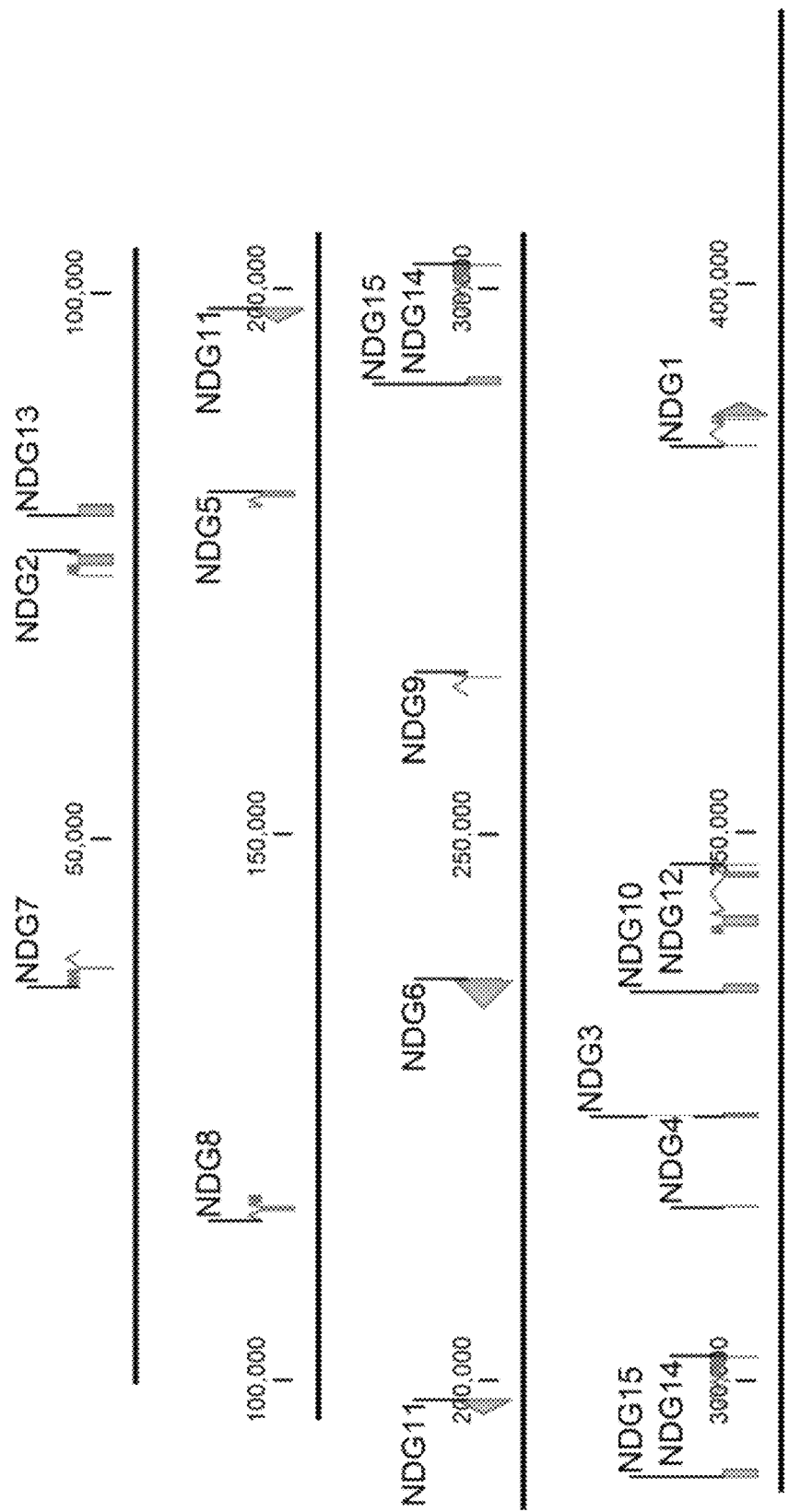
FIG. 7 shows the relative genomic position of NDG1 to NDG15 genes on SEQ ID NO: 85 which is shown in four overlapping segments (from top to bottom, nucleotide 1 to ~100 k, ~100 k to ~200 k, ~200 k to ~300 k, and ~300 k to 425 k, respectively).

Complete Sequencing of the Nic1 Lesion Region Using Bacteria Artificial Chromosome Sequencing A bacterial artificial chromosomes (BAC) walking method was used to generate the complete sequence around the Nic1 locus and further identify boundary sequences of the genomic deletion. Briefly, 21 BAC clones associated with whole-genome profiling (WGP) contigs were identified and pooled to form 3 pools of 7 BACs each. Each pool was sequenced separately on separate SMRT cells (PacBio). The sequences were assembled into 14 contigs, which were further assembled into one contig based on overlapping sequence information obtained by blasting 1000 bps on either end of each contig. The resulting reference contig was used to re-map resequencing data from BU21, HI, LI, and LA BU21 lines. A contiguous 425,001 bp region (SEQ ID NO: 85) that spans the entire Nic1 deletion was identified. Table 15 provides details of the fifteen identified gene models with functional information for the encoded proteins based on the best BLAST hit. The relative position of these fifteen genes on SEQ ID NO: 85 can be found in FIG. 7. The genomic sequences (SEQ ID NOs: 86 to 100), coding sequences (CDS; SEQ ID NOs: 101 to 115) and protein sequences (SEQ ID NOs: 116 to 130) are provided for the fifteen Nic1 Deletion Genes (NDG1 to NDG15). Among these, genomic sequence data provided in SEQ ID NOs: 86, 87, and 90 to 100 correspond to the 13 gene models previously identified in SEQ ID NOs: 28, 13, 20, 22, 11, 17, 23, 26, 21, 27, 14, 25, and 24, respectively. RNAi constructs are designed to silence NDG1 to NDG15 and are also used to make transgenic tobacco plants with lower alkaloid levels.

Example 14

Development of Additional SNP Markers for Selecting Nic1 and Nic2

To provide more efficient selection of plants that harbor nic1 and nic2 mutations, 12 SNPs (6 SNPs for each locus) flanking nic1 and nic2 deletions were identified to develop co-dominant markers. Three SNPs upstream and 3 SNPs downstream of each deletion region are used. Each of the SNP polymorphisms is less than 100 kb from the corresponding deleted region. Table 16 provides more details on the relative location and sequence polymorphism for each SNP, and also provides sequence information for 60 bps upstream and downstream of each SNP. High throughput Kompetetive Allele Specific PCR™ or KASP™ assays (LGC Genomics, Beverly, Mass.) are designed based on the identified SNPs for genotyping. These SNP markers can be used to detect plants that are heterozygous for a nic1 or nic2 deletion and can also distinguish a true homozygous deletion from a bad PCR reaction. The effectiveness of two SNP markers (Seq ID Nos. 135 and 137) for genotyping the $F_2$ population ((LA Burley 21×TN 90 LC) (X)) of Example 11 (see plant No. 1 to 72 of Table 12) is shown in Table 18.

Example 15

Identification of an ERF Gene Associated with Nic1

An ERF gene, named as "ERF-39 like" was identified 307,823 bps downstream of the Nic1 deletion region. Given this gene's close proximity, two adjoining SNP markers (SEQ ID Nos. 143 and 144) were identified for genotyping and tracking purposes. The details of the two SNPs are provided in Table 17. The genomic, cDNA, and protein sequence of the ERF-39 like gene are provided in SEQ ID Nos: 145 to 147, respectively. Plants that overexpress or downregulate the ERF-39 gene (e.g., via RNAi, artificial miRNA, chemical mutagenesis, or targeted genome editing) are made and assess the effect of this gene on plant nicotine levels.

Example 16

Development of Low-alkaloid Tobacco Plants Via Gene Silencing and Genome Editing Tobacco lines with low nicotine while maintaining high leaf quality are produced by introducing loss-of-function or null mutations into Nic1 locus or Nic2 locus via targeted genome editing technologies. Examples of genome editing techniques are Transcription activator-like effector nucleases (TALENs), meganuclease, zinc finger nuclease, and CRISPR, as described in Example 10. Genome modifications are made in commercial tobacco varieties such as TN90, K326 and Narrow Leaf Madole. Additional tobacco lines with suppressed expression of one or more NDGs, one or more ERF genes at Nic2 locus, or a combination thereof are generated via gene silencing (e.g., RNAi, artificial/synthetic microRNA or other small RNA-mediated techniques). Exemplary RNAi cassette sequences targeting NDG1 to NDG15 are listed in Table 15.

For example, protoplasts are prepared as described in Example 10. One or more entry vectors containing sequences for transcription activator like effector proteins, specific for the target sequences of Nic1 (e.g., NDG1 or NDG2), ERF-39 like, and Nic2 (e.g., ERF189 or another ERF gene from Table 11) are synthesized and transformed into the isolated protoplasts. Protoplasts are cultured into calli. Alternatively, Nic1 and Nic2 loci mutations are achieved through CRISPR and without the use of plasmids. In this case, protoplasts are transformed with Cas9, guide RNA and polyethylene glycol (PEG).

The plants created contain a gene mutation (e.g., null mutation or deletion) in Nic1, Nic2, or both loci, and constitute a low-nicotine variety. Alternatively, a variety containing a Nic1 mutant allele is crossed to another variety containing a Nic2 mutant allele. This cross will result in cultivars with desirable genetic backgrounds having an even lower nicotine content but high leaf quality. As an alternate option, gene silencing and genome editing techniques can be utilized as described in Example 10 to introduce Nic1 and Nic2 mutations or deletions at the same time.

TABLE 15

Details of the location of the coding sequence (CDS) within Nic1 locus, and BLAST hit with the lowest E-value of the corresponding protein are provided in this Table. Sequences of inverted repeat-containing RNAi cassettes are listed as SEQ ID Nos. The T-DNA cassette sequences of the RNAi vector can be found in SEQ ID Nos. 69 and 70.

| Name | Position coordinates on SEQ ID NO: 85 | BLAST Hit Description | Blast Hit ID | Genomic sequence (SEQ ID) | cDNA sequence (SEQ ID) | Amino acid sequence (SEQ ID) | Corresponding genes from Table 10 | RNAi cassette sequence (SEQ ID) |
|---|---|---|---|---|---|---|---|---|
| NDG1 | join(385015...385449, 37135...387299, 387383...387795, 387857...389264) | PREDICTED: putative late blight resistance protein homolog R1A-3 [*Nicotiana*] | XP_009624787.1 | 86 | 101 | 116 | g100614_Scaffold0002504 | 148 and 149 |
| NDG2 | complement(join(73886...74311, 74491...74680, 74794...74934, 75026...76149, 76285...76524)) | PREDICTED: putative late blight resistance protein homolog R1B-16 [*Nicotiana*] | XP_009589795.1 | 87 | 102 | 117 | g100631_Scaffold0002504 | 150 and 151 |
| NDG3 | join(323943...323949, 324085...324464) | PREDICTED: uncharacterized protein LOC104090758 [*Nicotiana tomentosiformis*] | XP_009594228.1 | 88 | 103 | 118 | | 152 |
| NDG4 | 315634...316095 | PREDICTED: uncharacterized protein LOC104106516 [*Nicotiana tomentosiformis*] | XP_009613372.1 | 89 | 104 | 119 | | 153 |
| NDG5 | complement(join(179863...179982, 180074...180152, 180839...181455)) | PREDICTED: uncharacterized protein LOC104091789 [*Nicotiana tomentosiformis*] | XP_009595504.1 | 90 | 105 | 120 | g100618_Scaffold0002504 | 154 |
| NDG6 | complement(join(233956...234093, 234729...235030, 235166...235378, 235496...236068, 236374...236438, 236633...236874)) | PREDICTED: uncharacterized protein LOC104093328 [*Nicotiana tomentosiformis*] | XP_009597352.1 | 91 | 106 | 121 | g100617_Scaffold0002504 | 155 |
| NDG7 | join(36266...36629, 36753...36911, 37083...37384, 37655...37736, 37857...38347, 39697...39783) | PREDICTED: uncharacterized protein LOC107001234 [*Solanum pennellii*] | XP_015054850.1 | 92 | 107 | 122 | g100619_Scaffold0002504 | 156 |
| NDG8 | join(114418...114612, 115436...115956, 116268...116427, 116558...116749, 116833...117003) | PREDICTED: uncharacterized protein LOC104086561 [*Nicotiana tomentosiformis*] | XP_009589152.1 | 93 | 108 | 123 | g100620_Scaffold0002504 | 157 |

TABLE 15-continued

Details of the location of the coding sequence (CDS) within Nic1 locus, and BLAST hit with the lowest E-value of the corresponding protein are provided in this Table. Sequences of inverted repeat-containing RNAi cassettes are listed as SEQ ID Nos. The T-DNA cassette sequences of the RNAi vector can be found in SEQ ID Nos. 69 and 70.

| Name | Position coordinates on SEQ ID NO: 85 | BLAST Hit Description | Blast Hit ID | Genomic sequence (SEQ ID) | cDNA sequence (SEQ ID) | Amino acid sequence (SEQ ID) | Corresponding genes from Table 10 | RNAi cassette sequence (SEQ ID) |
|---|---|---|---|---|---|---|---|---|
| NDG9 | complement(join(262599 . . . 262791, 264178 . . . 264595, 264677 . . . 264995)) | PREDICTED: uncharacterized protein LOC107029976 [Solanum pennellii] | XP_015086886.1 | 94 | 109 | 124 | g100621_Scaffold0002504 | 158 |
| NDG10 | 335270 . . . 336187 | PREDICTED: uncharacterized protein LOC104217532 [Nicotiana sylvestris] | XP_009766114.1 | 95 | 110 | 125 | g100623_Scaffold0002504 | 159 |
| NDG11 | complement(join(196787 . . . 197330, 197459 . . . 197772, 197860 . . . 198026, 198131 . . . 198293)) | PREDICTED: uncharacterized protein LOC104107887 [Nicotiana tomentosiformis] | XP_009615097.1 | 96 | 111 | 126 | g100622_Scaffold0002504 | 160 |
| NDG12 | complement(join(340626 . . . 340850, 340943 . . . 341242, 341377 . . . 342443, 342827 . . . 342891, 345833 . . . 346446, 346782 . . . 347228)) | PREDICTED: uncharacterized protein LOC104225535 [Nicotiana sylvestris] | XP_009775660.1 | 97 | 112 | 127 | g100626_Scaffold0002504 | 161 |
| NDG13 | join(79509 . . . 79744, 79863 . . . 80141, 80301 . . . 80715) | PREDICTED: uncharacterized protein LOC104095512 [Nicotiana tomentosiformis] | XP_009599950.1 | 98 | 113 | 128 | g100627_Scaffold0002504 | 162 |
| NDG14 | complement(join(297606 . . . 297727, 299439 . . . 299551, 300249 . . . 300331, 300629 . . . 300802, 301088 . . . 301258, 301326 . . . 301450, 301535 . . . 301636, 301731 . . . 301859, 301942 . . . 302392)) | PREDICTED: uncharacterized protein LOC104215965 [Nicotiana sylvestris] | XP_009764210.1 | 99 | 114 | 129 | g100628_Scaffold0002504 | 163 |
| NDG15 | join(291110 . . . 291242, 291376 . . . 291556, 291665 . . . 292004) | PREDICTED: DNA ligase 1-like [Nicotiana sylvestris] | XP_009785055.1 | 100 | 115 | 130 | g100632_Scaffold0002504 | 164 |

TABLE 16

SNP markers flanking Nic1 or Nic2 deletion region. REF refers to the sequence of a reference TN90 allele. ALT refers to an alternative allele associated with the corresponding deletion region. Genotype in the 4 varieties (BU21, HI, LI, and LA) are shown where "00" refers to homozygous for the reference TN90 allele while "11" refers to homozygous for the ALT allele. The polymorphic site in the sequence is denoted by an "X".

| SNP Marker (SEQ ID No.) | Assc'd Locus | Relative Position to the deletion | REF | ALT | BU21 | HI | LI | LA | Sequence |
| --- | --- | --- | --- | --- | --- | --- | --- | --- | --- |
| 131 | Nic1 | Upstream | C | A | 00 | 00 | 11 | 11 | ATCATGTCTAATTGATTTAATTGCTGTATTTGCTCAAA CTGCCTTATTTGGACTATGTGAXACATGCTAGGTTAGA AATATATGTTTTAACTTGGTGTGAAATTTAATTTAATT GAGTATT (SEQ ID NO. 131) |
| 132 | Nic1 | Upstream | C | T | 00 | 00 | 11 | 11 | GCGGCTGTATACCATTTTGTACGGACCGCAGTGGGCTC ACCGTGGCCTCAATCGAGTTTGXGCGGTTCATAAAGAT GGGGGTTCAGAGAGTTGGGAGTTTAGAGATTAAGACCA ATACGGT (SEQ ID NO. 132) |
| 133 | Nic1 | Upstream | T | G | 00 | 00 | 11 | 11 | GGAAGCACTCAAGCATCCACTCTTGGAGGTGGTGGGGG AGGGTCTGGAATATTATCATTGXCCTGGTGGCTTCTCC TTTGTCTTTGAGGTACAATAGGAACCTCATCATCAATA TTGTCAT (SEQ ID NO. 133) |
| 134 | Nic1 | Downstream | T | C | 00 | 00 | 11 | 11 | ACGAAGGATAAAGTGTTTGGGTAGCAGAACAAAATGCC TTCGTCATTCCAGTCTTTAACAXATGCCAAGTGCAAAC AATACAATTTAAATTTGTAGTCTCTTCTGATGGTGTTG GACTTAC (SEQ ID NO. 134) |
| 135 | Nic1 | Downstream | C | T | 00 | 00 | 11 | 11 | ACACCTTCTTCCGGGTTAACAGAATTCCATACTCGGAT TTCTGGTTCGCAGACTGTAATAXGGAGTCAATCTTTTC CTCGATTTGGGATTTGAACCGGTGATTTGGGAAATCAT AATTATC (SEQ ID NO. 135) |
| 136 | Nic1 | Downstream | A | G | 00 | 00 | 11 | 11 | TAGCTAACAAGGAATTGGATCAATTGAGAGATTGATTA ACCCAATTAAAGAGTTTAACCTXGAGATAGTAACAACA TGACTTGAGCTCTTATCAACAGTTTTGGTTGATACCTT TTGGTCT (SEQ ID NO. 136) |
| 137 | Nic2 | Upstream | T | C | 00 | 11 | 00 | 11 | TTACATAAATATAAAGGTTTAATTGAAAGTTATACTTT TTGGTCAAACACAAATACCGTAXCAAAATAGTTCGATA CGGTTAGGTATTTTCTTGTTTGGTTCGGTACGGCTTCG ATATTAT (SEQ ID NO. 137) |
| 138 | Nic2 | Upstream | G | A | 00 | 11 | 00 | 11 | GAAAATACCGACCGAAAACGGTCGAAAATAACATATTT TTTAATTATTCCAACCGACTTCXGTCGGTTTGTTAAGA TTTAAAAAGAAATGCAAAATTATCACATAATTATATTT CCGACCG (SEQ ID NO. 138) |
| 139 | Nic2 | Upstream | G | A | 00 | 11 | 00 | 11 | GTCTGCACTTTTCTTATTGCTTATTGTTTACCCGAAAA ATGGATAGAGTTGAATTTATACXTAGTTTTAAGGGTAT GTGGTATAATTTAATACAAATCGTAAGAATAAGTAGAA ATATCAA (SEQ ID NO. 139) |
| 140 | Nic2 | Downstream | G | A | 00 | 11 | 00 | 11 | TAGGATTTTGACCGTGGTTGGGAACTATGTGAAGACAA CTCCGGAATAGAGTTATGTCGXTTCTGTTAGCTCCATT AGATGATTTTGGACTTAGGGGCGTGTCCGGATTATGTT TTGGAG (SEQ ID NO. 140) |
| 141 | Nic2 | Downstream | A | G | 00 | 11 | 00 | 11 | GTCCCTTACGAATTTGTCTTCAAATTGATACTTCTCCT TGCTAAAACACCACGATCCTTAXCCACAACTCACCCCA CGAACCCTAGCATAGAACCACACCACCCTACGGCCCTT AAGAAAC (SEQ ID NO. 141) |
| 142 | Nic2 | Downstream | T | C | 00 | 11 | 00 | 11 | GCCTCCCAGCTTAGCAAGAGTTCATCCGGCATTTCATT TTTCGATGCTACAAAGGTATCAXGGCAATCCGTCTCAT GTGTTGGATTTCAGCTCAGTCCAGTTGGACAAGGATCT ATCTTAT (SEQ ID NO. 142) |

TABLE 17

SNP markers flanking the ERF-39 like gene which is associated with Nic1 deletion region. Listed are relative positions (Pos, Upstream/Downstream), Reference allele in TN90 (REF), Alternate allele (ALT), Genotype in the 4 varieties (BU21, HI, LI, and LA BU21(, and sequence of the SNO with flanking position are provided in this table. "00" refers to homozygous for the reference TN90 allele while "11" refers to homozygous for the ALT allele and "01" refers to heterozygous. The polymorphic site in the sequence is denoted by an "X".

| SNP Marker (SEQ ID No.) | Assc'd Locus | Relative Position to ERF-39 | REF | ALT | BU21 | HI | LI | LA | Sequence |
|---|---|---|---|---|---|---|---|---|---|
| 143 | ERF-39 | Upstream | A | G | 00 | 00 | 01 | 01 | CCAAATTATTTTTGACTGTTTGACCAAAATAGCGACCAACGTTGGTCGCCATTTTTGATCXTTTGACCAAAATGGCGACCAACTTTGGTCGCTATATTTGAAAATAAATAAATAAAATAAT (SEQ ID NO. 143) |
| 144 | ERF-39 | Downstream | TG | T | 00 | 00 | 11 | 11 | TTGTTTCTCAAGAAAATCAGCATCGATCTTTTTCTTTATTATAAAGGTAATATAGATGCTXXGGGTATTAAAAGAGGACAAAATATTCTGGCATCATTTGAGATTTGCTGAGTGCAATAACA (SEQ ID NO. 144) |

TABLE 18

A comparison of gene-specific primers and flanking SNP markers for genotyping the $F_2$ population of Example 11 (segregating for nic1 and nic2 ((LA Burley 21 × TN 90 LC) (X)), F2_1 to F2_72 plants refer to plant No. 1 to 72 of Table 12).

Genotyping of Nic1 locus using gene-specific primers for g100614 Scaffold0002504 as in Table 5.

|   | 1 | 2 | 3 | 4 | 5 | 6 | 7 | 8 | 9 |
|---|---|---|---|---|---|---|---|---|---|
| A | F2_1 | F2_9 | F2_17 [a,c] | F2_25 [a,c] | F2_33 | F2_41 | F2_49 | F2_57 | F2_65 |
| B | F2_2 | F2_10 | F2_18 | F2_26 | F2_34 | F2_42 | F2_50 [a,c] | F2_58 [a,c] | F2_66 |
| C | F2_3 [a,c] | F2_11 | F2_19 [a,c] | F2_27 | F2_35 [a,c] | F2_43 | F2_51 [a,c] | F2_59 | F2_67 |
| D | F2_4 | F2_12 | F2_20 | F2_28 | F2_36 | F2_44 | F2_52 | F2_60 | F2_68 |
| E | F2_5 | F2_13 | F2_21 | F2_29 | F2_37 | F2_45 [a,c] | F2_53 | F2_61 | F2_69 [a,c] |
| F | F2_6 | F2_14 | F2_22 | F2_30 | F2_38 [a,c] | F2_46 | F2_54 | F2_62 | F2_70 |
| G | F2_7 | F2_15 | F2_23 | F2_31 | F2_39 [a,c] | F2_47 | F2_55 | F2_63 | F2_71 |
| H | F2_8 | F2_16 | F2_24 [a] | F2_32 | F2_40 | F2_48 | F2_56 | F2_64 | F2_72 [a,c] |

KASP genotyping of Nic1 using SNP marker SEQ ID No. 135

|   | 1 | 2 | 3 | 4 | 5 | 6 | 7 | 8 | 9 |
|---|---|---|---|---|---|---|---|---|---|
| A | F2_1 * | F2_9 [b] | F2_17 [a,c] | F2_25 [a,c] | F2_33 | F2_41 [b] | F2_49 | F2_57 [b] | F2_65 * |
| B | F2_2 [b] | F2_10 [b] | F2_18 | F2_26 | F2_34 | F2_42 [b] | F2_50 [a,c] | F2_58 [a,c] | F2_66 [b] |
| C | F2_3 [a,c] | F2_11 [b] | F2_19 [a,c] | F2_27 | F2_35 [a,c] | F2_43 [b] | F2_51 [b] | F2_59 [b] | F2_67 [b] |
| D | F2_4 | F2_12 [b] | F2_20 | F2_28 [b] | F2_36 [b] | F2_44 [b] | F2_52 [b] | F2_60 [b] | F2_68 [b] |
| E | F2_5 [b] | F2_13 [b] | F2_21 [b] | F2_29 [b] | F2_37 | F2_45 [a,c] | F2_53 [b] | F2_61 [b] | F2_69 [a,c] |
| F | F2_6 [b] | F2_14 | F2_22 [b] | F2_30 | F2_38 [a,c] | F2_46 [b] | F2_54 [b] | F2_62 | F2_70 [b] |
| G | F2_7 * | F2_15 [b] | F2_23 [b] | F2_31 [b] | F2_39 [a,c] | F2_47 [b] | F2_55 [b] | F2_63 [b] | F2_71 [b] |
| H | F2_8 [b] | F2_16 * | F2_24 * | F2_32 [b] | F2_40 [b] | F2_48 [b] | F2_56 * | F2_64 [b] | F2_72 [a,c] |

Genotyping of Nic2 locus using gene-specific primers for ERF 189 as in Table 5.

|   | 1 | 2 | 3 | 4 | 5 | 6 | 7 | 8 | 9 |
|---|---|---|---|---|---|---|---|---|---|
| A | F2_1 | F2_9 [a,c] | F2_17 [a,c] | F2_25 | F2_33 [a,c] | F2_41 [a,c] | F2_49 [a,c] | F2_57 | F2_65 |
| B | F2_2 | F2_10 | F2_18 | F2_26 | F2_34 | F2_42 | F2_50 | F2_58 | F2_66 |
| C | F2_3 | F2_11 [a,c] | F2_19 [a,c] | F2_27 | F2_35 | F2_43 [a,c] | F2_51 | F2_59 | F2_67 |
| D | F2_4 | F2_12 [a,c] | F2_20 | F2_28 | F2_36 | F2_44 | F2_52 [a,c] | F2_60 | F2_68 |
| E | F2_5 [a,c] | F2_13 | F2_21 [a,c] | F2_29 [a,c] | F2_37 [a] | F2_45 [a,c] | F2_53 | F2_61 | F2_69 |
| F | F2_6 | F2_14 [a,c] | F2_22 [a,c] | F2_30 | F2_38 | F2_46 [a,c] | F2_54 | F2_62 | F2_70 |
| G | F2_7 | F2_15 | F2_23 | F2_31 | F2_39 [a,c] | F2_47 | F2_55 | F2_63 | F2_71 |
| H | F2_8 | F2_16 | F2_24 [a] | F2_32 | F2_40 [a] | F2_48 [a,c] | F2_56 | F2_64 | F2_72 [a] |

KASP genotyping of Nic2 using SNP marker SEQ ID No. 137

|   | 1 | 2 | 3 | 4 | 5 | 6 | 7 | 8 | 9 |
|---|---|---|---|---|---|---|---|---|---|
| A | F2_1 * | F2_9 [a,c] | F2_17 [a,c] | F2_25 | F2_33 [b] | F2_41 [a,c] | F2_49 [a,c] | F2_57 [b] | F2_65 |
| B | F2_2 [b] | F2_10 [b] | F2_18 [b] | F2_26 [b] | F2_34 [a,c] | F2_42 [b] | F2_50 [b] | F2_58 [b] | F2_66 [b] |
| C | F2_3 [b] | F2_11 [a,c] | F2_19 [a,c] | F2_27 | F2_35 | F2_43 [a,c] | F2_51 [b] | F2_59 [b] | F2_67 [b] |
| D | F2_4 | F2_12 [a,c] | F2_20 [b] | F2_28 | F2_36 [b] | F2_44 [b] | F2_52 [a,c] | F2_60 | F2_68 [b] |
| E | F2_5 [a,c] | F2_13 [b] | F2_21 [a,c] | F2_29 [a,c] | F2_37 [b] | F2_45 [a,c] | F2_53 [b] | F2_61 | F2_69 |

TABLE 18-continued

A comparison of gene-specific primers and flanking SNP markers for genotyping the $F_2$ population of Example 11 (segregating for nic1 and nic2 ((LA Burley 21 × TN 90 LC) (X)), F2_1 to F2_72 plants refer to plant No. 1 to 72 of Table 12).

| F | F2_6 * | F2_14 $a, c$ | F2_22 $a, c$ | F2_30 $b$ | F2_38 | F2_46 $a, c$ | F2_54 $b$ | F2_62 $b$ | F2_70 |
| G | F2_7 | F2_15 $b$ | F2_23 $b$ | F2_31 | F2_39 $a, c$ | F2_47 $b$ | F2_55 $b$ | F2_63 | F2_71 $b$ |
| H | F2_8 $b$ | F2_16 $b$ | F2_24 * | F2_32 $b$ | F2_40 $b$ | F2_48 $a, c$ | F2_56 * | F2_64 $b$ | F2_72 * |

* genotype not resolved;
$a$ homozygous for either nic1 or nic2;
$b$ heterozygous for either nic1 or nic2.
$c$ shows plants where genotyping results match between gene-specific primers and flanking SNPs.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10405571B2). An electronic copy of the "Sequence Listing" will also be available from the USPTO upon request and payment of the fee set forth in 37 CFR 1.19(b)(3).

The invention claimed is:

1. A tobacco plant, or part thereof, comprising a first polymorphism in SEQ ID NO: 131 and a second polymorphism in SEQ ID NO: 137, wherein said tobacco plant comprises nicotine at a level below 25% of the nicotine level of a control plant when grown in similar growth conditions, wherein said tobacco plant is capable of producing leaves that, when cured, have a USDA grade index value of at least about 65% of the USDA grade index value of leaves of said control plant when grown and cured in similar conditions, wherein said control plant shares an essentially identical genetic background with said tobacco plant except said first and second polymorphisms, wherein said first polymorphism comprises an A nucleotide at the polymorphic site of SEQ ID NO:131, and wherein said second polymorphism comprises a C nucleotide at the polymorphic site of SEQ ID NO: 137.

2. The tobacco plant, or part thereof, of claim 1, wherein said tobacco plant is capable of producing leaves that, when cured, have a USDA grade index value of 50 or more.

3. The tobacco plant, or part thereof, of claim 1, wherein said tobacco plant comprises nicotine at a level below 15% of the nicotine level of said control plant when grown in similar growth conditions.

4. The tobacco plant, or part thereof, of claim 1, wherein said tobacco plant comprises a nicotine level less than 2.0%.

5. Cured tobacco material from the tobacco plant, or part thereof, comprising a first polymorphism in SEQ ID NO:131 and a second polymorphism in SEQ ID NO:137, wherein said tobacco plant comprises nicotine at a level below 25% of the nicotine level of a control plant when grown in similar growth conditions, wherein said tobacco plant is capable of producing leaves that, when cured, have a USDA grade index value of at least about 65% of the USDA grade index value of leaves of said control plant when grown and cured in similar conditions, wherein said control plant shares an essentially identical genetic background with said tobacco plant except said first and second polymorphisms, wherein said first polymorphism comprises an A nucleotide at the polymorphic site of SEQ ID NO: 131, and wherein said second polymorphism comprises a C nucleotide at the polymorphic site of SEQ ID NO: 137; wherein said cured tobacco material comprises said first polymorphism and said second polymorphism.

6. The cured tobacco material of claim 5, wherein said cured tobacco material comprises a lower level of nicotine compared to cured tobacco material from said control tobacco plant.

7. The cured tobacco material of claim 5, wherein said tobacco plant comprises nicotine at a level between 0.2% and 0.6%.

8. The cured tobacco material of claim 5, wherein said cured tobacco material is made by a curing process selected from the group consisting of flue curing, air curing, fire curing, and sun curing.

9. A tobacco product comprising the cured tobacco material of claim 5.

10. The tobacco product of claim 9, wherein said tobacco product is selected from the group consisting of a cigarette, a cigarillo, a non-ventilated recess filter cigarette, a vented recess filter cigarette, a cigar, snuff, pipe tobacco, cigar tobacco, cigarette tobacco, chewing tobacco, leaf tobacco, shredded tobacco, and cut tobacco.

11. The tobacco product of claim 9, wherein said tobacco product is a smokeless tobacco product.

12. The tobacco plant, or part thereof, of claim 1, wherein said tobacco plant is not a flue-cured tobacco.

13. The tobacco plant, or part thereof, of claim 1, wherein said tobacco plant is a flue-cured tobacco.

14. The tobacco plant, or part thereof, of claim 1, wherein said tobacco plant is a burley tobacco.

15. The tobacco plant, or part thereof, of claim 1, wherein said tobacco plant is an oriental tobacco.

16. The tobacco plant, or part thereof, of claim 1, wherein said tobacco plant is an air-cured tobacco.

17. The tobacco plant, or part thereof, of claim 1, wherein said tobacco plant is a fire-cured tobacco.

18. The tobacco plant, or part thereof, of claim 1, wherein said tobacco plant comprises nicotine at a level below 8% of the nicotine level of said control plant when grown in similar growth conditions.

19. The tobacco plant, or part thereof, of claim 1, wherein said first polymorphism comprises an A nucleotide at the polymorphic site of SEQ ID NO: 131 and a G nucleotide at the polymorphic site of SEQ ID NO: 136.

20. The tobacco plant, or part thereof, of claim 1, wherein said second polymorphism comprises a C nucleotide at the polymorphic site of SEQ ID NO: 137 and a C nucleotide at the polymorphic site of SEQ ID NO: 142.

* * * * *